(12) United States Patent
Rossi et al.

(10) Patent No.: US 12,138,279 B2
(45) Date of Patent: *Nov. 12, 2024

(54) BI SPECIFIC APTAMER

(71) Applicants: City of Hope, Duarte, CA (US);
Apterna Limited, London (GB)

(72) Inventors: John J. Rossi, Azusa, CA (US); Sorah Yoon, Pasadena, CA (US); Nagy Habib, London (GB); Piotr Marek Swiderski, San Dimas, CA (US)

(73) Assignee: City of Hope, Duarte, CA (US)

( * ) Notice: Subject to any disclaimer, the term of this patent is extended or adjusted under 35 U.S.C. 154(b) by 87 days.

This patent is subject to a terminal disclaimer.

(21) Appl. No.: 17/537,195

(22) Filed: Nov. 29, 2021

(65) Prior Publication Data

US 2022/0072029 A1    Mar. 10, 2022

Related U.S. Application Data

(63) Continuation of application No. 15/999,423, filed as application No. PCT/US2017/018314 on Feb. 17, 2017, now Pat. No. 11,219,635.

(60) Provisional application No. 62/297,487, filed on Feb. 19, 2016.

(51) Int. Cl.
*C07H 21/04* (2006.01)
*A61K 31/7115* (2006.01)
*C12N 15/115* (2010.01)

(52) U.S. Cl.
CPC ........ *A61K 31/7115* (2013.01); *C12N 15/115* (2013.01); *C12N 2310/16* (2013.01); *C12N 2310/318* (2013.01); *C12N 2310/321* (2013.01); *C12N 2310/322* (2013.01); *C12N 2310/3519* (2013.01); *C12N 2310/3521* (2013.01); *C12N 2310/3533* (2013.01); *C12N 2310/51* (2013.01); *C12N 2310/531* (2013.01)

(58) Field of Classification Search
None
See application file for complete search history.

(56) References Cited

U.S. PATENT DOCUMENTS

| | | | |
|---|---|---|---|
| 5,034,506 | A | 7/1991 | Summerton et al. |
| 5,235,033 | A | 8/1993 | Summerton et al. |
| 9,605,266 | B2 | 3/2017 | Rossi et al. |
| 2013/0209514 | A1 | 8/2013 | Gilboa et al. |
| 2014/0039042 | A1 | 2/2014 | Toleikis et al. |
| 2014/0056959 | A1* | 2/2014 | Giangrande ............ A61L 27/54 435/375 |
| 2018/0087053 | A1 | 3/2018 | Rossi et al. |
| 2019/0343867 | A1 | 11/2019 | Rossi et al. |

FOREIGN PATENT DOCUMENTS

| | | |
|---|---|---|
| WO | WO-2005/054868 A1 | 6/2005 |
| WO | WO-2006/121168 A1 | 11/2006 |
| WO | WO-2008/156712 A1 | 12/2008 |
| WO | WO-2010/077634 A1 | 7/2010 |
| WO | WO-2010/144295 A1 | 12/2010 |
| WO | WO-2011/049750 A1 | 4/2011 |
| WO | WO-2012/076190 A1 | 6/2012 |
| WO | WO-2012/135408 A1 | 10/2012 |
| WO | WO-2013/154735 A1 | 10/2013 |
| WO | WO-2013/163303 A2 | 10/2013 |
| WO | WO-2013/163303 A3 | 10/2013 |
| WO | WO-2014/068408 A2 | 5/2014 |
| WO | WO-2014/068408 A3 | 5/2014 |
| WO | WO-2014/147559 A1 | 9/2014 |
| WO | WO-2016/019270 A1 | 2/2016 |
| WO | WO-2016/019270 A8 | 2/2016 |
| WO | WO-2016/061386 A1 | 4/2016 |
| WO | WO-2016/127216 A1 | 8/2016 |

OTHER PUBLICATIONS

Alexakis, N. et al. (Nov. 2004). "Current standards of surgery for pancreatic cancer," *Br J Surg* 91(11):1410-1427.

Altschul, S.F. et al. (Oct. 5, 1990). "Basic local alignment search tool," *J Mol Biol* 215(3):403-410.

Altschul, S.F. et al. (Sep. 1, 1997). "Gapped BLAST and PSI-BLAST: a new generation of protein database search programs," *Nucleic Acids Research* 25(17):3389-3402.

Anonymous (Sep. 17, 2011). "Pancreatic cancer in the UK," *Lancet* 378(9796):1050.

Bagatell, R. et al. (Aug. 2004). "Altered Hsp90 function in cancer: a unique therapeutic opportunity," *Mol Cancer Ther* 3(8):1021-1030.

Beaucage, S.L. et al. (Mar. 20, 1992). "Advances in the Synthesis of Oligonucleotides by the Phosphoramidite Approach," *Tetrahedron* 48(12):2223-2311.

Benkoel. L. et al. (Feb. 2009, e-published Feb. 3, 2009). "Monoclonal antibody 16D10 to the COOH-terminal domain of the feto-acinar pancreatic protein targets pancreatic neoplastic tissues," *Mol Cancer Ther* 8(2):282-291.

Berezovski, M.V. et al. (Jul. 16, 2008, e-published Jun. 18, 2008). "Aptamer-facilitated biomarker discoery (AptaBiD)," *J Am Chem Soc* 130(28):9137-9143.

Bhattacharya, R. et al. (May 2009, e-published Apr. 14, 2009). "Recruitment of vimentin to the cell surface by β3 integrin and plectin mediates adhesion strength," *J Cell Sci* 122(Pt 9):1390-1400.

Blank, M. et al. (May 11, 2001, e-published Feb. 13, 2001). "Systematic evolution of a DNA aptamer binding to rat brain tumor microvessels. selective targeting of endothelial regulatory protein pigpen," *J Biol Chem* 276(19):16464-16468.

(Continued)

*Primary Examiner* — Kimberly Chong
(74) *Attorney, Agent, or Firm* — Mintz, Levin, Cohn, Ferris, Glovsky and Popeo, P.C.

(57) ABSTRACT

Provided are aptamers and aptamer compositions and particularly, although not exclusively, to a bi-specific aptamer capable of binding a tumor cell antigen and an immune cell surface protein.

23 Claims, 24 Drawing Sheets

Specification includes a Sequence Listing.

(56) References Cited

OTHER PUBLICATIONS

Christian, S. et al. (Nov. 24, 2003). "Nucleolin expressed at the cell surface is a marker of endothelial cells in angiogenic blood vessels," *J Cell Biol* 163(4):871-878.
Cunningham, D. et al. (Nov. 20, 2009, e-published Oct. 26, 2009). "Phase III randomized comparison of gemcitabine versus gemcitabine plus capecitabine in patients with advanced pancreatic cancer," *J Clin Oncol* 27(33):5513-5518.
Daniels, D.A. et al. (Dec. 23, 2003, e-published Dec. 15, 2003). "A tenascin-C aptamer identified by tumor cell SELEX: systematic evolution of ligands by exponential enrichment," *PNAS USA* 100(26):15416-154121.
Dua, P. et al. (Mar. 15, 2013, e-published Mar. 6, 2013). "Alkaline phosphatase ALPPL-2 is a novel pancreatic carcinoma-associated protein," *Cancer Res* 73(6):1934-1945.
Eaton, B.E. et al. (Jun. 1997). "Post-SELEX combinatorial optimization of aptamers," *Biorg Med Chem* 5(6):1087-1986.
Ellington, A.D. et al. (Aug. 30, 1990). "In vitro selection of RNA molecules that bind specific ligands," *Nature* 346(6287):818-822.
Extended European Search report mailed on Jan. 20, 2020, for European Patent Application No. 17753895.6, 13 pages.
Ferrarini, M. et al. (Jun. 19, 1992). "Unusual expression and localization of heat-shock proteins in human tumor cells," *Int J Cancer* 51(4):613-619.
Fitton, J.E. et al. (Jun. 30, 1980). "The amino acid sequence of the delta haemolysin of *Staphylococcus aureus*," *FEBS Lett* 115(2):209-212.
Fogal, V. et al. (2009, e-published Feb. 19, 2009). "Cell surface nucleolin antagonist causes endothelial cell apoptosis and normalization of tumor vasculature," *Angiogenesis* 12(1):91-100.
Fuchs, E. et al. (1994). "Intermediate filaments: structure, dynamics, function, and disease," *Annu Rev Biochem* 63:345-382.
Fulda, S. (Jul. 2009, e-published Mar. 27, 2009). "Apoptosis pathways and their therapeutic exploitation in pancreatic cancer," *J Cell Mol Med* 13(7):1221-1227.
GenBank Accession No. PXB14805.1 (Jun. 5, 2018) located at <https://www.ncbi.nlm.nih.gov/protein/PXB14805.1>, 2 pages.
GenBank Accession No. PXB14814,1 (Jun. 5, 2018) located at <https://www.ncbi.nlm.nih.gov/protein/PXB14814,1>, 2 pages.
Ghaneh, P. et al. (Aug. 2007). "Biology and management of pancreatic cancer," *Gut* 56(8):1134-1152.
Gilboa, E. et al. (Mar. 1, 2013). "Use of oligonucleotide aptamer ligands to modulate the function of immune receptors," *Clin Cancer Res* 19(5):1054-1062.
Gold L. et al. (2010) "Aptamer-based multiplexed proteomic technology for biomarker discovery," *PLoS ONE* 5(12):e15004).
Heinemann, V. et al. (Nov. 2012, e-published Jan. 4, 2012). "Systemic treatment of advanced pancreatic cancer," *Cancer Treat Rev* 38(7):843-853.
Herrmann, A. et al. (Jul. 1, 2014). "CTLA4 aptamer delivers STAT3 siRNA to tumor-associated and malignant T cells," *J Clin Invest* 124(7):2977-2987.
Hicke, B.J. et al. (Dec. 28, 2001, e-published Oct. 4, 2001). "Tenascin-C aptamers are generated using tumor cells and purified protein," *J Biol Chem* 276(52):48644-48654.
Horvath, I. et al. (Jul.-Aug. 2008, e-published Mar. 5, 2008). "Membrane-associated stress proteins: more than simply chaperones," *Biochim Biophys Acta* 1778(7-8):1653-1664.
Hunt, D.F. et al. (Sep. 1986). "Protein sequencing by tandem mass spectrometry," *PNAS USA* 83(17):6233-6237.
International Search Report mailed on May 5, 2017, for PCT Application No. PCT/US2017/018314, filed Feb. 17, 2017, 4 pages.
Jemal, A. et al. (Jul.-Aug. 2009, e-published May 27, 2009). "Cancer statistics, 2009," *CA Cancer J Clin* 59(4):225-249.
Klinkenbijl, J.H. et al. (Dec. 1999). "Adjuvant radiotherapy and 5-fluorouracil after curative resection of cancer of the pancreas and periampullary region: phase III trial of the EORTC gastrointestinal tract cancer cooperative group," *Ann Surg* 230(6):776-782.
Kokkinos, M. et al. (2007). "Vimentin and epithelial-mesenchymal transition in human breast cancer-observations in vitro and in vivo," *Cells Tissues Organs* 185(1-3):191-203.
Ku, T.H. et al. (Jul. 6, 2015). "Nucleic Acid Aptamers: An Emerging Tool for Biotechnology and Biomedical Sensing," *Sensors* 15(7):16281-16313.
Lee, A.S. et al. (Jul. 2006, e-published Jul. 1, 2006). "ER stress and cancer," *Cancer Biol Ther* 5(7):721-722.
Marcus-Sakura, C.J. (Aug. 1, 1988). "Techniques for using anti-sense oligodeoxyribonucleotides to study gene expression," *Anal. Biochem.* 172(2):289-295.
Multhoff, G. et al. (Apr. 10, 1995). "A stress-inducible 72-kDa heat-shock protein (HSP72) is expressed on the surface of human tumor cells, but not on normal cells," *Int J Cancer* 61(2):272-279.
Needleman, S.B. et al. (Mar. 1970). "A general method applicable to the search for similarities in the amino acid sequence of two proteins," *J Mol Biol* 48(3):443-453.
Neoptolemos, J.P. et al. (Mar. 2004). "A randomized trial of chemoradiotherapy and chemotherapy after resection of pancreatic cancer," *N Engl J Med* 350(12):1200-1210.
Oelkrug, C. et al. (Jan. 2015, e-published Oct. 29, 2014). "Antibody- and aptamer-strategies for GvHD prevention," *J Cell Mol Med* 19(1):11-20.
NCBI Reference Sequence Accession No. NP_001017963.2 (Jul. 10, 2019) located at <https:www.ncbi.nlm.nih.gov/protein/153792590>, 3 pages.
NCBI Reference Sequence Accession No. NM_006206.6, (Aug. 6, 2019) located at <https:www.ncbi.nlm.nih.gov/nuccore/NM_006206>, 8 pages.
NCBI Reference Sequence Accession No. NM_000579.3 (Jul. 31, 2019) located at <https:www.ncbi.nlm.nih.gov/nuccore/154091329>, 6 pages.
NCBI Reference Sequence Accession No. NM_001285829.1 (Jul. 23, 2019) located at <https:www.ncbi.nlm.nih.gov/nuccore/551894997>, 4 pages.
NCBI Reference Sequence Accession No. NM_001758.2 (Jul. 6, 2019) located at <https:www.ncbi.nlm.nih.gov/protein/156071472>, 3 pages.
NCBI Reference Sequence Accession No. AAI00912.1 (Oct. 4, 2006) located at <https:www.ncbi.nlm.nih.gov/protein/71682667>, 2 pages.
NCBI Reference Sequence Accession No. NP_003225.2, (Jul. 31, 2019) located at <https:www.ncbi.nlm.nih.gov/protein/189458817>, 4 pages.
NCBI Reference Sequence Accession No. NP_006197.1 (Aug. 6, 2019) located at <https:www.ncbi.nlm.nih.gov/protein/5453870> 5 pages.
NCBI Reference Sequence Accession No. NP_001272758.1 (Jul. 23, 2019) located at <https:www.ncbi.nlm.nih.gov/protein/551894998> 3 pages.
NCBI Reference Sequence Accession No. NP_000732.4 (Jul. 6, 2019) located at <https:www.ncbi.nlm.nih.gov/nuccore/98985799> 4 pages.
NCBI Reference Sequence Accession No. NP_000073.2 (May 28, 2019) located at <https:www.ncbi.nlm.nih.gov/nuccore/166362738> 4 pages.
NCBI Reference Sequence Accession No. NM_001768.6 (Aug. 4, 2019) located at <https:www.ncbi.nlm.nih.gov/nuccore/225007534> 4 pages.
NCBI Reference Sequence Accession No. NP_001288643.1 (May 31, 2019) located at <https:www.ncbi.nlm.nih.gov/protein/683523912> 3 pages.
NCBI Reference Sequence Accession No. NP_000570.1 (Jul. 31, 2019) located at <https:www.ncbi.nlm.nih.gov/protein/4502639> 4 pages.
NCBI Reference Sequence Accession No. NP_006128.1 (Jul. 6, 2019) located at <https:www.ncbi.nlm.nih.gov/protein/5453613> 3 pages.
NCBI Reference Sequence Accession No. NP_005339.3 (Jul. 10, 2019) located at <https:www.ncbi.nlm.nih.gov/protein/154146191> 5 pages.
NCBI Reference Sequence Accession No. NP_000607.1 (Jul. 23, 2019) located at <https:www.ncbi.nlm.nih.gov/protein/10835167> 4 pages.

(56) References Cited

OTHER PUBLICATIONS

NCBI Reference Sequence Accession No. NP_0033712 (Jul. 28, 2019) located at <https:www.ncbi.nlm.nih.gov/protein/62414289> 8 pages.
NCBI Reference Sequence Accession No. NP_001032720.1 (Aug. 7, 2019) located at <https:www.ncbi.nlm.nih.gov/protein/83700231> 3 pages.
NCBI Reference Sequence Accession No. NP_005009.2 (Aug. 13, 2019) located at <https:www.ncbi.nlm.nih.gov/protein/167857792> 4 pages.
NCBI Reference Sequence Accession No. WP_110178236.1 (Jun. 20, 2019) located at <https:www.ncbi.nlm.nih.gov/protein/WP_110178236.1> 1 page.
Oettle, H. et al. (Jan. 17, 2007). "Adjuvant chemotherapy with gemcitabine vs observation in patients undergoing curative-intent resection of pancreatic cancer: a randomized controlled trial," *JAMA* 297(3):267-277.
Panicot-Dubois, L. et al. (Nov.-Dec. 2004). "Monoclonal Antibody 16D10 to the C-Terminal Domain of the Feto-Acinar Pancreatic Protein Binds to Membrane of Human Pancreatic Tumoral SOJ-6 Cells and Inhibits the Growth of Tumor Xenografts1," *Neoplasia* 6(6):713-724.
Partial Supplementary European Search Report mailed on Oct. 8, 2019, for European Patent Application No. 17753895.6, 10 pages.
Pearson, W.R. et al. (Apr. 1988). "Improved tools for biological sequence comparison," *Proc. Nat'l. Acad. Sci. USA* 85(8):2444-2448.
Prodeus, A. et al. (Apr. 28, 2015,). "Targeting the PD-1/PD-L1 Immune Evasion Axis With DNA Aptamers as a Novel Therapeutic Strategy for the Treatment of Disseminated Cancers," *Mol Ther Nucleic Acids* 4:e237.
Que-Gewirth, N.S. et al. (Feb. 2007). "Gene therapy progress and prospects: RNA aptamers," *Gene Ther* 14(4):282-291.
Sakuishi, K. et al. (Sep. 27, 2010, e-published Sep. 6, 2010). "Targeting Tim-3 and PD-1 pathways to reverse T cell exhaustion and restore anti-tumor immunity," *J Exp Med* 207(10):2187-2194.
Santulli-Marotto, S. et al. (Nov. 1, 2003). "Multivalent RNA aptamers that inhibit CTLA-4 and enhance tumor immunity," *Cancer Res* 63(21):7483-7489.
Satelli, A. et al. (Sep. 2011, e-published Jun. 3, 2011). "Vimentin in cancer and its potential as a molecular target for cancer therapy," *Cell Mol Life Sci* 68(18):3033-3046.
Sefah, K. et al. (Jun. 2010, e-published Jun. 3, 2010). "Development of DNA aptamers using Cell-SELEX," *Nat Protoc* 5(6):1169-1185.
Shangguan, D. et al. (May 2008, e-published Mar. 26, 2008). "Cell-specific aptamer probes for membrane protein elucidation in cancer cells," *J Proteome Res* 7(5):2133-2139.
Shevchenko, A. et al. (2006). "In-gel digestion for mass spectrometric characterization of proteins and proteomes," *Nat Protoc* 1(6):2856-2860.
Sinha, N.D. et al. (Jun. 11, 1984). "Polymer support oligonucleotide synthesis XVIII: use of beta-cyanoethyl-N,N-dialkylamino-/N-morpholino phosphoramidite of deoxynucleosides for the synthesis of DNA fragments simplifying deprotection and isolation of the final product.," *Nucl Acids Res* 12(11):4539-4557.
Smith, T.F. et al. (1981). "Comparison of Biosequences," *Adv. Appl. Math* 2:482-489.
Stathis, A. et al. (Mar. 2010, e-published Jan. 26, 2010). "Advanced pancreatic carcinoma: current treatment and future challenges," *Nature reviews. Clinical oncology* 7(3): 163-172.
Tanaka, Y. et al. (Spring 2007). "RNA aptamers targeting the carboxyl terminus of KRAS oncoprotein generated by an improved SELEX with isothermal RNA amplification," *Oligonucleotides* 17(1):12-21.

Tortorella, S. et al. (Apr. 2014, e-published Feb. 27, 2014). "Transferrin receptor-mediated endocytosis: a useful target for cancer therapy," *J Membr Biol* 247(4):291-307.
Trepel, J. et al. (Aug. 2010). "Targeting the dynamic HSP90 complex in cancer," Nat tev Cancer 10(8):537-549.
Tuerk, C. et al. (Aug. 3, 1990). "Systematic evolution of ligands by exponential enrichment: RNA ligands to bacteriophage T4 DNA polymerase," *Science* 249(4968): 505-510.
Tuerk, C. (1997). "Using the SELEX combinatorial chemistry process to find high affinity nucleic acid ligands to target molecules," Methods Mol Biol 67:219-230.
Ullrich, S.J. et al. (May 1986). "A mouse tumor-specific transplantation antigen is a heat shock-related protein," *PNAS USA* 83(10):3121-3125.
Ulrich, H. et al. (Jun. 7, 2002, e-published Mar. 27, 2002). "In vitro selection of RNA aptamers that bind to cell adhesion receptors of Trypanosoma cruzi and inhibit cell invasion," *J Biol Chem* 277(23):20756-20762.
Van Simaeys, D. et al. (May 6, 2014, e-published Apr. 9, 2014). "Identification of cell membrane protein stress-induced phosphoprotein 1 as a potential ovarian cancer biomarker using aptamers selected by cell systematic evolution of ligands by exponential enrichment," *Anal Chem* 86(9):4521-4527.
Vincent, A. et al. (Aug. 2011, e-published May 26, 2011). "Pancreatic cancer," Lancet 378(97911):607-620.
Wang, C-W. et al. (Sep. 2013, e-published Jun. 19, 2013). "A new nucleic acid-based agent inhibits cytotoxic T lymphocyte-mediated immune disorders," *J Allergy Clin Immunol* 132(3):713-722.
Wang, J. et al. (Apr. 2000). "In vitro selection of novel RNA ligands that bind human cytomegalovirus and block viral infection," *RNA* 6(4):571-583.
Weintraub, H.M. et al. (Jan. 1990). "Antisense RNA and DNA," *Sci Am* 262(1):40-46.
Wheeler, L.A. et al. (Jun. 2011, e-published May 16, 2011). "Inhibition of HIV transmission in human cervicovaginal explants and humanized mice using CD4 aptamer-siRNA chimeras," *J Clin Invest* 121(6):2401-2412.
Wilner, S.E. et al. (May 15, 2012). "An RNA alternative to human transferrin: a new tool for targeting human cells," *Mol Ther Nucleic Acids* 1:e21.
Wilson, D.S. et al. (1999). "In vitro selection of functional nucleic acids," *Annu Rev Biochem* 68:611-647.
Wong, H.H. et al. (Jul. 2009, e-published Jun. 9, 2009). "Pancreatic cancer: molecular pathogenesis and new therapeutic targets," *Nat Rev Gastroenterol Hepatol* 6(7):412-422.
Written Opinion mailed on May 5, 2017, for PCT Application No. PCT/US2017/018314, filed Feb. 17, 2017, 7 pages.
Yang, M. et al. (Jan. 9, 2014). "Developing aptamer probes for acute myelogenous leukemia detection and surface protein biomarker discovery," *J Hematol Oncol* 7:5.
Yoon, S. et al. (Oct. 2010, e-published Jul. 6, 2010). "Neutralization of infectivity of porcine circovirus type 2 (PCV2) by capsid-binding 2'F-RNA aptamers," *Antiviral Res* 88(1):19-24.
Zhang, P. et al. (Oct. 2010). "Combination of an aptamer probe to CD4 and antibodies for multicolored cell phenotyping," *Am J Clin Pathol* 134(4):586-593.
Zhou, J. et al. (Nov. 2, 2012). "Current progress of RNA aptamer-based therapeutics," *Front Genet* 3:234.
Zhou, Q. et al. (Aug. 28, 2012, e-published Aug. 14, 2012). "Aptamer-containing surfaces for selective capture of CD4 expressing cells," *Langmuir* 28(34):12544-12549.
Zhou, J. et al. (Mar. 19, 2015, e-published Mar. 5, 2015). "Cell-specific RNA aptamer against human CCR5 specifically targets HIV-1 susceptible cells and inhibits HIV-1 infectivity," *Chem Biol* 22(3):379-390.

* cited by examiner

1: tP19
2: CCR5
3: tP19-CCR5 conjugate

12% Native PAGE gel

FIG. 10

SEQ ID NO:1 (truncated P19):

CUCAAUGGCGAAUGCCCGCCUAAUAGGG

SEQ ID NO:2 (full length P19):

GGGAGACAAGAAUAAACGCUCAAUGGCGAAUGCCCGCCUAAUAGGGCGUUAUGACUUGUUGAGUUCGACAGGAGGCUCACAACAGGC

SEQ ID NO:3 (P15):

GGGAGACAAGAAUAAACGCUCAAAGUUGCGGCCCAACCGUUUAAUUCAGAAUAGUGUGAUGCCUUCGACAGGAGGCUCACAACAGGC

SEQ ID NO:4 (P1):

GGGAGACAAGAAUAAACGCUCAAUGCGCUGAAUGCCCAGCCGUGAAAGCGUCGAUUUCCAUCCUUCGACAGGAGGCUCACAACAGGC

SEQ ID NO:5 (P11):

GGGAGACAAGAAUAAACGCUCAAAUGAUUGCCCAUUCGGUUAUGCUUGCGCUUCCUAAAGAGCUUCGACAGGAGGCUCACAACAGGC

SEQ ID NO:6 (P7):

GGGAGACAAGAAUAAACGCUCAAGGCCAUGUUGAAUGCCCAACUAAGCUUUGAGCUUUGGAGCUUCGACAGGAGGCUCACAACAGGC

SEQ ID NO:7 (P6):

GGGAGACAAGAAUAAACGCUCAACAAUGGAGCGUUAAACGUGAGCCAUUCGACAGGAGGCUCACAACAGGC

SEQ ID NO:8:

GAAUGCCC

FIG. 11

SEQ ID NO:9 (G3):
GGGAGGAfCGAfUGfCGGGfCfCfUfUfCGfUfUfUGfUfUfUfCGfUfCfCAfCAGAfCGAfCfUfCGf
CfCfCGA

SEQ ID NO:10 (G1, random region):
AUCGUCUAUUAGUCGCUGGC

SEQ ID NO:11 (G2, random region):
UCCUUGGCUUUUCGUCUGUG

SEQ ID NO:12 (G3, random region):
GCCUUCGUUUGUUUCGUCCA

SEQ ID NO:13 (G3 aptamer):
5'- GGG AGG ACG AUG CGG GCC UUC GUU UGU UUC GUC CAC AGA
CGA CUC GCC CGA - 3'

SEQ ID NO:14 (G4, random region):
UCCCGGCUCGUUCGUCUGUG

SEQ ID NO:15 (G5, random region):
UUCGUCAU UUUUCGUCUGGG

SEQ ID NO:16 (G6, random region):
CCUUUCGUCUGUUUCUGCGC

FIG. 12A tP19 (truncated P19):

fCfUfCAAfUGGfCGAAfUGfCfCfCGfCfCfUAAfUAGGGooooooo**mAmGfUfUfUfUfUmAfC
mAfUfUfUfUmG**

[SEQ ID NO: 17]

FIG. 12B

CCR5 aptamer:

GGGAGGAfCGAfUGfCGGGfCfCfUfUfCGfUfUfUGfUfUfUfCGfUfCfCAfCAGAfCGAfCfUfCGf
CfCfCGAooooofCmAmAmAmAfUmGfUmAmAmAmAmAfCfU

[SEQ ID NO: 18]

| | Aptamer | Linkers | Sticky End |
|---|---|---|---|

5'-C<u>UC</u>AA<u>U</u>GG<u>C</u>GAA<u>U</u>G<u>CCC</u>G<u>CC</u>AA<u>U</u>AGGGoooooooAG<u>UUUUUU</u>ACA<u>UUUUU</u>G -3'
(SEQ ID NO:39)

SE1     5'-AGUUUUUUACAUUUUG-3' [SEQ ID NO:25]
SE2     3'-UCAAAAAAUGUAAAAC-5' complementary to SE1 3'-5' [SEQ ID NO:26]
SE2     5'-CAAAAUGUAAAAAACU-3' complementary to SE1 5'-3' [SEQ ID NO:27]

FIG. 14A (i) P19:
GGGAGAfCAAGAAfUAAAfCGfCfUfCAAfUGGfCGAAfUGfCfCfCGfCfCfUAAfUfAGGGfCGf
UfUAfUGAfCfUfUGfUfUGAGfUfUfCGAfCAGGAGGfCfUfCAfCAAfCAGGfCooooooomAmGf
UfUfUfUfUfUmAfCmAfUfUfUfUmG
[SEQ ID NO:19]

(ii) P1:
GGGAGAfCAAGAAfUAAAfCGfCfUfCAAfUGfCGfCfUGAAfUGfCfCfCAGfCfCGfUGAAAGfC
GfUfCGAfUfUfUfCfCAfUfCfCfUfCGAfCAGGAGGfCfUfCAfCAAfCAGGfCooooooomAmG
fUfUfUfUfUfUmAfCmAfUfUfUfUmG
[SEQ ID NO:20]

(iii) P15:
GGGAGAfCAAGAAfUAAAfCGfCfUfCAAAGfUfUGfCGGfCfCfCAAfCfCGfUfUfUAAfUfUfCA
GAAfUAGfUGfUGAfUGfCfCfUfUfCGAfCAGGAGGfCfUfCAfCAAfCAGGfCooooooomAmGf
UfUfUfUfUfUmAfCmAfUfUfUfUmG
[SEQ ID NO:21]

(iv) P11:
GGGAGAfCAAGAAfUAAAfCGfCfUfCAAAfUGAfUfUGfCfCfCAfUfUfCGGfUfUAfUGfCfUfUG
fCGfCfUfUfUfCfCfUAAAGAGfCfUfUfUfCfGAfCAGGAGGfCfUfCAfCAAfCAGGfCooooooomAm
GfUfUfUfUfUfUmAfCmAfUfUfUfUmG
[SEQ ID NO:22]

(v) P7:
GGGAGAfCAAGAAfUAAAfCGfCfUfCAAGGfCfCAfUGfUfUGAAfUGfCfCfCAAfCfUAAGfCfU
fUfUGAGfCfUfUfUGGAfCfUfUfCGAfCAGGAGGfCfUfCAfCAAfCAGGfCooooooomAmGf
UfUfUfUfUmAfCmAfUfUfUfUmG
[SEQ ID NO:23]

(vi) P6:
GGGAGAfCAAGAAfUAAAfCGfCfUfCAAfCAAfUGGfAGfCGfUfUAAAfCGfUGAGfCfCAfUfUf
CGAfCAGGAGGfCfUfCAfCAAfCAGGfCooooooo**mAmGfUfUfUfUfUfUmAfCmAfUfUfUfU
mG**
[SEQ ID NO:24]

FIG. 14B

CCR5 aptamer:

GGGAGGAfCGAfUGfCGGGfCfCfUfUfCGfUfUfUGfUfUfUfCGfUfCfCAfCAGAfCGAfCfUfCGf
CfCfCGAoooootCmAmAmAmAfUmGfUmAmAmAmAmAfCfU
[SEQ ID NO: 18]

SE1  5'-AGUUUUUUACAUUUUG-3'      [SEQ ID NO: 25]
SE2  3'-UCAAAAAAUGUAAAAC-5'      [SEQ ID NO: 26] complementary to SE1 3'-5'
SE2  5'-CAAAAUGUAAAAAACU-3'      [SEQ ID NO: 27] complementary to SE1 5'-3'

FIG. 19A

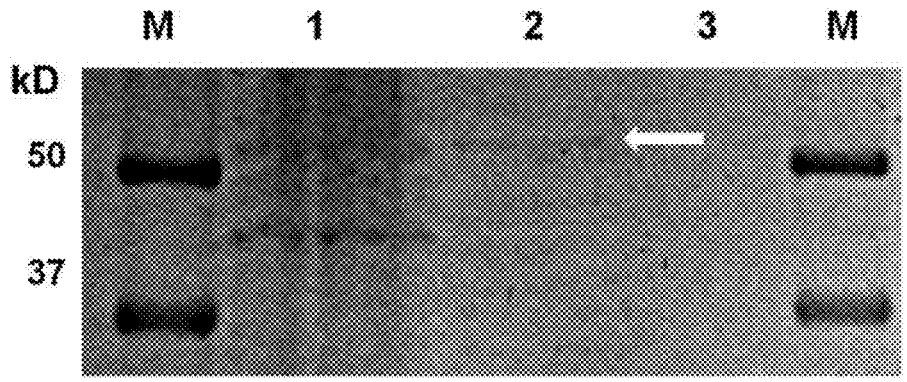

FIG. 19B

```
MSTRSVSSSS YRRMFGGPGT ASRPSSSRSY VTTSTRTYSL GSALRPSTSR
SLYASSPGGV YATRSSAVRL RSSVPGVRLL QDSVDFSLAD AINTEFKNTR
TNEKVELQEL NDRFANYIDK VRFLEQQNKI LLAELEQLKG QGKSRLGDLY
EEEMRELRRQ VDQLTNDKAR VEVERDNLAE DIMRLREKLQ EEMLQREEAE
NTLQSFRQDV DNASLARLDL ERKVESLQEE IAFLKKLHEE EIQELQAQIQ
EQHVQIDVDV SKPDLTAALR DVRQQYESVA AKNLQEAEEW YKSKFADLSE
AANRNNDALR QAKQESTEYR RQVQSLTCEV DALKGTNESL ERQMREMEEN
FAVEAANYQD TIGRLQDEIQ NMKEEMARHL REYQDLLNVK MALDIEIATY
RKLLEGEESR ISLPLPNFSS LNLRETNLDS LPLVDTHSKR TLLIKTVETR
DGQVINETSQ HHDDLE
```

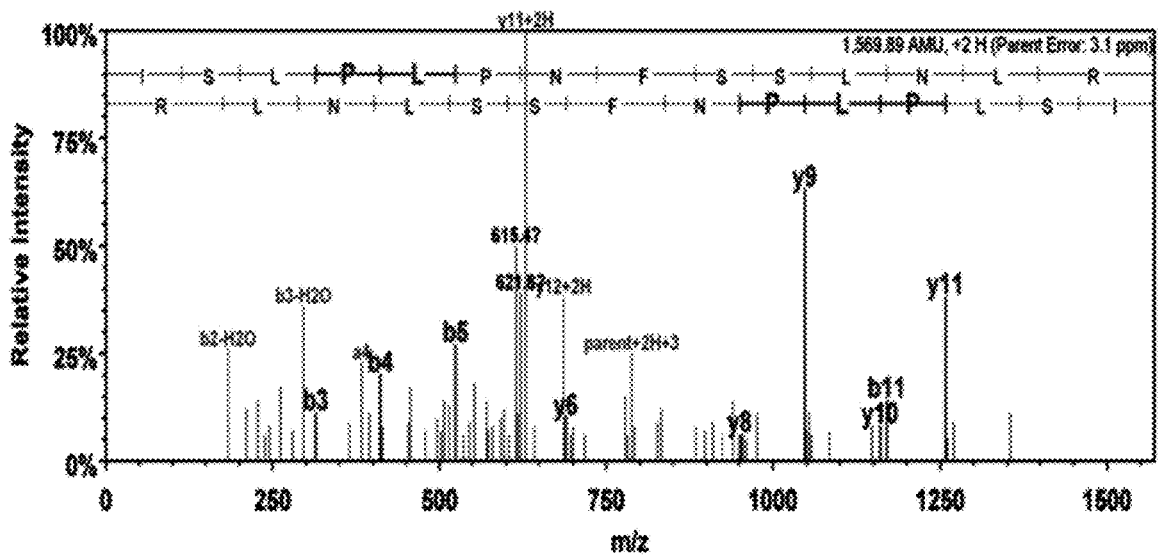

FIG. 19C

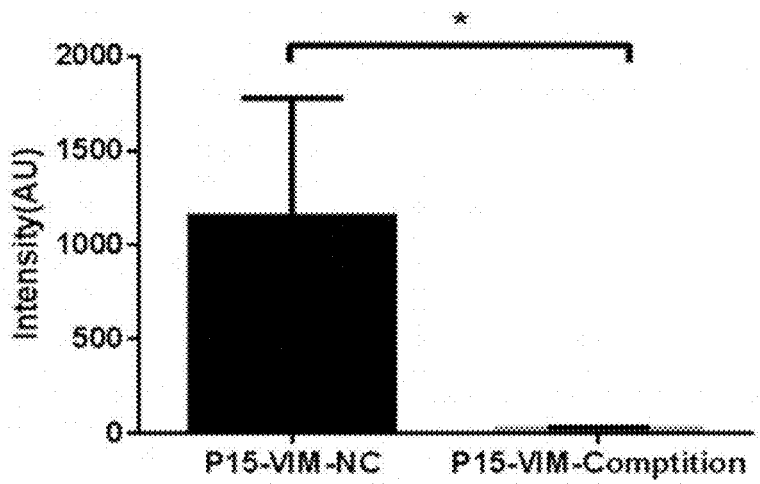

FIG. 20

TR14:
5'GGGAGACAAGAAUAAACGCUCAAUGCGUUCACGUUUAUUCACAUUUUUGAAUU
GAGCAUGAGCUUCGACAGGAGGCUCACAACAGGC3'
[SEQ ID NO:28]

TR18:
5'GGGAGACAAGAAUAAACGCUCAAUGCGUUCACGUUUAUUCACAUUUUUGAAUU
GAGCAUGAGCUUCGACAGGAGGCUCACAACAGGC3'
[SEQ ID NO:29]

truncated TfR aptamer:
5'GGGGCUCAAUGCGUUCACGUUUAUUCACAUUUUUGAAUUGAGC3'
[SEQ ID NO:30]

FIG. 21

PDR3:
GGGAGAGCGGAAGCGUGCUGGGCCUGCUCUUUAAUAAACCCACUUUCGAACAU
CAGCGUAUGUCCAUAACCCAGAGGUGAUGGAUCCCCC
[SEQ ID NO:31]

PDR9:
GGGAGAGCGGAAGCGUGCUGGGCCUAUUGCAUCUUUCUGUUAUUUCCGAAUCC
GUCCCGACUGUCAUAACCCAGAGGUGAUGGAUCCCCC
[SEQ ID NO:32]

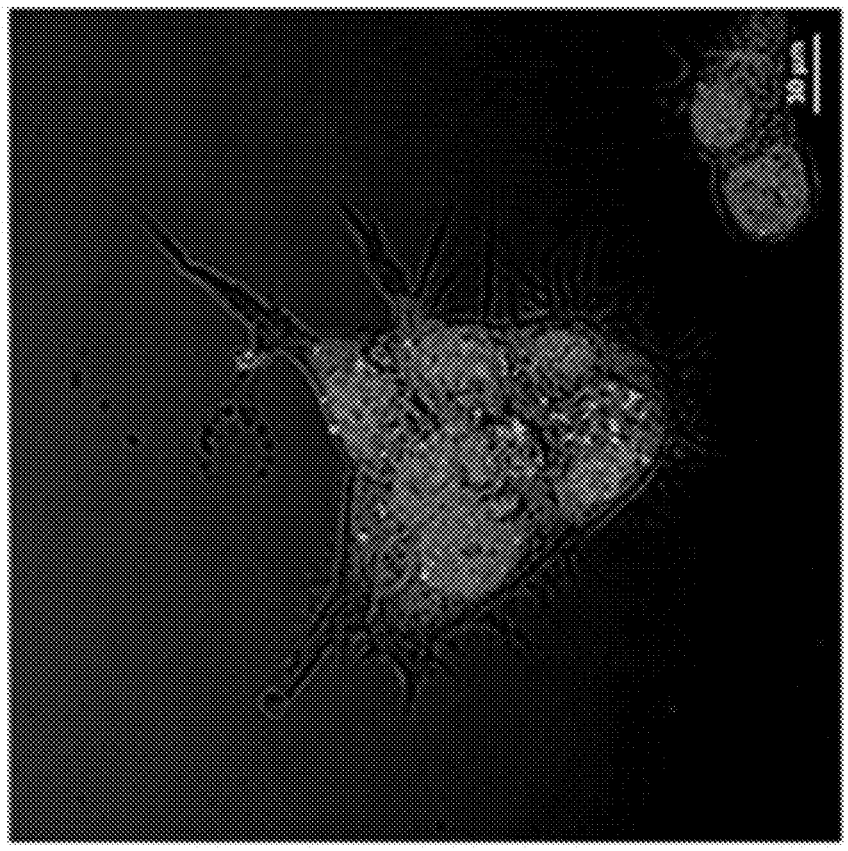
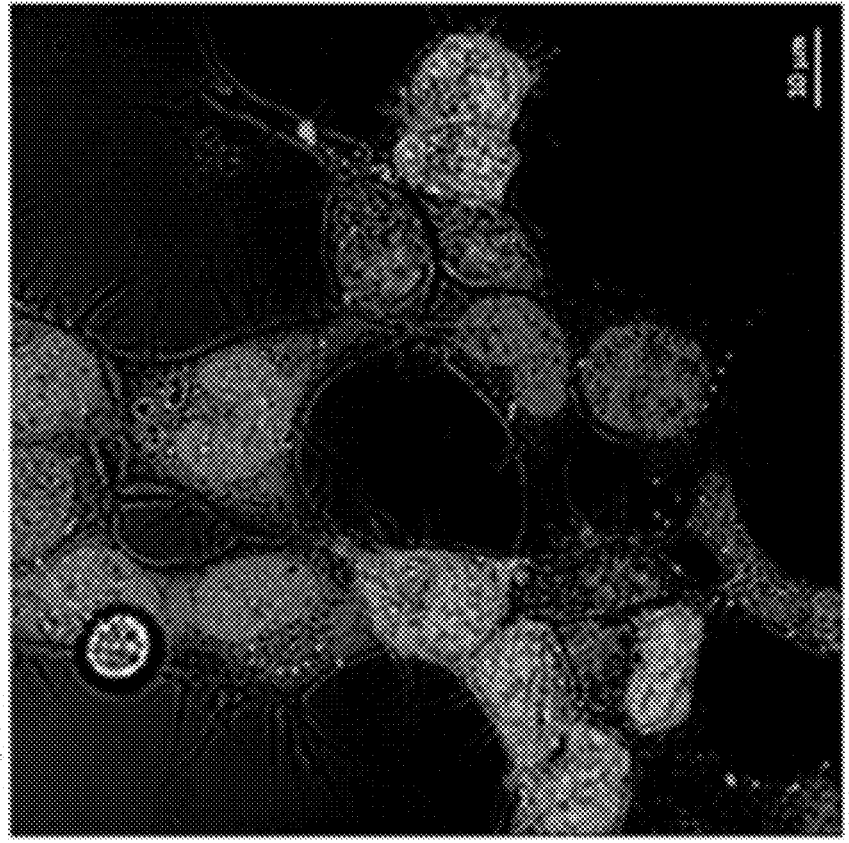
FIG. 24A
hCD3-C3e2     hCD3-C3e2
Positive to human CD3e

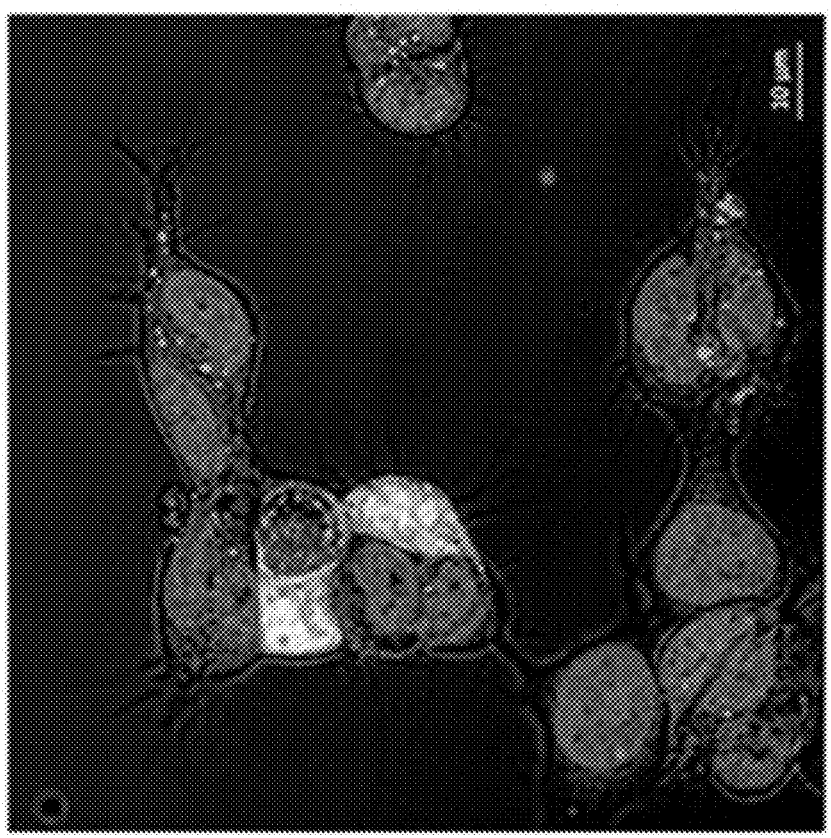
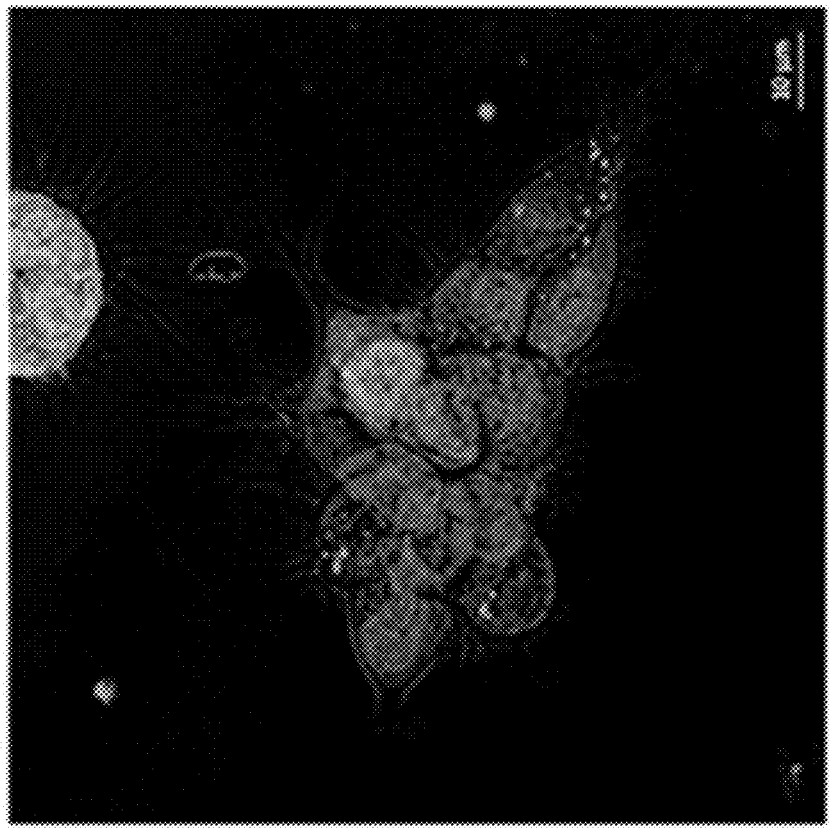
FIG. 24B

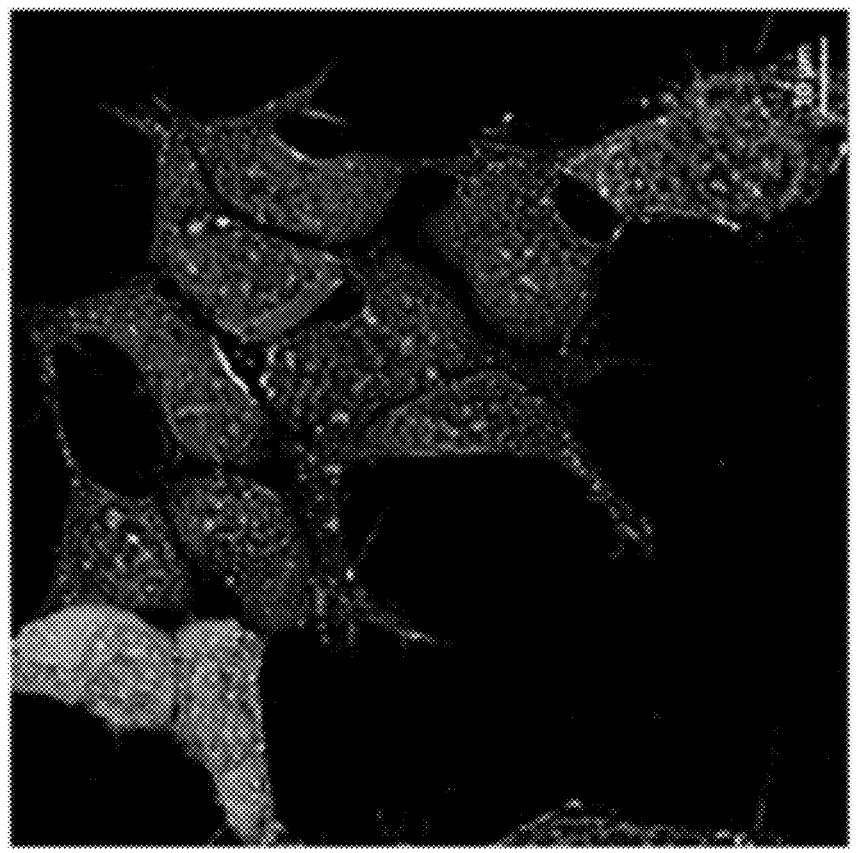
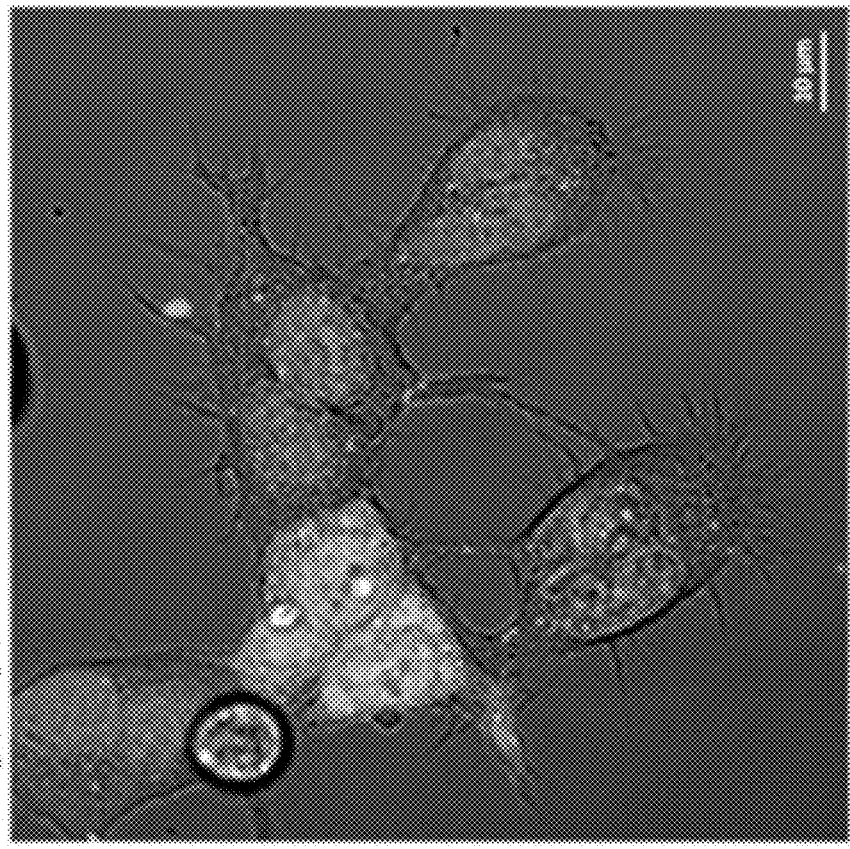
FIG. 25A
hCD3-C3e3
hCD3-C3e3 Positive to human CD3ε

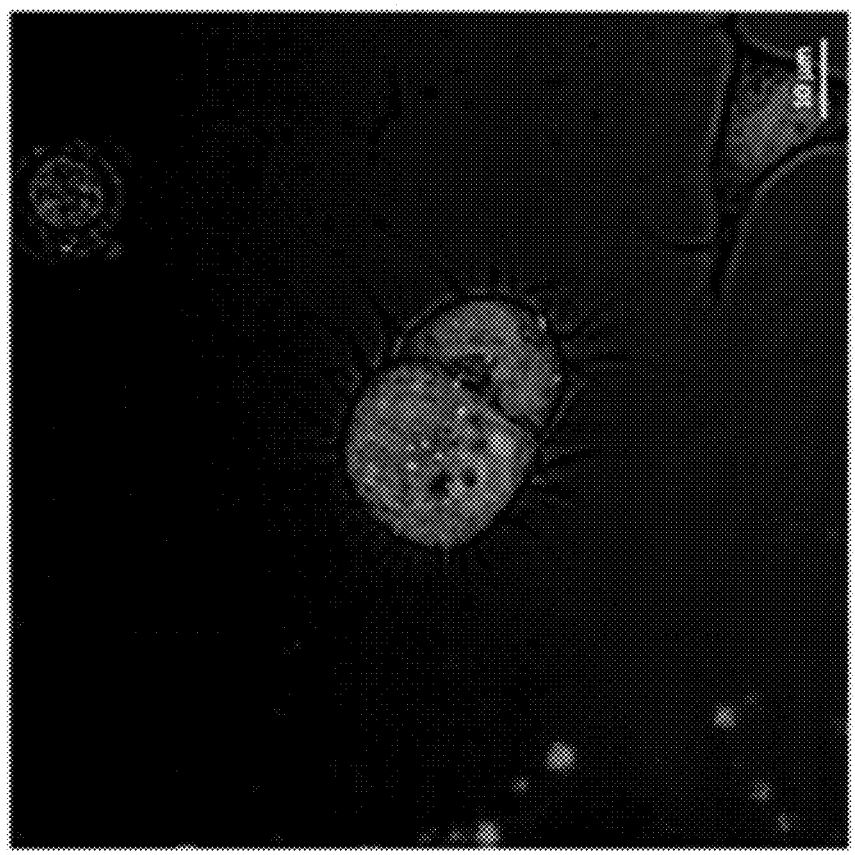
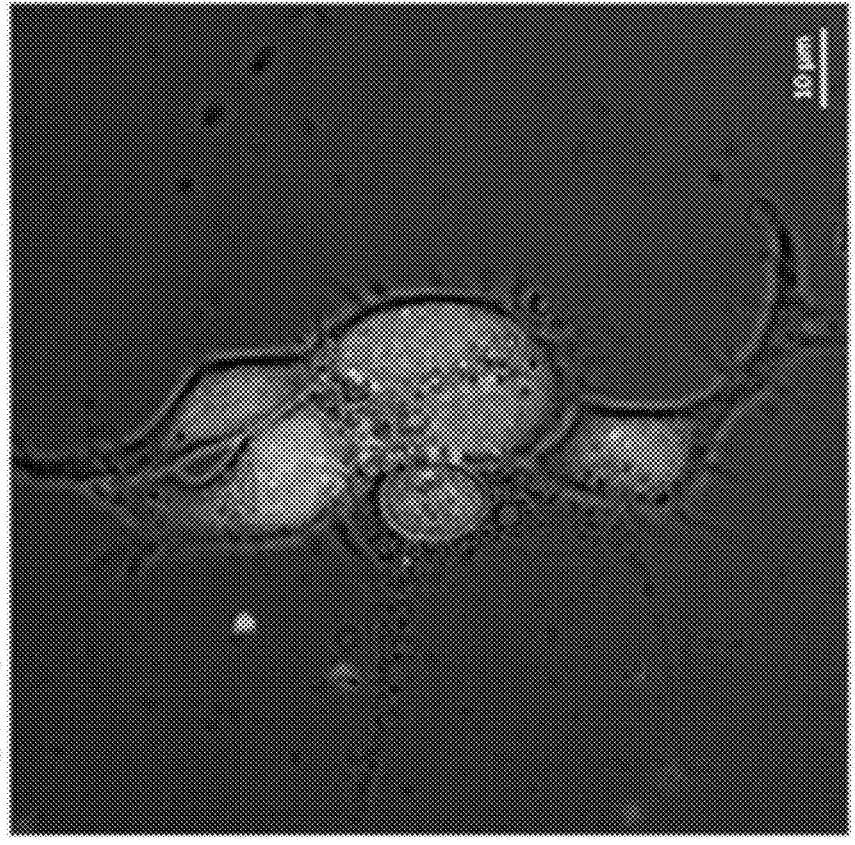
FIG. 25B

BI SPECIFIC APTAMER

CROSS-REFERENCES TO RELATED APPLICATIONS

This application is a continuation of U.S. application Ser. No. 15/999,423 filed Aug. 17, 2018, issued as U.S. Pat. No. 11,219,635, which is a Section 371 US National Phase of International Application No. PCT/US2017/018314 filed Feb. 17, 2017, which claims priority to U.S. Application No. 62/297,487 filed Feb. 19, 2016, the content of which is incorporated herein by reference in its entirety and for all purposes.

REFERENCE TO A "SEQUENCE LISTING," A TABLE, OR A COMPUTER PROGRAM LISTING APPENDIX SUBMITTED ON A COMPACT DISK

The Sequence Listing written in file 048440-608C01US_ST25.TXT, created on Nov. 29, 2021, 36, 119 bytes, machine format IBM-PC, MS Windows operating system, is hereby incorporated by reference.

BACKGROUND OF THE INVENTION

The present invention relates to aptamers and aptamer compositions and particularly, although not exclusively, to a bi-specific aptamer capable of binding a tumor cell antigen and an immune cell surface protein.

Pancreatic ductal adenocarcinoma (PDAC) is the fourth most common cause of cancer death in the United States, accounting for 30,000 deaths yearly in the US (Jemal, A. et al. Cancer statistics, 2009. *CA Cancer J Clin* 59, 225-249 (2009)). Despite great efforts to improve treatment for patients with pancreatic cancer, limited progress has been made (Stathis, A. & Moore, M. J. Advanced pancreatic carcinoma: current treatment and future challenges. *Nature reviews. Clinical oncology* 7, 163-172 (2010); Pancreatic cancer in the UK. *Lancet* 378, 1050 (2011)). Although much research has been conducted to develop improved systemic therapies for pancreatic cancer, gemcitabine as a single agent given postoperatively remains the current standard of care. Combinations with other chemotherapeutic drugs or biological agents given as a palliative setting for unresectable pancreatic cancer or adjuvant setting following resection have resulted in limited improvement (Klinkenbijl, J. H. et al. Adjuvant radiotherapy and 5-fluorouracil after curative resection of cancer of the pancreas and periampullary region: phase III trial of the EORTC gastrointestinal tract cancer cooperative group. *Annals of surgery* 230, 776-782; discussion 782-774 (1999); Neoptolemos, J. P. et al. A randomized trial of chemoradiotherapy and chemotherapy after resection of pancreatic cancer. *The New England Journal of Medicine* 350, 1200-1210 (2004); Oettle, H. et al. Adjuvant chemotherapy with gemcitabine vs observation in patients undergoing curative-intent resection of pancreatic cancer: a randomized controlled trial. *JAIUJA: the journal of the American 1Uedical Association* 297, 267-277 (2007)). The 5 year survival of patients with pancreatic cancer, despite numerous phase 3 trials, remains less than 5% after resection (Vincent, A., Herman, J., Schulick, R., Hruban, R. H. & Goggins, M. Pancreatic cancer. *Lancet* 378, 607-620 (2011); Alexakis, N. et al. Current standards of surgery for pancreatic cancer. *The British Journal of Surgery* 91, 1410-1427 (2004); Ghaneh, P., Costello, E. & Neoptolemos, J. P. Biology and management of pancreatic cancer. *Gut* 56, 1134-1152 (2007)). The majority of patients will present with either local or systemic recurrence within 2 years following resection and postoperative adjuvant chemotherapy.

Currently, the most effective single agent gemcitabine achieves an improved 1-year survival rate from 16 to 19%. The addition of Tarceva® (erlotinib) in a randomized study added a median of 11 days to overall survival (Cunningham, D. et al. Phase III randomized comparison of gemcitabine versus gemcitabine plus capecitabine in patients with advanced pancreatic cancer. *Journal of clinical oncology: official journal of the American Society of Clinical Oncology* 27, 5513-5518 (2009). Heinemann, V., Haas, M. & Boeck, S. Systemic treatment of advanced pancreatic cancer. *Cancer treatment reviews* 38, 843-853 (2012)). This limitation of conventional treatment is due to the profound resistance of PDAC cells towards anti-cancer drugs emerging from the efficient protection against chemotherapeutic drugs (Wong, H. H. & Lemoine, N. R. Pancreatic cancer: molecular pathogenesis and new therapeutic targets. *Nat Rev Gastroenterol Hepatol* 6, 412-422 (2009); Fulda, S. Apoptosis pathways and their therapeutic exploitation in pancreatic cancer. *J Cell 1Uol 1Ued* 13, 1221-1227 (2009)). Therefore, it is imperative to develop new therapeutic strategies for this devastating disease. Provided herein are solutions to these and other problems in the art.

BRIEF SUMMARY OF THE INVENTION

The inventors have provided a nucleic acid composition capable of binding to a tumor cell antigen and an immune cell surface protein. This bi-specific aptamer is a capable of binding to cell surface proteins present on a tumor cell and simultaneously binding to a cell surface protein on an immune cell, e.g. lymphocyte, T-cell, T-helper cell, cytotoxic T cell, CD8+ T-cell, CD4+ T-cell, B cell, leukocyte, macrophage, neutrophil, dendritic cell, preferably a T-cell. The bi-specific aptamer forms a bridge between the two cell types and allows for an enhanced immune response to the tumor cell, improved T-cell engagement and improved tumor cell killing. The bi-specific aptamer is formed from a nucleic acid compound (aptamer) capable of binding to a tumor cell antigen in complex with a nucleic acid compound (aptamer) capable of binding to an immune cell surface protein. The two aptamer components may form the bi-specific aptamer complex through covalent or non-covalent association. Bi-specific aptamers according to the present invention may comprise a complex of a tumor cell binding aptamer and an immune cell binding aptamer.

The bi-specific aptamer is useful in therapeutic, diagnostic and imaging applications. Pharmaceutical, diagnostic and imaging compositions comprising the bi-specific aptamer are provided. Methods of treatment, particularly of cancer, comprising administering the bi-specific aptamer to a subject in need of treatment are also provided. Diagnostic and imaging methods involving the use of the bi-specific aptamer are also provided. The bi-specific aptamer may also be conjugated to a compound moiety, which may be a therapeutic, diagnostic or imaging moiety.

In one aspect of the present invention a bi-specific aptamer capable of binding a tumor cell antigen and an immune cell surface protein is provided.

In some embodiments the tumor cell antigen is HSP70, vimentin, HSP90, TfR or PDGFR-a.

In some embodiments the immune cell surface protein is selected from the group consisting of CCR5, CCR7, CD2, CD3, CD4, CD7, CD8, PD-1, CTLA4.

In another aspect of the present invention a bi-specific aptamer capable of binding HSP70 and an immune cell surface protein is provided. The nucleic acid sequence of three HSP70 binding aptamers is shown in FIG. 10 as SEQ ID NOs: 1, 2 and 4.

In another aspect of the present invention a bi-specific aptamer capable of binding vimentin and an immune cell surface protein is provided. The nucleic acid sequence of a vimentin binding aptamer is shown in FIG. 10 as SEQ ID NO:3.

In another aspect of the present invention a bi-specific aptamer capable of binding HSP90 and an immune cell surface protein is provided. The nucleic acid sequence of three HSP90 binding aptamers is shown in FIG. 10 as SEQ ID NOs:5, 6 and 7.

In another aspect of the present invention a bi-specific aptamer capable of binding TfR and an immune cell surface protein is provided.

In another aspect of the present invention a bi-specific aptamer capable of binding PDGFR-a and an immune cell surface protein is provided.

In some embodiments the immune cell surface protein is selected from the group consisting of CCR5, CCR7, CD2, CD3, CD4, CD7, CD8, PD-1, CTLA4.

In another aspect of the present invention a bi-specific aptamer capable of binding a cancer cell and an immune cell is provided. In some embodiments a bi-specific aptamer capable of binding a pancreatic cancer cell and an immune cell is provided. The nucleic acid sequence of pancreatic cancer binding aptamers is shown in FIG. 10 as SEQ ID NOs:1 to 8. The immune cell may be a lymphocyte, white blood cell, T-cell (thymocyte), T-helper cell, cytotoxic T-cell, CD8+ T-cell, CD4+ T-cell, memory T-cell, suppressor T-cell, natural killer T-cell, gamma delta T-cell, B cell, natural killer cell, leukocyte, macrophage, neutrophil, dendritic cell. In some embodiments the immune cell may be a T-cell, preferably a CD8+ T-cell and/or a CD4+ T-cell. In some embodiments the immune cell is a cytotoxic T-cell.

In another aspect of the present invention a bi-specific aptamer capable of binding HSP70 and CCR5 is provided. In another aspect of the present invention a bi-specific aptamer capable of binding HSP70 and CCR7 is provided. In another aspect of the present invention a bi-specific aptamer capable of binding HSP70 and CD2 is provided. In another aspect of the present invention a bi-specific aptamer capable of binding HSP70 and CD3 is provided. In another aspect of the present invention a bi-specific aptamer capable of binding HSP70 and CD4 is provided. In another aspect of the present invention a bi-specific aptamer capable of binding HSP70 and CD7 is provided. In another aspect of the present invention a bi-specific aptamer capable of binding HSP70 and CD8 is provided. In another aspect of the present invention a bi-specific aptamer capable of binding HSP70 and PD-1 is provided. In another aspect of the present invention a bi-specific aptamer capable of binding HSP70 and CTLA4 is provided. In some preferred embodiments the HSP70 is mHSP70.

In another aspect of the present invention a bi-specific aptamer capable of binding vimentin and CCR5 is provided. In another aspect of the present invention a bi-specific aptamer capable of binding vimentin and CCR7 is provided. In another aspect of the present invention a bi-specific aptamer capable of binding vimentin and CD2 is provided. In another aspect of the present invention a bi-specific aptamer capable of binding vimentin and CD3 is provided. In another aspect of the present invention a bi-specific aptamer capable of binding vimentin and CD4 is provided. In another aspect of the present invention a bi-specific aptamer capable of binding vimentin and CD7 is provided. In another aspect of the present invention a bi-specific aptamer capable of binding vimentin and CD8 is provided. In another aspect of the present invention a bi-specific aptamer capable of binding vimentin and PD-1 is provided. In another aspect of the present invention a bi-specific aptamer capable of binding vimentin and CTLA4 is provided.

In another aspect of the present invention a bi-specific aptamer capable of binding HSP90 and CCR5 is provided. In another aspect of the present invention a bi-specific aptamer capable of binding HSP90 and CCR7 is provided. In another aspect of the present invention a bi-specific aptamer capable of binding HSP90 and CD2 is provided. In another aspect of the present invention a bi-specific aptamer capable of binding HSP90 and CD3 is provided. In another aspect of the present invention a bi-specific aptamer capable of binding HSP90 and CD4 is provided. In another aspect of the present invention a bi-specific aptamer capable of binding HSP90 and CD7 is provided. In another aspect of the present invention a bi-specific aptamer capable of binding HSP90 and CD8 is provided. In another aspect of the present invention a bi-specific aptamer capable of binding HSP90 and PD-1 is provided. In another aspect of the present invention a bi-specific aptamer capable of binding HSP90 and CTLA4 is provided.

In another aspect of the present invention a bi-specific aptamer capable of binding a pancreatic cancer cell and CCR5 is provided. In another aspect of the present invention a bi-specific aptamer capable of binding a pancreatic cancer cell and CCR7 is provided. In another aspect of the present invention a bi-specific aptamer capable of binding a pancreatic cancer cell and CD2 is provided. In another aspect of the present invention a bi-specific aptamer capable of binding a pancreatic cancer cell and CD3 is provided. In another aspect of the present invention a bi-specific aptamer capable of binding a pancreatic cancer cell and CD4 is provided. In another aspect of the present invention a bi-specific aptamer capable of binding a pancreatic cancer cell and CD7 is provided. In another aspect of the present invention a bi-specific aptamer capable of binding a pancreatic cancer cell and CD8 is provided. In another aspect of the present invention a bi-specific aptamer capable of binding a pancreatic cancer cell and PD-1 is provided. In another aspect of the present invention a bi-specific aptamer capable of binding a pancreatic cancer cell and CTLA4 is provided.

In another aspect of the present invention a bi-specific aptamer capable of binding TfR and CCR5 is provided. In another aspect of the present invention a bi-specific aptamer capable of binding TfR and CCR7 is provided. In another aspect of the present invention a bi-specific aptamer capable of binding TfR and CD2 is provided. In another aspect of the present invention a bi-specific aptamer capable of binding TfR and CD3 is provided.

In another aspect of the present invention a bi-specific aptamer capable of binding TfR and CD4 is provided. In another aspect of the present invention a bi-specific aptamer capable of binding TfR and CD7 is provided. In another aspect of the present invention a bi-specific aptamer capable of binding TfR and CD8 is provided. In another aspect of the present invention a bi-specific aptamer capable of binding TfR and PD-1 is provided. In another aspect of the present invention a bi-specific aptamer capable of binding TfR and CTLA4 is provided.

In another aspect of the present invention a bi-specific aptamer capable of binding PDGFR-a and CCR5 is provided. In another aspect of the present invention a bi-specific aptamer capable of binding PDGFR-a and CCR7 is provided. In another aspect of the present invention a bi-specific aptamer capable of binding PDGFR-a and CD2 is provided. In another aspect of the present invention a bi-specific aptamer capable of binding PDGFR-a and CD3 is provided. In another aspect of the present invention a bi-specific aptamer capable of binding PDGFR-a and CD4 is provided. In another aspect of the present invention a bi-specific aptamer capable of binding PDGFR-a and CD7 is provided. In another aspect of the present invention a bi-specific aptamer capable of binding PDGFR-a and CD8 is provided. In another aspect of the present invention a bi-specific aptamer capable of binding PDGFR-a and PD-1 is provided. In another aspect of the present invention a bi-specific aptamer capable of binding PDGFR-a and CTLA4 is provided.

In some aspects of the present invention the bi-specific aptamer comprises the nucleic acid sequence of one of SEQ ID NOs: 1 to 8 or a nucleic acid sequence having at least 80% sequence identity to one of SEQ ID NOs: 1 to 8. The nucleic acid sequence of the region of the aptamer capable of binding to HSP70, vimentin, HSP90 or a cancer cell, e.g. pancreatic cancer cell, may comprise, or consist of, one of SEQ ID NOs: 1 to 8 or a nucleic acid sequence having at least 80% sequence identity to one of SEQ ID NOs: 1 to 8.

In some aspects of the present invention the bi-specific aptamer comprises the nucleic acid sequence of one of SEQ ID NOs: 1, 2 and 4 or a nucleic acid sequence having at least 80% sequence identity to one of SEQ ID NOs: 1, 2 and 4. The nucleic acid sequence of the region of the aptamer capable of binding to HSP70 or a cancer cell, e.g. pancreatic cancer cell, may comprise, or consist of, one of SEQ ID NOs: 1, 2 and 4 or a nucleic acid sequence having at least 80% sequence identity to one of SEQ ID NOs: 1, 2 and 4.

In some embodiments the bi-specific aptamer comprises the nucleic acid sequence of SEQ ID NO:3 or a nucleic acid sequence having at least 80% sequence identity to SEQ ID NO:3. The nucleic acid sequence of the region of the aptamer capable of binding to vimentin or a cancer cell, e.g. pancreatic cancer cell, may comprise, or consist of, SEQ ID NO:3 or a nucleic acid sequence having at least 80% sequence identity to SEQ ID NO:3.

In some aspects of the present invention the bi-specific aptamer comprises the nucleic acid sequence of one of SEQ ID NOs:5, 6 and 7 or a nucleic acid sequence having at least 80% sequence identity to one of SEQ ID NOs:5, 6 and 7. The nucleic acid sequence of the region of the aptamer capable of binding to HSP90 or a cancer cell, e.g. pancreatic cancer cell, may comprise, or consist of, one of SEQ ID NOs:5, 6 and 7 or a nucleic acid sequence having at least 80% sequence identity to one of SEQ ID NOs:5, 6 and 7.

In some aspects of the present invention the bi-specific aptamer comprises the nucleic acid sequence of one of SEQ ID NOS:28, 29 and 30 or a nucleic acid sequence having at least 80% sequence identity to one of SEQ ID NOs:28, 29 and 30. The nucleic acid sequence of the region of the aptamer capable of binding to TfR or a cancer cell, e.g. pancreatic cancer cell, may comprise, or consist of, one of SEQ ID NOs:28, 29 and 30 or a nucleic acid sequence having at least 80% sequence identity to one of SEQ ID NOs:28, 29 and 30.

In some aspects of the present invention the bi-specific aptamer comprises the nucleic acid sequence of one of SEQ ID NOs:31 and 32 or a nucleic acid sequence having at least 80% sequence identity to one of SEQ ID NOs:31 and 32. The nucleic acid sequence of the region of the aptamer capable of binding to PDGFR-a or a cancer cell, e.g. pancreatic cancer cell, may comprise, or consist of, one of SEQ ID NOs:31 and 32 or a nucleic acid sequence having at least 80% sequence identity to one of SEQ ID NOs:31 and 32.

In some embodiments the bi-specific aptamer comprises the nucleic acid sequence of one of SEQ ID NOs:9 to 16 or a nucleic acid sequence having at least 80% sequence identity to one of SEQ ID NOs:9 to 16. The nucleic acid sequence of the region of the aptamer capable of binding to CCR5 may comprise, or consist of, one of SEQ ID NOs:9 to 16 or a nucleic acid sequence having at least 80% sequence identity to one of SEQ ID NOs:9 to 16.

The bi-specific aptamer may comprise a complex, preferably a non-covalent complex, of SEQ ID Nos 17 and 18, or a complex of a nucleic acid sequence having at least 80% sequence identity to SEQ ID NO: 17 with a nucleic acid sequence having at least 80% sequence identity to SEQ ID NO: 18.

In some aspects of the present invention a bi-specific aptamer comprises, or consists of, a nucleic acid sequence selected from one of: SEQ ID NOs: 1, 2 or 4; SEQ ID NO:3; SEQ ID NOs:5, 6 or 7; SEQ ID NOs:28, 29 or 30; SEQ ID NOs:31 or 32, or a nucleic acid sequence having at least 80% sequence identity to one of said sequences, and a nucleic acid sequence comprising, or consisting of, one of SEQ ID NOs:9 to 16, or a nucleic acid sequence having at least 80% sequence identity to one of said sequences.

In some aspects of the present invention a bi-specific aptamer comprises one of SEQ ID NOs: 17, 19 to 24, and 33, or a nucleic acid sequence having at least 80% sequence identity to said sequence. In some aspects of the present invention a bi-specific aptamer comprises one of SEQ ID NOs: 18, 37 and 38, or a nucleic acid sequence having at least 80% sequence identity to said sequence. In some aspects of the present invention a bi-specific aptamer comprises a complex of one of one of SEQ ID NOs: 17, 19 to 24, and 33 or a nucleic acid sequence having at least 80% sequence identity to said sequence and one of SEQ ID NOs: 18, 37 and 38 or a nucleic acid sequence having at least 80% sequence identity to said sequence.

In some embodiments one or more bases or nucleotides are chemically modified. In some embodiments one or more nucleotides are chemically modified at the 2' position of ribose. Nucleic acid sequences of the aptamers according to the present invention may be RNA and/or may comprise 2'-fluoro modified pyrimidine and/or may comprise 2'-O-methylated purine.

In another aspect of the present invention a complex, preferably a non-covalent complex, of a bi-specific aptamer and a tumor cell expressing a tumor cell antigen to which the bi-specific aptamer is capable of binding is provided. In another aspect of the present invention a complex, preferably a non-covalent complex, of a bi-specific aptamer and an immune cell expressing an immune cell surface protein to which the bi-specific aptamer is capable of binding is provided. In another aspect of the present invention a complex, preferably a non-covalent complex, of a bi-specific aptamer, a tumor cell expressing a tumor cell antigen to which the bi-specific aptamer is capable of binding and an immune cell expressing an immune cell surface protein to which the bi-specific aptamer is capable of binding is provided. The immune cell may be a T-cell, e.g. CD8+ and/or CD4+ T-cell or cytotoxic T-cell. In some embodiments, the complex is formed in vitro, and is optionally isolated. In other embodiments the complex may be formed in vivo. The complex preferably comprises the bi-specific aptamer bound to one or both of the tumor cell and immune cell. The tumor cell may be of any type of cancer, as described herein. In some embodiments it is a pancreatic cancer cell or glioblastoma cell.

In another aspect of the present invention a pharmaceutical composition comprising a bi-specific aptamer according to the present invention and a pharmaceutically acceptable carrier, diluent or excipient is provided.

In another aspect of the present invention a bi-specific aptamer according to the present invention is provided for use in a method of medical treatment.

In another aspect of the present invention a bi-specific aptamer according to the present invention is provided for use in a method of treatment of cancer.

In another aspect of the present invention the use of a bi-specific aptamer according to the present invention in the manufacture of a medicament for use in a method of medical treatment is provided.

In another aspect of the present invention the use of a bi-specific aptamer according to the present invention in the manufacture of a medicament for use in a method of treatment of cancer is provided.

In another aspect of the present invention a method of treatment of cancer in a subject in need of treatment is provided, the method comprising administering a therapeutically effective amount of a bi-specific aptamer according to the subject.

In some embodiments, the cancer is a pancreatic cancer. In some embodiments the cancer overexpresses at least one of HSP70, vimentin, HSP90, TfR or PDGFR-a.

In another aspect of the present invention a method of selecting a subject for treatment of cancer with a therapeutically effective amount of a bi-specific aptamer according to the present invention is provided, the method comprising determining, in vitro, whether cells of a cancer in the subject overexpress at least one of HSP70, vimentin, HSP90, TfR or PDGFR-a.

In some embodiments the aptamers or bi-specific aptamers according to the present invention are capable of internalising into a cell following binding to a cell surface target molecule. Such aptamers are useful in methods of delivering a compound moiety to the cell, where the compound moiety is conjugated to the aptamer.

Aptamers and bi-specific aptamers according to the present invention may also inhibit proliferation of cells in vitro or in vivo. This may involve inhibition of cancer/tumor cell proliferation. This may be a cytostatic effect, but may also be a cytotoxic effect. As such, aptamers according to the present invention are provided for use in methods of medical treatment where inhibition of cell proliferation is useful for treatment of a disease.

In some embodiments an aptamer, bi-specific aptamer or nucleic acid compound may further comprises a compound moiety covalently attached to said nucleic acid sequence. The compound moiety may be a therapeutic moiety or an imaging moiety.

The therapeutic moiety may be a nucleic acid moiety, an antibody, a peptide moiety or a small molecule drug moiety. The therapeutic moiety is may be an activating nucleic acid moiety or an antisense nucleic acid moiety. The therapeutic moiety may be an miRNA moiety, mRNA moiety, siRNA moiety or an saRNA moiety. The therapeutic moiety may be an siRNA moiety or saRNA moiety. The therapeutic moiety may be an anticancer agent moiety. The therapeutic moiety may be a C/EBPalpha saRNA moiety or a KRAS siRNA moiety. The imaging agent moiety may be a bioluminescent molecule, a photoactive molecule, a metal or a nanoparticle.

BRIEF DESCRIPTION OF THE DRAWINGS

FIG. 10. Nucleic acid sequences of aptamers truncated P19 (tP19), full length P19, P15, P1, P11, P7 and P6 and consensus sequence SEQ ID NO:8. This series of aptamers is described in WO2013/154735. P19 and P1 bind HSP70. P15 binds vimentin. P11, P7 and P6 bind HSP90.

FIG. 11. Nucleic acid sequence of CCR5 aptamers.

FIGS. 12A-12B. Nucleic acid sequence of components of bi-specific aptamer targeting mHSP70 and CCR5. Bi-specific aptamer is a non-covalent complex of sequences depicted in (A) and (B). (FIG. 12A) Nucleic acid sequence of truncated P19 aptamer capable of binding to mHSP70 conjugated to a sticky sequence (bold) with intermediate seven C3 carbon spacer (each C3 carbon represented by "o"). fC and fU indicates 2'-fluoro pyrimidine modification, mA and mG indicates 2'-OMe purine modification. (FIG. 12B) Nucleic acid sequence of CCR5 aptamer conjugated to a sticky sequence (bold) with intermediate five C3 carbon spacer (each C3 carbon represented by "o"). fC and fU indicates 2'-fluoro pyrimidine, mA and mG indicates 2'-O-methylated purine.

FIGS. 14A-14B. Nucleic acid sequence of components of bi-specific aptamer targeting one of mHSP70, vimentin or HSP90 and CCR5. Bi-specific aptamer is a non-covalent complex of one of the sequences depicted in (FIG. 14A) and the sequence depicted in (FIG. 14B). (FIG. 14A) Nucleic acid sequence of (i) full length P19 aptamer capable of binding to mHSP70 conjugated to a sticky sequence (bold) with intermediate seven C3 carbon spacer (each C3 carbon represented by "o"), (ii) P1 aptamer capable of binding to mHSP70 conjugated to a sticky sequence (bold) with intermediate seven C3 carbon spacer (each C3 carbon represented by "o"), (iii) P15 aptamer capable of binding to vimentin conjugated to a sticky sequence (bold) with intermediate seven C3 carbon spacer (each C3 carbon represented by "o"), (iv) P11 aptamer capable of binding to HSP90 conjugated to a sticky sequence (bold) with intermediate seven C3 carbon spacer (each C3 carbon represented by "o"), (v) P7 aptamer capable of binding to HSP90 conjugated to a sticky sequence (bold) with intermediate seven C3 carbon spacer (each C3 carbon represented by "o"), (vi) P6 aptamer capable of binding to HSP90 conjugated to a sticky sequence (bold) with intermediate seven C3 carbon spacer (each C3 carbon represented by "o"); (FIG. 14B) Nucleic acid sequence of CCR5 aptamer conjugated to a sticky sequence (bold) with intermediate five C3 carbon spacer (each C3 carbon represented by "o"). fC and fU indicates 2'-fluoro pyrimidine, mA and mG indicates 2'-O-methylated purine.

(FIG. 17A) P15 was selected from randomized N40 RNA libraries. The secondary structure was predicted using the NUPACK software. (FIG. 17B and FIG. 17C) Cy3-labeled P19 and P1 aptamers (200 nM) were assessed for binding efficiency by flow cytometry in PANC-1 and control Huh7 cells. The data show the percentage of positively stained cells from triplicate experiments. The error bars represent the standard deviation (STD). Huh7 CC (Huh7 unstained cell control), PANC-1 CC (PANC-1 unstained cell control), Huh7 Lib (Huh 7 staining control with a Cy3-labeled library), PANC-1 Lib (PANC-1 staining control with a Cy3-labeled library), Huh7 P15 (Huh7 stained with P15), PANC-1 P15 (PANC-1 stained with P15). Student's t test **: P<0.01. (FIG. 17D) The dissociation constant ($K_D$) was measured by flow cytometry using increasing concentrations of Cy3-labeled aptamers (from 15.6 to 500 nM). The mean fluorescence intensity (MFI) was measured and calculated using a one-site binding model for non-linear regression.

FIGS. 19A-19C. Tandem MS/MS spectra. (FIG. 19A) Polyacrylamide gel electrophoresis (SDS-PAGE) was used to separate immobilized protein samples after pulldown with biotinylated P15 and irrelevant RNAs. Shown are Coomassie-stained gels M (Marker), total cell lysate (lane 1), P15 (lane 2), NC (irrelevant RNA, lane 3). Arrow indicated the target. (FIG. 19B) Peptide matching and MS/MS spectrum of P15 affinity-purified peptides. Inset: Amino acid sequence of the parent peptide showing b- and y-ion series coverage. The target epitope was highlighted in yellow. Sequence: SEQ ID NO:40. (FIG. 19C) The aptamer-antibody competition assay was employed to validate the target. The Cy3-labeled P15 aptamer was used to compete with vimentin antibodies. The fluorescence intensity was quantified (AU: arbitrary units). Student's t test *: P<0.05.

FIG. 20. Nucleic acid sequence of TfR aptamers.

FIG. 21. Nucleic acid sequence of PDGF-a aptamers.

FIGS. 24A-24B. Binding assay with CD3ε aptamer C3e2 and HEK cell lines stably expressing EGFP-CD3ε fusion proteins. (FIG. 24A) Aptamer C3e2 binds HEK cells expressing human CD3ε. Visualization: Red channel (Cy3-labeled aptamer C3e2 (100 nM)); Green channel (EGFP-human CD3ε); Blue channel (Hoechst 33342). (FIG. 24B) Aptamer C3e2 binds HEK cells expressing mouse CD3ε. Visualization: Red channel (Cy3-labeled aptamer C3e2 (100 nM)); Green channel (EGFP-mouse CD3ε); Blue channel (Hoechst 33342). The scale bar on the lower right hand corner of each image represents 10 microns.

FIGS. 25A-25B. Binding assay with CD3ε aptamer C3e3 and HEK cell lines stably expressing EGFP-CD3ε fusion proteins. (FIG. 25A) Aptamer C3e3 binds HEK cells expressing human CD3ε. Visualization: Red channel (Cy3-labeled aptamer C3e3 (100 nM)); Green channel (EGFP-human CD3€); Blue channel (Hoechst 33342). (FIG. 25B) Aptamer C3e3 binds HEK cells expressing mouse CD3ε. Visualization: Red channel (Cy3-labeled aptamer C3e3 (100 nM)); Green channel (EGFP-mouse CD3€); Blue channel (Hoechst 33342). The scale bar on the lower right hand corner of each image represents 10 microns.

(FIG. 26A) Human T cells ($1 \times 10^5$ cells/mL) were incubated with 500 nM of Cy3-labeled aptamer C3e2. After washing, flow cytometry analysis was performed. The histogram shift indicates strong binding by C3e2. (FIG. 26B) Human T cells ($1 \times 10^5$ cells/mL) were incubated with 500 nM of Cy3-labeled aptamer C3e3. After washing, flow cytometry analysis was performed. The histogram shift indicates strong binding by C3e3.

DETAILED DESCRIPTION OF THE INVENTION

Definitions

Figure 1:
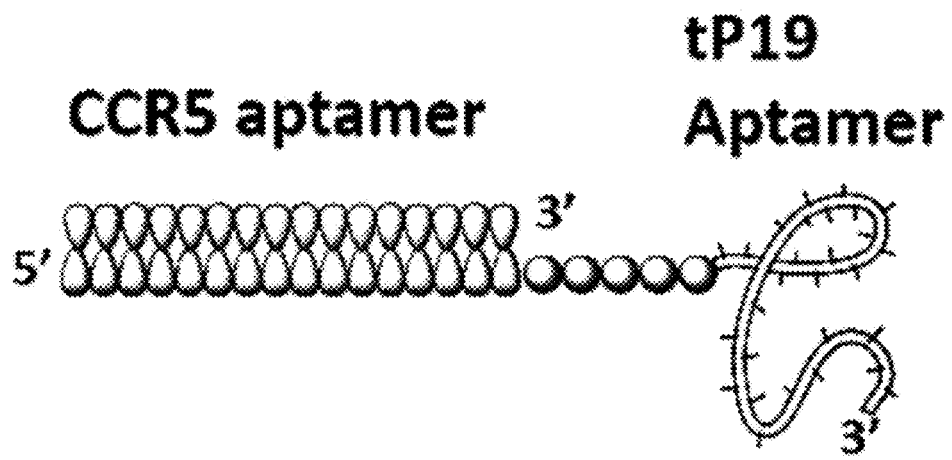
FIG. 1. Diagram illustrating bi-specific aptamer comprising CCR5 aptamer, spacer and tP19 aptamer.
Figure 2:
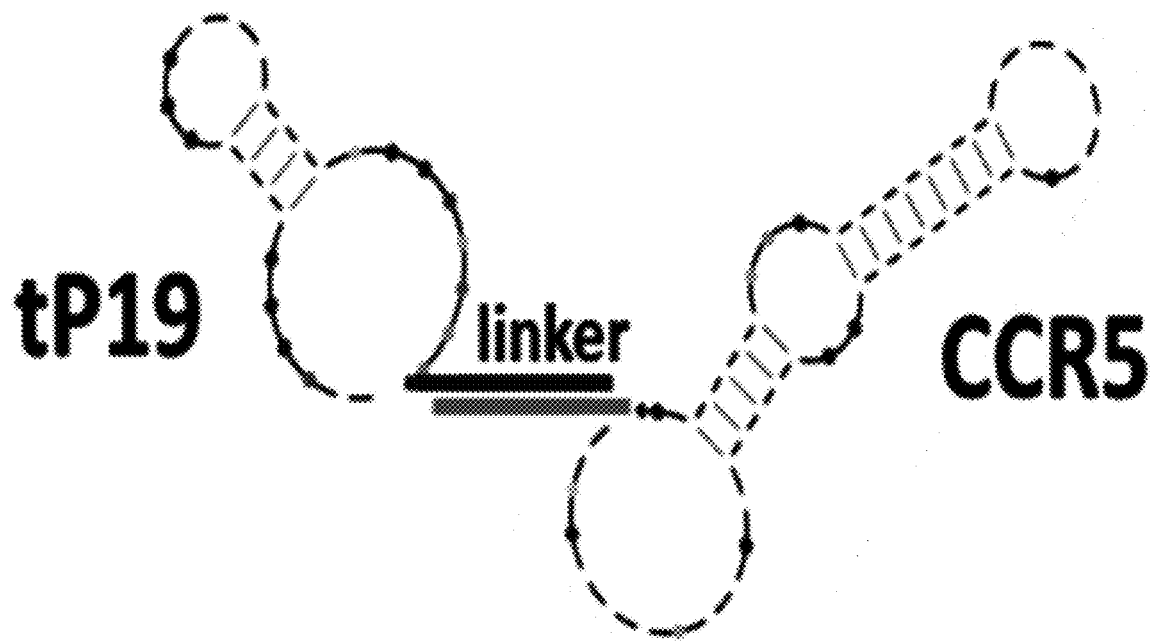
FIG. 2. Diagram illustrating linkage of tP19 and CCR5 aptamer using 'sticky end' complementary nucleic acid sequences.
Figure 3:
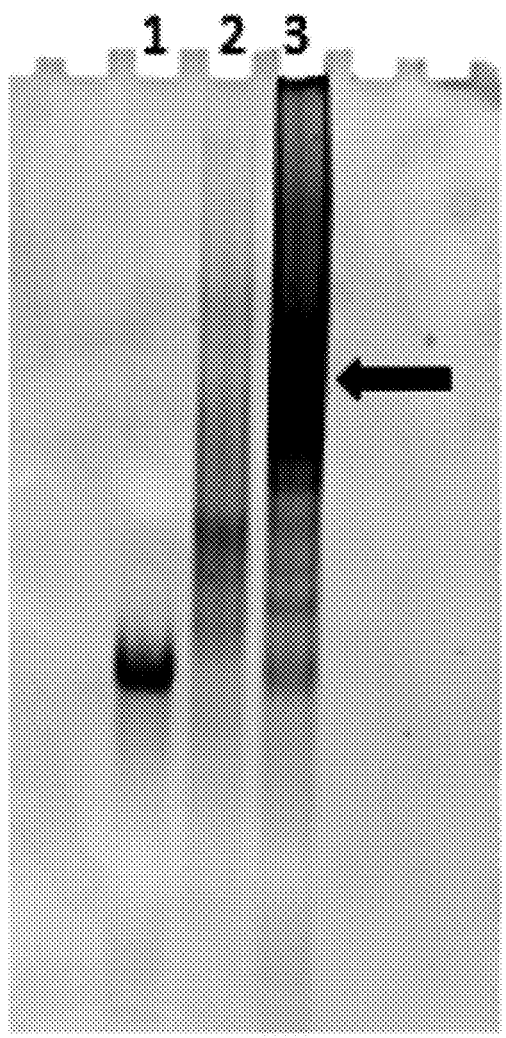
FIG. 3. Photograph showing isolation of tP19 aptamer, CCR5 aptamer and tP19-CCR5 bi-specific aptamer by gel electrophoresis.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Unless defined otherwise, technical and scientific terms used herein have the same meaning as commonly understood by a person of ordinary skill in the art. See, e.g., Singleton et al., Dictionary of Microbiology and Molecular Biology 2nd ed., J. Wiley & Sons (New York, NY 1994); Sambrook et al., Molecular Clonging, A Laboratory Manual, Cold Springs Harbor Press (Cold Springs Harbor, N Y 1989).

Any methods, devices and materials similar or equivalent to those described herein can be used in the practice of this invention. The following definitions are provided to facilitate understanding of certain terms used frequently herein and are not meant to limit the scope of the present disclosure.

The abbreviations used herein have their conventional meaning within the chemical and biological arts. The chemical structures and formulae set forth herein are constructed according to the standard rules of chemical valency known in the chemical arts.

"Nucleic acid" refers to deoxyribonucleotides or ribonucleotides and polymers thereof in either single-, double- or multiple-stranded form, or complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including nucleic acids with a phosphothioate backbone can include one or more reactive moieties. As used herein, the term reactive moiety includes any group capable of reacting with another molecule, e.g., a nucleic acid or polypeptide through covalent, noncovalent or other interactions. By way of example, the nucleic acid can include an amino acid reactive moiety that reacts with an amino acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate), phosphorodithioate, phosphonocarboxylic acids, phosphonocarboxylates, phosphonoacetic acid, phosphonoformicacid, methyl phosphonate, boron phosphonate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The term "aptamer" as provided herein refers to oligonucleotides (e.g. short oligonucleotides or deoxyribonucleotides), that bind (e.g. with high affinity and specificity) to proteins, peptides, and small molecules. An aptamer may be referred to as an oligonucleotide based target binding moiety. Aptamers may be RNA or DNA. Aptamers may have secondary or tertiary structure and, thus, may be able to fold into diverse and intricate molecular structures.

Aptamers can be selected in vitro from very large libraries of randomized sequences by the process of systemic evolution of ligands by exponential enrichment (SELEX as described in Ellington A D, Szostak J W (1990) In vitro selection of RNA molecules that bind specific ligands. Nature 346:818-822; Tuerk C, Gold L (1990) Systematic evolution of ligands by exponential enrichment: RNA ligands to bacteriophage T4 DNA polymerase. Science 249:505-510) or by developing SOMAmers (slow off-rate modified aptamers) (Gold L et al. (2010) Aptamer-based multiplexed proteomic technology for biomarker discovery. PLOS ONE 5(12):e15004). Applying the SELEX and the SOMAmer technology includes for instance adding functional groups that mimic amino acid side chains to expand the aptamer's chemical diversity. As a result high affinity aptamers for a protein may be enriched and identified. Aptamers may exhibit many desirable properties for targeted drug delivery, such as ease of selection and synthesis, high binding affinity and specificity, low immunogenicity, and versatile synthetic accessibility. Anticancer agents (e.g. chemotherapy drugs, toxins, and siRNAs) may be successfully delivered to cancer cells in vitro using aptamers.

Aptamers are nucleic acid molecules characterised by the ability to bind to a target molecule with high specificity and high affinity. Almost every aptamer identified to date is a non-naturally occurring molecule.

Aptamers may be DNA or RNA molecules and may be single stranded or double stranded. The aptamer may comprise chemically modified nucleotides or nucleosides, for example in which the sugar and/or phosphate and/or base is chemically modified. Such modifications may improve the stability of the aptamer or make the aptamer more resistant to degradation. The aptamers of the present invention may include chemical modifications as described herein such as a chemical substitution at a sugar position, a phosphate position, and/or a base position of the nucleic acid including, for example, incorporation of a modified nucleotide, incorporation of a capping moiety (e.g. 3' capping), conjugation to a high molecular weight, non-immunogenic compound (e.g. polyethylene glycol (PEG)), conjugation to a lipophilic compound, substitutions in the phosphate backbone. Base modifications may include 5-position pyrimidine modifications, modifications at exocyclic amines, substitution of 4-thiouridine, substitution of 5-bromo- or 5-iodo-uracil, backbone modifications. Sugar modifications may include 2'-amine nucleotides (2'-NH$_2$), 2'-fluoro nucleotides (2'-F), and 2'-O-methyl (2'-OMe) nucleotides. A wide range of nucleotide, nucleoside, base and phosphate modifications are known to those or ordinary skill in the art, e.g. as described in Eaton et al., Bioorganic & Medicinal Chemistry, Vol. 5, No. 6, pp 1087-1096, 1997.

Aptamers may be synthesised by methods which are well known to the skilled person. For example, aptamers may be chemically synthesised, e.g. on a solid support. Solid phase synthesis may use phosphoramidite chemistry. Briefly, a solid supported nucleotide is detritylated, then coupled with a suitably activated nucleoside phosphoramidite to form a phosphite triester linkage. Capping may then occur, followed by oxidation of the phosphite triester with an oxidant, typically iodine. The cycle may then be repeated to assemble the aptamer (e.g., see Sinha, N. D.; Biernat, J.; McManus, J.; Köster, H. Nucleic Acids Res. 1984, 12, 4539; and Beaucage, S. L.; Lyer, R. P. (1992). *Tetrahedron* 48 (12): 2223).

Aptamers can be thought of as the nucleic acid equivalent of monoclonal antibodies and often have $K_d$'s in the nM or pM range, e.g. less than one of 500 nM, 100 nM, 50 nM, 10 nM, 1 nM, 500 pM, 100 pM. As with monoclonal antibodies, they may be useful in virtually any situation in which target binding is required, including use in therapeutic and diagnostic applications, in vitro or in vivo. In vitro diagnostic applications may include use in detecting the presence or absence of a target molecule.

Aptamers according to the present invention may be provided in purified or isolated form. Aptamers according to the present invention may be formulated as a pharmaceutical composition or medicament.

A "tumor cell antigen aptamer" is an aptamer that has high affinity and specificity for a tumor cell antigen, as defined herein. WO2013/154735 and FIG. 10 describe the pancreatic cancer cell binding aptamers P19, P15, P1, P11, P7, P6 and the consensus sequence SEQ ID NO:8. The sequence of a truncated P19 aptamer is shown in FIG. 10.

In some embodiments the tumor cell antigen aptamer is a HSP70 binding aptamer. HSP70 binding aptamers such as P19, tP19 and P1 are described in WO2013/154735 and in U.S. provisional patent application No. 62/141,156, incorporated herein by reference.

In some embodiments the tumor cell antigen aptamer is a vimentin binding aptamer. Vimentin binding aptamers such as P15 are described in WO2013/154735, incorporated herein by reference.

In some embodiments the tumor cell antigen aptamer is a HSP90 binding aptamer. HSP90 binding aptamers such as P11, P7 and P6 are described in WO2013/154735, incorporated herein by reference.

Pancreatic cancer cell binding aptamers, including HSP70, vimentin and HSP90 binding aptamers, include aptamers comprising a nucleic acid sequence according to one of SEQ ID NOs 1 to 8, or an aptamer having a nucleic acid sequence having a degree of primary sequence identity of at least 80% to one of SEQ ID NOs 1 to 8. In some embodiments a pancreatic cancer cell, HSP70, vimentin or HSP90 binding aptamer may have a nucleic acid sequence consisting of one of SEQ ID NOs 1 to 8. In a bi-specific aptamer according to the present invention the pancreatic cancer cell, HSP70, vimentin or HSP90 binding part, e.g. excluding any linker or spacer nucleic acid sequence or sticky bridge may have a nucleic acid sequence comprising or consisting of one of SEQ ID NOs 1 to 8 as described above and herein.

In some embodiments the tumor cell antigen aptamer is a transferrin receptor (TfR) binding aptamer. TfR binding aptamers such as TR14 and TR18 (shown in FIG. 20) are described in PCT/US15/55792, incorporated herein by reference.

TfR binding aptamers include aptamers comprising a nucleic acid sequence according to one of SEQ ID NOs 28 to 30, or an aptamer having a nucleic acid sequence having a degree of primary sequence identity of at least 80% to one of SEQ ID NOs: 28 to 30. In some embodiments a TfR binding aptamer may have a nucleic acid sequence consisting of one of SEQ ID NOs: 28 to 30. In a bi-specific aptamer according to the present invention the TfR binding part, e.g. excluding any linker or spacer nucleic acid sequence or sticky bridge may have a nucleic acid sequence comprising or consisting of one of SEQ ID Nos: 28 to 30 as described above and herein.

In some embodiments the tumor cell antigen aptamer is an alpha-type platelet-derived growth factor receptor (PDGFR-a) binding aptamer. PDGFR-a binding aptamers such as PDR3 and PDR9 (shown in FIG. 21) are described in PCT/US15/55815, incorporated herein by reference.

PDGFR-a binding aptamers include aptamers comprising a nucleic acid sequence according to one of SEQ ID NOs: 31 and 32, or an aptamer having a nucleic acid sequence having a degree of primary sequence identity of at least 80% to one of SEQ ID NOs: 31 and 32. In some embodiments a PDGFR-a binding aptamer may have a nucleic acid sequence consisting of one of SEQ ID NOs: 31 and 32. In a bi-specific aptamer according to the present invention the PDGFR-a binding part, e.g. excluding any linker or spacer nucleic acid sequence or sticky bridge may have a nucleic acid sequence comprising or consisting of one of SEQ ID NOs: 31 and 32 as described above and herein.

An "immune cell surface protein aptamer" is an aptamer that has high affinity and specificity for an immune cell surface protein, as defined herein.

In some embodiments the immune cell surface protein aptamer is a CCR5 binding aptamer. CCR5 binding aptamers are described in Zhou et al., 2015, Chemistry & Biology 22, 379-390 Mar. 19, 2015 and in co-pending U.S. patent application Ser. No. 14/801,710, each specifically incorporated herein by reference. CCR5 binding aptamers include aptamers comprising a nucleic acid sequence according to one of SEQ ID NOs 9 to 16, or an aptamer having a nucleic acid sequence having a degree of primary sequence identity of at least 80% to one of SEQ ID NOs 9 to 16. In some embodiments a CCR5 binding aptamer may have a nucleic acid sequence consisting of one of SEQ ID NOs 9 to 16. In some embodiments each pyrimidine is a 2'fluoropyrimidine. In a bi-specific aptamer according to the present invention the CCR5 binding part, e.g. excluding any linker or spacer nucleic acid sequence or sticky bridge may have a nucleic acid sequence comprising or consisting of one of SEQ ID NOs 9 to 16 as described above and herein.

In some embodiments the immune cell surface protein aptamer is a CCR7 binding aptamer.

In some embodiments the immune cell surface protein aptamer is a CD2 binding aptamer.

In some embodiments the immune cell surface protein aptamer is a CD3 binding aptamer. CD3 binding aptamers include aptamers comprising a nucleic acid sequence according to one of SEQ ID NOs 37 and 38, or an aptamer having a nucleic acid sequence having a degree of primary sequence identity of at least 80% to one of SEQ ID NOs 37 and 38. In some embodiments a CD3 binding aptamer may have a nucleic acid sequence consisting of one of SEQ ID NOs 37 and 38. In some embodiments each pyrimidine is a 2'fluoropyrimidine. In a bi-specific aptamer according to the present invention the CD3 binding part, e.g. excluding any linker or spacer nucleic acid sequence or sticky bridge may have a nucleic acid sequence comprising or consisting of one of SEQ ID NOs 37 and 38 as described above and herein. In embodiment, a CD3 binding aptamer includes an aptamer comprising a nucleic acid sequence of SEQ ID NO: 34 or 35, including a linker or spacer nucleic acid sequence or sticky bridge.

In some embodiments the immune cell surface protein aptamer is a CD4 binding aptamer. CD4 binding aptamers are described in Zhou, Qing et al. "Aptamer-Containing Surfaces for Selective Capture of CD4 Expressing Cells." *Langmuir: the ACS journal of surfaces and colloids* 28.34 (2012): 12544-12549. PMC. Web. 8 Feb. 2016; Zhang et al., American Journal of Clinical Pathology, Volume 134, Issue 4, 1 Oct. 2010; Wheeler et al., *J Clin Invest.* 2011; 121(6): 2401-2412, each specifically incorporated herein by reference.

In some embodiments the immune cell surface protein aptamer is a CD7 binding aptamer. CD7 binding aptamers are described in WO2014/147559, specifically incorporated herein by reference.

In some embodiments the immune cell surface protein aptamer is a CD8 binding aptamer. CD8 binding aptamers are described in Wang et al., J Allergy Clin Immunol. 2013 September; 132(3):713-722; Oelkrug, C., Sack, U., Boldt, A., Nascimento, I. C., Ulrich, H. and Fricke, S. (2015), Antibody- and aptamer-strategies for GVHD prevention. Journal of Cellular and Molecular Medicine, 19: 11-20, each specifically incorporated herein by reference.

In some embodiments the immune cell surface protein aptamer is a PD-1 binding aptamer. PD-1 binding aptamers are described in, Prodeus et al Molecular Therapy Nucleic Acids (2015) 4 e237, Ti-Hsuan Ku Sensors 2015, 15, 16281-16313, and WO2016/019270, each specifically incorporated herein by reference.

In some embodiments the immune cell surface protein aptamer is a CTLA4 binding aptamer. CTLA4 binding aptamers are described in Herrmann et al., *J Clin Invest.* 2014; 124(7):2977-2987, Gilboa et al., Clin Cancer Res; 19(5); 1054-62, and Santulli-Marotto et al., Cancer Res. 2003 Nov. 1; 63(21):7483-9, each specifically incorporated herein by reference.

Aptamers are normally mono-specific, i.e. having high affinity and specificity for a single target molecule.

The nucleic acid sequence of a mono-specific aptamer, or mono-specific part of a bi-specific aptamer, according to the present invention may optionally have a minimum length of one of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides The nucleic acid sequence of a mono-specific aptamer, or mono-specific part of a bi-specific aptamer, according to the present invention may optionally have a maximum length of one of 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

The nucleic acid sequence of a mono-specific aptamer, or mono-specific part of a bi-specific aptamer, according to the present invention may optionally have a length of one of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

The nucleic acid sequence of a mono-specific aptamer or mono-specific part of a bi-specific aptamer (including when present in a bi-specific aptamer complex), according to the present invention may have a degree of primary sequence identity with one of SEQ ID NOs 1 to 24 or 28 to 32, that is at least one of 80%, 81%, 82%, 83%, 84%, 85%, 86%, 87%, 88%, 89%, 90%, 91%, 92%, 93%, 94%, 95%, 96%, 97%, 98%, 99%, or 100%.

A "bi-specific aptamer" is an aptamer based compound or composition that has high affinity and specificity for two, or at least two, different target molecules. A bi-specific aptamer may be comprised of the nucleic acid sequence of two mono-specific aptamers. A bi-specific aptamer may be a complex or conjugate of two mono-specific aptamers. The nucleic acid sequences of the two mono-specific aptamers may be brought together to form a complex, which may be a covalent or non-covalent complex. In some embodiments the bi-specific aptamer may comprise the nucleic acid sequence of a tumor cell antigen aptamer in complex with the nucleic acid sequence of an immune cell surface protein aptamer.

As such, a bi-specific aptamer may be a complex of a tumor cell antigen binding moiety and an immune cell surface protein binding moiety.

A covalent complex may be provided by forming a covalent bond between members of the complex. In some embodiments a bi-specific aptamer may be formed by synthesizing a single oligonucleotide molecule that comprises the nucleic acid sequence of a first mono-specific aptamer followed by the nucleic acid sequence of a second mono-specific aptamer, optionally with a linker between the two sequences. The linker may comprise one or more of an oligonucleotide sequence, hydrocarbon spacer elements such as optionally substituted $C_{1-30}$ alkyl or optionally substituted $C_{2-30}$ alkenyl; or polyethylene glycol molecule(s). In some embodiments the linker may be a polycarbon linker, consistent with formation of a "sticky bridge". The polycarbon linker may be an optionally substituted C10-30 alkyl, optionally substituted C10-15 alkyl, optionally substituted C15-20 alkyl, optionally substituted C20-25 alkyl, optionally substituted C25-30 alkyl, optionally substituted C10-30 alkenyl, optionally substituted C10-15 alkenyl, optionally substituted C15-20 alkenyl, optionally substituted C20-25 alkenyl, optionally substituted C25-30 alkenyl.

A non-covalent complex may be provided by forming one or more non-covalent bonds between members of the complex. Non-covalent complexes may be maintained by hydrogen bonding, van der Waal forces and optionally ionic interaction. In some embodiments a bi-specific aptamer may be formed by attaching one of a pair of linker moieties to the nucleic acid sequence of each of two mono-specific aptamers, where the linker moieties have affinity or complementarity for each other, and allowing the linker moieties to bind and form a non-covalent complex. Examples of suitable linker moieties include a pair of single stranded oligonucleotides having complementary sequences that permit hybridization or tag and capture element pairs such as biotin and avidin/strepavidin.

As used herein, the term "conjugate," "bioconjugate" or "bioconjugate reactive group" or "bioconjugate linker" refers to the association between atoms or molecules. The association can be direct or indirect. For example, a conjugate between a first moiety (e.g. —$NH_2$, COOH, —N-hydroxysuccinimide, or -maleimide) and a second moiety (e.g., sulfhydryl, sulfur-containing amino acid) provided herein can be direct, e.g., by covalent bond or linker, or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, Advanced Organic Chemistry, 3rd Ed., John Wiley & Sons, New York, 1985; Hermanson, Bioconjugate Techniques, Academic Press, San Diego, 1996; and Feeney et al., Modification of Proteins; Advances in Chemistry Series, Vol. 198, American Chemical Society, Washington, D.C., 1982. In embodiments, the first moiety (e.g., a tumor cell antigen binding moiety) is non-covalently attached to the second moiety on the immune cell surface protein binding moiety through a non-covalent chemical linker or covalent chemical linker formed by a reaction between a component of the first moiety and a component of the second moiety. In embodiments, the first moiety (e.g., a tumor cell antigen binding moiety) includes one or more reactive moieties, e.g., a covalent reactive moiety, as described herein (e.g., alkyne, azide, amine, ester, N-hydroxy-succinimide, maleimide or thiol reactive moiety). In embodiments, the first moiety (e.g., a tumor cell antigen binding moiety) includes a linker (e.g., first linker) with one or more reactive moieties, e.g., a covalent reactive moiety, as described herein (e.g., alkyne, azide, amine, ester, N-hydroxy-succinimide, maleimide or thiol reactive moiety). In embodiments, the second moiety (e.g., an immune cell surface protein binding moiety) includes one or more reactive moieties, e.g., a covalent reactive moiety, as described herein (e.g., alkyne, azide, amine, ester, N-hydroxy-succinimide, maleimide or thiol reactive moiety). In embodiments, the second moiety (e.g., an immune cell surface protein binding moiety) includes a linker with one or more reactive moieties, e.g., a covalent reactive moiety, as described herein (e.g., alkyne, azide, amine, ester, N-hydroxy-succinimide, maleimide or thiol reactive moiety).

Useful reactive moieties or functional groups used for conjugate chemistries herein include, for example: (a) carboxyl groups and various derivatives thereof including, but not limited to, Nhydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc. (c) halo alkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold; (h) amine or sulfhydryl groups, which can be, for example, acylated, alkylated or oxidized; (i) alkenes, which can undergo, for example, cycloadditions, acylation, Michael addition, etc; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g. phosphines) to form, for example, phosphate diester bonds; and (n) sulfones, for example, vinyl sulfone.

The reactive functional groups can be chosen such that they do not participate in, or interfere with, the chemical stability of the proteins described herein. By way of example, the nucleic acids can include a vinyl sulfone or other reactive moiety. Optionally, the nucleic acids can include a reactive moiety having the formula S—S—R. R can be, for example, a protecting group. Optionally, R is hexanol. As used herein, the term hexanol includes compounds with the formula C6H130H and includes, 1-hexanol, 2-hexanol, 3-hexanol, 2-methyl-1-pentanol, 3-methyl-1-pentanol, 4-methyl-1-pentanol, 2-methyl-2-pentanol, 3-methyl-2-pentanol, 4-methyl-2-pentanol, 2-methyl-3-pentanol, 3-methyl-3-pentanol, 2,2-dimethyl-1-butanol, 2,3-dimethyl-1-butanol, 3,3-dimethyl-1-butanol, 2,3-dimethyl-2-butanol, 3,3-dimethyl-2-butanol, and 2-ethyl-1-butanol. Optionally, R is 1-hexanol.

Figures 15, 16:
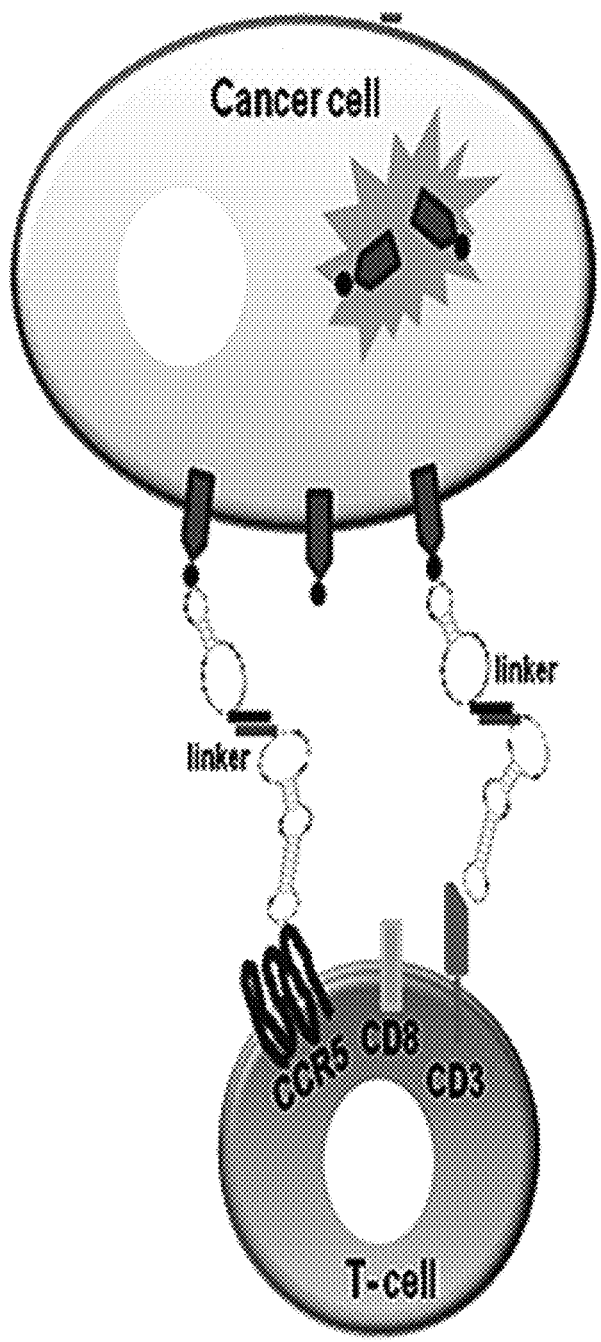
FIG. 15. Sticky end (SE) sequences. A pair of complementary SE sequences are used to form the bi-specific aptamer complex. SE 1 is conjugated to the 3' or 5' end of one aptamer and one or SE2 or SE3 is conjugated to the 3' or 5' end of the other aptamer. Aptamer-SE conjugates are mixed and allowed to form a bi-specific aptamer complex. SE1 [SEQ ID NO: 25]. SE2 [SEQ ID NO: 26] complementary to SE1 3'-5'. SE3 [SEQ ID NO: 27] complementary to SE1 5'-3'.
FIG. 16. Diagram illustrating immunological synapse formed by bi-specific aptamers with a target cancer cell and T-cell.

In embodiments, oligonucleotides, including aptamers, antisense nucleic acids etc, may be formed into a non-covalent complex through the use of a "sticky bridge". A sticky bridge comprises an oligonucleotide ("sticky sequence" or "sticky end") positioned at the 3'- or 5'-end of a first aptamer oligonucleotide sequence. A complementary oligonucleotide ("sticky sequence" or "sticky end") is positioned at the 3'- or 5'-end of a second, preferably different, aptamer oligonucleotide sequence. The complementary sticky sequences are allowed to hybridise and form a non-covalent complex comprising the first and second aptamers. The sticky sequence may be GC or AU rich, and each sticky sequence may comprise about 16 nucleotides, e.g. 14 to 20 nucleotides or one of 14, 15, 16, 17, 18, 19 or 20 nucleotides. Examples of complementary pairs of sticky sequences are SEQ ID NOs: 25 and 26 or SEQ ID NOs: 25 and 27 (FIG. 15).

A polycarbon linker may be incorporated between the sticky sequence and aptamer oligonucleotide sequence. The polycarbon linker provides rigidity to the aptamer, decreasing the likelihood that the inclusion of the additional sticky sequences will interfere with proper aptamer folding (e.g. see Zhou J, Swiderski P, Li H, et al. Selection, characterization and application of new RNA HIV gp 120 aptamers for facile delivery of Dicer substrate siRNAs into HIV infected cells. Nucleic Acids Res. 2009; 37(9):3094-3109).

The polycarbon linker may comprise one or more of an oligonucleotide sequence, hydrocarbon spacer elements such as optionally substituted $C_{1-30}$ alkyl or optionally substituted $C_{2-30}$ alkenyl; or polyethylene glycol molecule(s). In some embodiments the polycarbon linker may be a polycarbon linker, consistent with formation of a "sticky bridge." The polycarbon linker may be an optionally substituted $C_{10-30}$ alkyl, optionally substituted $C_{10-15}$ alkyl, optionally substituted $C_{15-20}$ alkyl, optionally substituted $C_{20-25}$ alkyl, optionally substituted $C_{25-30}$ alkyl, optionally substituted $C_{10-30}$ alkenyl, optionally substituted $C_{10-15}$ alkenyl, optionally substituted $C_{15-20}$ alkenyl, optionally substituted $C_{20-25}$ alkenyl, optionally substituted $C_{25-30}$ alkenyl.

Accordingly, a bispecific aptamer according to the present invention may comprise a first aptamer component, e.g. comprising one of SEQ ID NOS: 1 to 8, 28 to 32, covalently conjugated at the 3' or 5' end to a sticky end sequence, e.g. one of SEQ ID NOS:25 to 27, optionally via a polycarbon linker spacer, complexed with a second aptamer component, e.g. comprising one of SEQ ID NOS:9 to 16, covalently conjugated at the 3' or 5' end to a complementary sticky end sequence, e.g. one of SEQ ID NOS:25 to 27, optionally via a polycarbon linker spacer.

The length of a bi-specific aptamer will reflect the length of the nucleic acid sequence of each mono-specific aptamer incorporated in the bi-specific aptamer, and optionally the length of any linker that is included.

A bi-specific aptamer may therefore be defined as a complex of a first mono-specific aptamer having a defined length and degree of primary sequence identity to one of SEQ ID NOS: 1 to 8 or 28 to 32 and a second mono-specific aptamer having a defined length and degree of primary sequence identity to one of SEQ ID NOS:9 to 16. In embodiments the first mono-specific aptamer is a tumor cell antigen aptamer and the second mono-specific aptamer is an immune cell surface protein aptamer.

An "antisense nucleic acid" as referred to herein is a nucleic acid (e.g. DNA or RNA molecule) that is complementary to at least a portion of a specific target nucleic acid (e.g. an mRNA translatable into a protein) and is capable of reducing transcription of the target nucleic acid (e.g. mRNA from DNA) or reducing the translation of the target nucleic acid (e.g. mRNA) or altering transcript splicing (e.g. single stranded morpholino oligo). See, e.g., Weintraub, Scientific American, 262:40 (1990). Typically, synthetic antisense nucleic acids (e.g. oligonucleotides) are generally between 15 and 25 bases in length. Thus, antisense nucleic acids are capable of hybridizing to (e.g. selectively hybridizing to) a target nucleic acid (e.g. target mRNA). In embodiments, the antisense nucleic acid hybridizes to the target nucleic acid sequence (e.g. mRNA) under stringent hybridization conditions. In embodiments, the antisense nucleic acid hybridizes to the target nucleic acid (e.g. mRNA) under moderately stringent hybridization conditions. Antisense nucleic acids may comprise naturally occurring nucleotides or modified nucleotides such as, e.g., phosphorothioate, methylphosphonate, and -anomeric sugar-phosphate, backbone modified nucleotides.

In the cell, the antisense nucleic acids hybridize to the corresponding mRNA, forming a double-stranded molecule. The antisense nucleic acids interfere with the translation of the mRNA, since the cell will not translate an mRNA that is double-stranded. The use of antisense methods to inhibit the in vitro translation of genes is well known in the art (Marcus-Sakura, Anal. Biochem., 172:289, (1988)). Further, antisense molecules which bind directly to the DNA may be used. Antisense nucleic acids may be single or double stranded nucleic acids. Non-limiting examples of antisense nucleic acids include siRNAs (including their derivatives or pre-cursors, such as nucleotide analogs), short hairpin RNAs (shRNA), micro RNAs (miRNA), saRNAs (small activating RNAs) and small nucleolar RNAs (snoRNA) or certain of their derivatives or precursors.

A "siRNA," "small interfering RNA," "small RNA," or "RNAi" as provided herein, refers to a nucleic acid that forms a double stranded RNA, which double stranded RNA has the ability to reduce or inhibit expression of a gene or target gene when present in the same cell as the gene or target gene. The complementary portions of the nucleic acid that hybridize to form the double stranded molecule typically have substantial or complete identity. In one embodiment, a siRNA or RNAi is a nucleic acid that has substantial or complete identity to a target gene and forms a double stranded siRNA. In embodiments, the siRNA inhibits gene expression by interacting with a complementary cellular mRNA thereby interfering with the expression of the complementary mRNA. Typically, the nucleic acid is at least about 15-50 nucleotides in length (e.g., each complementary sequence of the double stranded siRNA is 15-50 nucleotides in length, and the double stranded siRNA is about 15-50 base pairs in length). In other embodiments, the length is 20-30 base nucleotides, preferably about 20-25 or about 24-29 nucleotides in length, e.g., 20, 21, 22, 23, 24, 25, 26, 27, 28, 29, or 30 nucleotides in length.

A "saRNA," or "small activating RNA" as provided herein refers to a nucleic acid that forms a double stranded RNA, which double stranded RNA has the ability to increase or activate expression of a gene or target gene when present in the same cell as the gene or target gene. The complementary portions of the nucleic acid that hybridize to form the double stranded molecule typically have substantial or complete identity. In one embodiment, a saRNA is a nucleic acid that has substantial or complete identity to a target gene and forms a double stranded saRNA. Typically, the nucleic acid is at least about 15-50 nucleotides in length (e.g., each complementary sequence of the double stranded saRNA is 15-50 nucleotides in length, and the double stranded saRNA is about 15-50 base pairs in length). In other embodiments, the length is 20-30 base nucleotides, preferably about 20-25 or about 24-29 nucleotides in length, e.g., 20, 21, 22, 23, 24, 25, 26, 27, 28, 29, or 30 nucleotides in length.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "purified" denotes that a nucleic acid or protein gives rise to essentially one band in an electrophoretic gel. In some embodiments, the nucleic acid or protein is at least 50% pure, optionally at least 65% pure, optionally at least 75% pure, optionally at least 85% pure, optionally at least 95% pure, and optionally at least 99% pure.

The term "isolated" may also refer to a cell or sample cells. An isolated cell or sample cells are a single cell type that is substantially free of many of the components which normally accompany the cells when they are in their native state or when they are initially removed from their native state. In certain embodiments, an isolated cell sample retains those components from its natural state that are required to maintain the cell in a desired state. In some embodiments, an isolated (e.g. purified, separated) cell or isolated cells are cells that are substantially the only cell type in a sample. A purified cell sample may contain at least 60%, 70%, 75%, 80%, 85%, 90%, 95%, 96%, 97%, 98%, 99%, or 100% of one type of cell. An isolated cell sample may be obtained through the use of a cell marker or a combination of cell markers, either of which is unique to one cell type in an unpurified cell sample. In some embodiments, the cells are isolated through the use of a cell sorter. In some embodiments, antibodies against cell proteins are used to isolate cells.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol 215:403-410 (1990), respectively.

For specific proteins described herein (e.g., mHSP70), the named protein includes any of the protein's naturally occurring forms, variants or homologs (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference, homolog or functional fragment thereof.

The term "tumor cell antigen" refers to any protein, carbohydrate or other component that is abnormally expressed by a tumor cell or is expressed by a tumor cell with an abnormal structure. A tumor cell antigen may be expressed at the cell surface by tumor/cancer cells of the tumor/cancer concerned. A tumor cell antigen may optionally be capable of eliciting an immune response. A tumor cell antigen may be a protein, carbohydrate or other component that is normally expressed inside the cell, but is expressed at the cell surface or in/at the cell membrane of a tumor cell.

A tumor cell antigen may be a tumor-specific antigen. Abnormal expression of a tumor specific antigen may be associated with the cause of the cancer. Tumor specific antigens may be preferentially expressed on cells of the tumor/cancer and not on healthy cells of the same type. Accordingly, tumor cell antigens may be products of mutated oncogenes or tumor suppressor genes.

A tumor cell antigen may be a tumor-associated antigen. Tumor-associated antigens may also be abnormally by the cell type concerned. Tumor-associated antigens are not normally associated with the cause of the cancer, their abnormal expression normally being associated with, or a consequence of, the cancer. Accordingly, tumor-associated antigens may be products of overexpressed cellular proteins, tumor antigens produced by oncogenic viruses, oncofetal antigens, cell surface glycolipids or glycoproteins.

Tumor antigens are reviewed by Zarour H M, DeLeo A, Finn O J, et al. Categories of Tumor Antigens. In: Kufe D W, Pollock R E, Weichselbaum R R, et al., editors. Holland-Frei Cancer Medicine. 6th edition. Hamilton (ON): BC Decker; 2003. Tumor cell antigens include oncofetal antigens: CEA, Immature laminin receptor, TAG-72; oncoviral antigens such as HPV E6 and E7; overexpressed proteins: BING-4, calcium-activated chloride channel 2, cyclin-B1, 9D7, Ep-CAM, EphA3, Her2/neu, telomerase, mesothelin, SAP-1, surviving; cancer-testis antigens: BAGE, CAGE, GAGE, MAGE, SAGE, XAGE, CT9, CT10, NY-ESO-1, PRAME, SSX-2; lineage restricted antigens: MARTI, Gp100, tyrosinase, TRP-1/2, MCIR, prostate specific antigen; mutated antigens: β-catenin, BRCA1/2, CDK4, CML66, Fibronectin, MART-2, p53, Ras, TGF-βRII; post-translationally altered antigens: MUC1, idiotypic antigens: Ig, TCR. Other tumor cell antigens include heat-shock protein 70 (HSP70), heat-shock protein 90 (HSP90), glucose-regulated protein 78 (GRP78), vimentin, nucleolin, feto-acinar pancreatic protein (FAPP), alkaline phosphatase placental-like 2 (ALPPL-2), siglec-5, stress-induced phosphoprotein 1 (STIP1), protein tyrosine kinase 7 (PTK7), cyclophilin B.

For example, where the tumor cell is a breast cancer cell, the antigen may be one of EpCAM (epithelial cell adhesion molecule), Her2/neu (Human Epidermal growth factor Receptor 2), MUC-1, EGFR (epidermal growth factor receptor), TAG-12 (tumor associated glycoprotein 12), IGF1 R (insulin-like growth factor 1 receptor), TACSTD2 (tumor associated calcium signal transducer 2), CD318, CD340, CD104, or N-cadherin.

For example, where the tumor cell is a prostate cancer cell, the antigen may be one of EpCAM, MUC-1, EGFR, PSMA (prostate specific membrane antigen), PSA (prostate specific antigen), TACSTD2, PSCA (prostate stem cell antigen), PCSA (prostate cell surface antigen), CD318, CD104, or N-cadherin.

For example, where the tumor cell is a colorectal cancer cell, the antigen may be one of EpCAM, CD66c, CD66e, CEA (carcinoembryonic antigen), TACSTD2, CK20 (cytokeratin 20), CD104, MUC-1, CD318, or N-cadherin.

For example, where the tumor cell is a lung cancer cell the antigen may be one or CK18, CK19, CEA, EGFR, TACSTD2, CD318, CD1 04, or EpCAM.

For example, where the tumor cell is a pancreatic cancer cell the antigen may be one of HSP70, mHSP70, vimentin, HSP90, MUC-1, TACSTD2, CEA, CD104, CD318, N-cadherin, or EpCAM1.

For example, where the tumor cell is an ovarian cancer cell the antigen may be one of MUC-1, TACSTD2, CD318, CD104, N-cadherin, or EpCAM.

For example, where the tumor cell is a bladder cancer cell, the antigen may be one of CD34, CD146, CD62, CD105, CD106, VEGF receptor (vascular endothelial growth factor receptor), MUC-1, TACSTD2, EpCAM, CD318, EGFR, 6B5 or Folate binding receptor.

For example, where the tumor cell is a cancer stem cell, the antigen may be one of CD133, CD135, CD 117, or CD34.

For example, where the tumor cell is a melanoma cancer cell, the antigen may be one of the melanocyte differentiation antigens, oncofetal antigens, tumor specific antigens, SEREX antigens or a combination thereof. Examples of melanocyte differentiation antigens, include but are not limited to tyrosinase, gp75, gp100, MART 1 or TRP-2. Examples of oncofetal antigens include antigens in the MAGE family (MAGE-AI, MAGE-A4), BAGE family, GAGE family or NY-ESO1. Examples of tumor-specific antigens include CDK4 and 13-catenin. Examples of SEREX antigens include D-1 and SSX-2.

In some preferred embodiments the tumor cell antigen is HSP70 or mHSP70. In embodiments, the tumor cell is a pancreatic cancer cell. In embodiments, the tumor cell is a glioblastoma cell. In embodiments, the tumor cell is a colon cancer cell.

The term "HSP70" refers to the family of approximately 70 kilodalton heat shock proteins as well-known in the art. In some preferred embodiments, the HSP70 is mHSP70. The term "mHSP70" as provided herein includes any of the mitochondrial HSP70 (mHSP70) protein naturally occurring forms, homologs or variants that maintain the activity of mHSP70 (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the mHSP70 protein is the protein as identified by the NCBI sequence reference NP 004125.3 GI:24234688, homolog or functional fragment thereof. mHSP70 may also be referred to herein as mortalin, CSA, GRP-75, GRP75, HEL-S-124m, HSPA9B, MOT, MOT2, MTHSP75 or PBP74. Overexpression of HSP70 in cancer is linked to poor prognosis, e.g. see Bagatell and Whitesell, Mol Cancer Ther Aug. 2004 3; 1021.

In some preferred embodiments the tumor cell antigen is vimentin. In embodiments, the tumor cell is a pancreatic cancer cell. In embodiments, the tumor cell is a glioblastoma cell. In embodiments, the tumor cell is a colon cancer cell.

The term "vimentin" refers to the family of class III intermediate filaments found in a number of health non-epithelial cells, including mesenchymal stem cells. The term "vimentin" as provided herein includes any of the protein naturally occurring forms, homologs or variants that maintain the activity of vimentin (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the vimentin protein is the protein as identified by the UniProt accession no. P08670 NCBI sequence reference or by Genbank accession no. NP 003371.2 GI:62414289. Vimentin is overexpressed in various epithelial cancers, including prostate cancer, gastrointestinal tumors, tumors of the central nervous system, breast cancer, malignant melanoma, and lung cancer (Satelli et al., Cell mol Life Sci 2011 September; 68(18):3033-46.

In some preferred embodiments the tumor cell antigen is HSP90. In embodiments, the tumor cell is a pancreatic cancer cell. In embodiments, the tumor cell is a glioblastoma cell. In embodiments, the tumor cell is a colon cancer cell.

The term "HSP90" refers to the family of approximately 90 kilodalton heat shock proteins as well-known in the art. The term "HSP90" as provided herein includes any of the protein naturally occurring forms, homologs or variants that maintain the activity of HSP90 (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the HSP90 protein is the protein as identified by Genbank accession no. NP_001017963.2 GI:153792590 or NP_005339.3 GI:154146191. Overexpression of HSP90 in cancer is linked to poor prognosis, e.g. see Bagatell and Whitesell, Mol Cancer Ther Aug. 2004 3; 1021.

In some preferred embodiments the tumor cell antigen is transferrin receptor.

The term "TfR" as provided herein includes any of the transferrin receptor (TfR) protein naturally occurring forms, homologs or variants that maintain the activity of TfR (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g.

a 50, 100, 150 or 200 continuous amino acid portion) compared to a naturally occurring form. In embodiments, the TfR protein is the protein as identified by the NCBI sequence reference NP_003225.2 GI:189458817. In embodiments, the TfR protein is the protein as identified by the NCBI sequence reference GI:189458816. In embodiments, the TfR protein is the protein as identified by the NCBI sequence reference GI:189458818. In embodiments, the TfR protein is the protein as identified by the NCBI sequence reference GI:189458817, homolog or functional fragment thereof. In embodiments, the TfR protein is the protein as identified by the NCBI sequence reference GI:189458816, homolog or functional fragment thereof. In embodiments, the TfR protein is the protein as identified by the NCBI sequence reference GI:189458818, homolog or functional fragment thereof. In embodiments, the TfR protein is encoded by a nucleic acid sequence corresponding to Gene ID: 7037.

The transferrin receptor (TfR) is a membrane glycoprotein expressed on the cellular surface and mediates cellular uptake of iron from the plasma glycoprotein transferrin. Iron uptake from transferrin involves the binding of transferrin to TfR. The bound transferrin is then internalized through receptor-mediated endocytosis in an endocytic vesicle. The release of transferrin from TfR is induced by a decrease in the pH within the endocytic vescile. TfR is expressed on a broad variety of cells at varying levels. For example, TfR is highly expressed on immature erythroid cells, placental tissue, and rapidly dividing cells, both normal and malignant. Thus, compounds capable of binding to TfR on the surface of TfR-expressing cells and internalizing into the cell would be very useful for targeted delivery of such compounds.

In some preferred embodiments the tumor cell antigen is alpha-type platelet-derived growth factor receptor.

The term "PDGFR-a" as provided herein includes any of the alpha-type platelet-derived growth factor receptor (PDGFR-a) protein naturally occurring forms, homologs or variants that maintain the tyrosine kinase activity of PDGFR-a (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the PDGFR-a protein is the protein as identified by the NCBI sequence reference NP_006197.1 GI:5453870. In embodiments, the PDGFR-a protein is the protein as identified by the NCBI sequence reference GI:5453870, homolog or functional fragment thereof. In embodiments, the PDGFR-a protein is encoded by a nucleic acid sequence corresponding to Gene ID: GI:172072625.

Platelet-derived growth factor receptor alpha (PDGFR-a) is a cell-surface tyrosine kinase receptor implicated in regulating cell proliferation, cellular differentiation, cell growth and development. PDGFR-a is frequently expressed by tumor cells, predominantly by malignant tumor cells. The expression levels of PDGFR-a correlates with tumor growth, invasiveness, drug resistance and poor clinical outcomes. For example, PDGFR-a is highly over expressed in glioblastoma (GBM). Thus, compounds capable of binding to PDGFR on the surface of PDGFR-expressing cells and internalizing into the cell are highly desirable.

The term "immune cell surface protein" refers to any protein present at the cell surface of an immune cell. In some embodiments it is a T-cell surface protein, receptor or co-receptor. In some embodiments it is a cluster of differentiation (CD) cell surface molecule, preferably when present on an immune cell. In some embodiments it is a CC chemokine receptor (CCR), preferably when present on an immune cell. In some embodiments it is a CXC chemokine receptor (CXCR), preferably when present on an immune cell.

An "immune cell" may be a lymphocyte, white blood cell, T-cell (thymocyte), T-helper cell, cytotoxic T-cell, CD8+ T-cell, CD4+ T-cell, memory T-cell, suppressor T-cell, natural killer T-cell, gamma delta T-cell, B cell, natural killer cell, leukocyte, macrophage, neutrophil, dendritic cell. An immune cell may express any one of CCR5, CCR7, CD2, CD3, CD4, CD7, CD8, PD-1, CTLA4 at the cell surface or in/at the cell membrane. In some preferred embodiments an immune cell may be a T-cell, e.g. expressing a T-cell receptor on its surface. In some preferred embodiments the immune cell may be a CD8+ T-cell. In some preferred embodiments the immune cell may be a CD4+ T-cell. In some preferred embodiments the immune cell is a cytotoxic T-cell.

In preferred embodiments, the immune cell surface protein is selected from the group consisting of CCR5, CCR7, CD2, CD3, CD4, CD7, CD8, PD-1, CTLA4.

The term "CCR5" as provided herein includes any of the C—C chemokine receptor type 5 (CCR5) protein naturally occurring forms, homologs or variants that maintain the activity of CCR5 (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the CCR5 protein is the protein as identified by the UniProt sequence reference P51681. In embodiments, the CCR5 protein is the protein as identified by the NCBI sequence reference NP_000570.1 GI:4502639, homolog or functional fragment thereof. In embodiments, the CCR5 protein is encoded by a nucleic acid sequence corresponding to Gene ID: GI:154091329.

Human CCR5 (C—C chemokine receptor type 5), a 7 pass transmembrane receptor expressed by T-cells and macrophages, serves as a co-receptor for macrophage-tropic HIV-1. A loss of CCR5 is associated with resistance to HIV-1. Thus, CCR5 is an important co-receptor for macrophage-tropic virus, including HIV-I RS isolates. Variations in CCR5 are associated with resistance or susceptibility to HIV-1. As an essential factor for viral entry, CCR5 has represented an attractive cellular target for the treatment of HIV-1. CCR5 is also known as CD195.

The term "CCR7" refers to C—C chemokine receptor type 7 (also called CD197), well-known in the art. The term "CCR7" as provided herein includes any of the naturally occurring forms, homologs or variants that maintain the activity of CCR7 (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the CCR7 protein is the protein as identified by the NCBI sequence reference NP_001288643.1 GI:683523912, homolog or functional fragment thereof. CCR7 is a member of the G protein coupled receptor family.

The term "CD2" refers to cluster of differentiation 2, well-known in the art. The term "CD2" as provided herein includes any of the naturally occurring forms, homologs or variants that maintain the activity of CD2 (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the CD2 protein is the protein as identified by the Uniprot accession no. P06729 or NCBI sequence reference NP_001758.2 GI:156071472, homolog or functional fragment thereof. CD2 is a cell adhesion molecule normally found on the surface of T cells and natural killer (NK) cells.

The term "CD3" refers to cluster of differentiation 3, well-known in the art, and includes any one of the CD3γ, CD3δ or CD3ε chains. The term "CD3" as provided herein includes any of the naturally occurring forms, homologs or variants that maintain the activity of CD3 (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the CD3γ protein is the protein as identified by the NCBI sequence reference NM 000073.2 GI:166362738, homolog or functional fragment thereof. In embodiments, the CD3ε protein is the protein as identified by the NCBI sequence reference NM_000732.4 GI:98985799, homolog or functional fragment thereof. In embodiments, the CD3ε protein is the protein as identified by the NCBI sequence reference NM_000733.3 GI:166362733, homolog or functional fragment thereof. Cd3 is a T-cell co-receptor that helps activate T-cell cytotoxicity.

The term "CD4" refers to cluster of differentiation 4, well-known in the art. The term "CD4" as provided herein includes any of the naturally occurring forms, homologs or variants that maintain the activity of CD4 (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the CD4 protein is the protein as identified by the UniProt accession no. 901730 or NCBI sequence reference NP_000607.1 GI:10835167, homolog or functional fragment thereof. CD4 is a glycoprotein found on the surface of immune cells such as T-helper cells, monocytes, macrophages and dendritic cells.

The term "CD7" refers to cluster of differentiation 7, well-known in the art. The term "CD7" as provided herein includes any of the naturally occurring forms, homologs or variants that maintain the activity of CD7 (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the CD7 protein is the protein as identified by the NCBI sequence reference NP_006128.1 GI:5453613, homolog or functional fragment thereof. CD7 is a transmembrane protein found on thymocytes and mature T cells.

The term "CD8" refers to cluster of differentiation 8, well-known in the art, and includes any one of the CD8a or CD8b chains. The term "CD8" as provided herein includes any of the naturally occurring forms, homologs or variants that maintain the activity of CD8 (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the CD8a protein is the protein as identified by the NCBI sequence reference NM 001768.6 GI:225007534, homolog or functional fragment thereof. In embodiments, the CD8b protein is the protein as identified by the NCBI sequence reference AAI00912.1 GI:71682667, homolog or functional fragment thereof. CD8 is a transmembrane glycoprotein co-receptor for the T-cell receptor.

The term "PD-1" refers to programmed cell death 1, well-known in the art. Programmed cell death 1 (PD-1), also called CD279, is a type I membrane protein encoded in humans by the PDCD1 gene. It has two ligands, PD-L1 and PD-L2. The term "PD-1" as provided herein includes any of the naturally occurring forms, homologs or variants that maintain the activity of PD-1 (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the PD-1 protein is the protein as identified by UniProt accession no. Q15116 or the NCBI sequence reference NP_005009.2 GI:167857792, homolog or functional fragment thereof. The PD-1 pathway is a key immune-inhibitory mediator of T-cell exhaustion. Blockade of this pathway can lead to T-cell activation, expansion, and enhanced effector functions. As such, PD-1 negatively regulates T cell responses. PD-1 has been identified as a marker of exhausted T cells in chronic disease states, and blockade of PD-1:PD-1L interactions has been shown to partially restore T cell function. (Sakuishi et al., *JEM* Vol. 207, Sep. 27, 2010, pp 2187-2194). Nivolumab (BMS-936558) is an anti-PD-1 antibody that was approved for the treatment of melanoma in Japan in July 2014. Other anti-PD-1 antibodies are described in WO 2010/077634, WO 2006/121168, WO2008/156712 and WO2012/135408.

The term "CTLA4" refers to cytotoxic T-lymphocyte-associated protein 4 (also called CD152), well-known in the art. It is a protein receptor found on the surface of T cells acting as an immune checkpoint. The term "CTLA4" as provided herein includes any of the naturally occurring forms, homologs or variants that maintain the activity of CTLA4 (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the CTLA4 protein is the protein as identified by UniProt accession no. P16410 or the NCBI sequence reference NP_001032720.1 GI:83700231, homolog or functional fragment thereof.

The term "C/EBPa" or "C/EBPalpha" as provided herein includes any of the CCAAT (cytosine-cytosine-adenosine-adensoine-thymidine)/enhancer-binding protein alpha (C/EBPa) naturally occurring forms, homologs or variants that maintain the transcription factor activity of C/EBPalpha (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the C/EBPalpha protein is the protein as identified by the NCBI sequence reference GI:551894998. In embodiments, the C/EBPalpha protein is the protein as identified by the NCBI sequence reference GI:551894998, homolog or functional fragment thereof. In embodiments, the C/EBPalpha protein is encoded by a nucleic acid sequence corresponding to Gene ID: GI:551894997.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *spodoptera*) and human cells.

"Anti-cancer agent" is used in accordance with its plain ordinary meaning and refers to a composition (e.g. compound, drug, antagonist, inhibitor, modulator) having anti-neoplastic properties or the ability to inhibit the growth or proliferation of cells. In embodiments, an anticancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSKI 120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), or adrenocortical suppressant (e.g., mitotane, aminoglutethimide), epipodophyllotoxins (e.g., etoposide).

Further examples of anti-cancer agents include, but are not limited to, antibiotics (e.g., daunorubicin, doxorubicin, bleomycin), enzymes (e.g., L-asparaginase), inhibitors of mitogen activated protein kinase signaling (e.g. U0126, PD98059, PD-184352, PD0325901, ARRY-142886, SB239063, SP600125, BAY 43-9006, wortmannin, or LY294002), mTOR inhibitors, antibodies (e.g., rituxan), 5-aza-2'-deoxycytidine, doxorubicin, vincristine, etoposide, gemcitabine, imatinib (Gleevec®), geldanamycin, 1 7-N-Allylamino-17-Demethoxygeldanamycin (17-AAG), bortezomib, trastuzumab, anastrozole; angiogenesis inhibitors; antiandrogen, antiestrogen; antisense oligonucleotides; apoptosis gene modulators; apoptosis regulators; arginine deaminase; BCR/ABL antagonists; beta lactam derivatives; bFGF inhibitor; bicalutamide; camptothecin derivatives; casein kinase inhibitors (ICOS); clomifene analogues; cytarabine dacliximab; dexamethasone; estrogen agonists; estrogen antagonists; etanidazole; etoposide phosphate; exemestane; fadrozole; finasteride; fludarabine; fluorodaunorunicin hydrochloride; gadolinium texaphyrin; gallium nitrate; gelatinase inhibitors; gemcitabine; glutathione inhibitors; hepsulfam; immunostimulant peptides; insulin-like growth factor-I receptor inhibitor; interferon agonists; interferons; interleukins; letrozole; leukemia inhibiting factor; leukocyte alpha interferon; leuprolide+estrogen+progesterone; leuprorelin; matrilysin inhibitors; matrix metalloproteinase inhibitors; MIF inhibitor; mifepristone; mismatched double stranded RNA; monoclonal antibody; mycobacterial cell wall extract; nitric oxide modulators; oxaliplatin; panomifene; pentrozole; phosphatase inhibitors; plasminogen activator inhibitor; platinum complex; platinum compounds; prednisone; proteasome inhibitors; protein A-based immune modulator; protein kinase C inhibitor; protein kinase C inhibitors, protein tyrosine phosphatase inhibitors; purine nucleoside phosphorylase inhibitors; ras farnesyl protein transferase inhibitors; ras inhibitors; ras-GAP inhibitor; ribozymes; signal transduction inhibitors; signal transduction modulators; single chain antigen-binding protein; stem cell inhibitor; stem-cell division inhibitors; stromelysin inhibitors; synthetic glycosaminoglycans; tamoxifen methiodide; telomerase inhibitors; thyroid stimulating hormone; translation inhibitors; tyrosine kinase inhibitors; urokinase receptor antagonists; steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to 111In, 90Y, or 131I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD-153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

Additionally, the nucleic acid compound described herein can be co-administered with or covalently attached to conventional immunotherapeutic agents including, but not limited to, immunostimulants (e.g., *Bacillus* Calmette-Guerin (BCG), levamisole, interleukin-2, alphainterferon, etc.), monoclonal antibodies (e.g., anti-CD20, anti-HER2, anti-CD52, anti-HLA-DR, anti-PD-1 and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), and radioimmunotherapy (e.g., anti-CD20 monoclonal antibody conjugated to 111 In, 90 Y, or 131I, etc.).

In a further embodiment, the nucleic acid compounds described herein can be coadministered with conventional radiotherapeutic agents including, but not limited to, radionucleotides such as $^{47}$Sc, $^{64}$Cu, $^{67}$Cu, $^{89}$Sr, $^{86}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{211}$At and $^{212}$Bi, optionally conjugated to antibodies directed against tumor antigens.

The term "sample" includes sections of tissues such as biopsy and autopsy samples, and frozen sections taken for histological purposes. Such samples include blood and blood fractions or products (e.g., bone marrow, serum, plasma, platelets, red blood cells, and the like), sputum, tissue, cultured cells (e.g., primary cultures, explants, and transformed cells), stool, urine, other biological fluids (e.g., prostatic fluid, gastric fluid, intestinal fluid, renal fluid, lung fluid, cerebrospinal fluid, and the like), etc. A sample is typically obtained from a "subject" such as a eukaryotic organism, most preferably a mammal such as a primate, e.g., chimpanzee or human; cow; dog; cat; a rodent, e.g., guinea pig, rat, mouse; rabbit; or a bird; reptile; or fish. In some embodiments, the sample is obtained from a human.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

"Disease" or "condition" refers to a state of being or health status of a patient or subject capable of being treated with a compound, pharmaceutical composition, or method provided herein. In preferred embodiments, the disease is cancer (e.g. pancreatic cancer, prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma), an infectious disease (e.g., HIV infection), an inflammatory disease (e.g., rheumatoid arthritis) or a metabolic disease (e.g., diabetes). In embodiments, the disease is a disease related to (e.g. caused by) an aberrant activity of HSP70 (e.g. mHSP70), HSP70 (e.g. mHSP70) phosphorylation, or HSP70 (e.g. mHSP70) pathway activity, or pathway activated by HSP70. In some embodiments, the disease is cancer (e.g. pancreatic cancer, prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma).

As used herein, the term "cancer" refers to all types of cancer, neoplasm or malignant tumors found in mammals, including leukemia, lymphoma, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or a leukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatinifomi carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The term "associated" or "associated with" in the context of a substance or substance activity or function associated with a disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma)) means that the disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma) or viral disease (e.g., HIV infection associated disease)) is caused by (in whole or in part), or a symptom of the disease is caused by (in whole or in part) the substance or substance activity or function.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by using a method as described herein), results in reduction of the disease or one or more disease symptoms.

In some embodiments, the cancer is one in which at least one of HSP70, vimentin, HSP90, TfR or PDGFR-a expression is upregulated (overexpressed). For example HSP70 is constitutively overexpressed in pancreatic cancer cells (Hyun et al., Gut Liver. 2013 November; 7(6):739-46).

Upregulation of expression comprises expression of at least one of (optionally only one of) HSP70, vimentin, HSP90, TfR or PDGFR-a at a level that is greater than would normally be expected for a cell or tissue of a given type. Upregulation may be determined by determining the level of expression at least one of HSP70, vimentin, HSP90, TfR or PDGFR-a in a cell or tissue. A comparison may be made between the level of expression in a cell or tissue sample from a subject and a reference level of, e.g. a value or range of values representing a normal level of expression for the same or corresponding cell or tissue type. In some embodiments reference levels may be determined by detecting expression in a control sample, e.g. in corresponding cells or tissue from a healthy subject or from healthy tissue of the same subject. In some embodiments reference levels may be obtained from a standard curve or data set.

Levels of expression may be quantitated for absolute comparison, or relative comparisons may be made.

In some embodiments upregulation of expression may be considered to be present when the level of expression in the test sample is at least 1.1 times that of a reference level. More preferably, the level of expression may be selected from one of at least 1.2, at least 1.3, at least 1.4, at least 1.5, at least 1.6, at least 1.7, at least 1.8, at least 1.9, at least 2.0, at least 2.1, at least 2.2, at least 2.3, at least 2.4 at least 2.5, at least 2.6, at least 2.7, at least 2.8, at least 2.9, at least 3.0, at least 3.5, at least 4.0, at least 5.0, at least 6.0, at least 7.0, at least 8.0, at least 9.0, or at least 10.0 times that of the reference level.

Expression levels may be determined by one of a number of known in vitro assay techniques, such as PCR based assays, in situ hybridisation assays, flow cytometry assays, immunological or immunohistochemical assays.

By way of example suitable techniques involve a method of detecting the level of at least one of (optionally only one of) HSP70, vimentin, HSP90, TfR or PDGFR-a in a sample by contacting the sample with an agent capable of binding at least one of HSP70, vimentin, HSP90, TfR or PDGFR-a and detecting the formation of a complex of the agent and at least one of HSP70, vimentin, HSP90, TfR or PDGFR-a. The agent may be any suitable binding molecule, e.g. an antibody, polypeptide, peptide, oligonucleotide, aptamer or small molecule, and may optionally be labelled to permit detection, e.g. visualisation, of the complexes formed. Suitable labels and means for their detection are well known to those in the art and include fluorescent labels (e.g. fluorescein, rhodamine, eosine and NDB, green fluorescent protein (GFP), chelates of rare earths such as europium (Eu), terbium (Tb) and samarium (Sm), tetramethyl rhodamine, Texas Red, 4-methyl umbelliferone, 7-amino-4-methyl coumarin, Cy3, Cy5), isotope markers, radioisotopes (e.g. 32P, 33p, 35S), chemiluminescence labels (e.g. acridinium ester, luminol, isoluminol), enzymes (e.g. peroxidase, alkaline phosphatase, glucose oxidase, beta-galactosidase, luciferase), antibodies, ligands and receptors. Detection techniques are well known to those of skill in the art and can be selected to correspond with the labelling agent. Suitable techniques include PCR amplification of oligonucleotide tags, mass spectrometry, detection of fluorescence or colour, e.g. upon enzymatic conversion of a substrate by a reporter protein, or detection of radioactivity.

Assays may be configured to quantify the amount of at least one of HSP70, vimentin, HSP90, TfR or PDGFR-a in a sample. Quantified amounts from a test sample may be compared with reference values, and the comparison used to determine whether the test sample contains an amount of at least one of HSP70, vimentin, HSP90, TfR or PDGFR-a that is higher or lower than that of the reference value to a selected degree of statistical significance.

Quantification of detected HSP70, vimentin, HSP90, TfR or PDGFR-a may be used to determine up- or down-regulation or amplification of genes encoding HSP70, vimentin, HSP90, TfR or PDGFR-a.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. Contacting may include allowing two species to react, interact, or physically touch, wherein the two species may be a nucleic acid compound as described herein and a cell (e.g., cancer cell).

Nucleic Acid Compounds

The aptamers provided herein, including embodiments thereof, are, inter alia, capable of binding cell surface protein target molecules and internalizing into the cell. For example, mHSP70, vimentin and HSP90 are expressed within and present on the surface of a broad variety of different cancer cells (e.g., pancreatic cancer, liver cancer, prostate cancer). CCR5, CCR7, CD2, CD3, CD4, CD7, CD8, PD-1, CTLA4 are expressed within and present on the surface of a variety of immune cells, including T-cells, Therefore, the compounds (e.g., nucleic acid compounds) provided herein, including embodiments thereof, may be used to deliver therapeutic or diagnostic molecules into a target molecule-expressing cancer cell. The therapeutic or diagnostic molecule may form part of the compound (e.g., nucleic acid compound) provided herein including embodiments thereof.

Where the therapeutic or diagnostic molecule forms part (e.g., through covalent attachment) of the compound (e.g., nucleic acid compound) provided herein, including embodiments thereof, the therapeutic or diagnostic molecule is referred to as a "compound moiety" (e.g., therapeutic moiety, imaging moiety). Alternatively, the therapeutic or diagnostic molecule may not form part of the compound (e.g., nucleic acid compound) provided herein, including embodiments thereof, but may be independently internalized by a target molecule-expressing cell upon binding of a compound (e.g., nucleic acid compound) provided herein to the target molecule on said cell. Where the therapeutic or diagnostic molecule does not form part of the compound (e.g., nucleic acid compound) provided herein, the molecule is referred to as a "second compound." The compounds (e.g., nucleic acid compounds) provided herein including embodiments thereof provide highly specific and efficient means for targeted cancer drug delivery and molecular imaging.

Where a nucleic acid sequence has at least 80%(80% or more) sequence identity to a given sequence, the nucleic acid sequence may have 80%, 85%, 90%, 91%, 92%, 93%, 94%, 95%, 96%, 97%, 98%, 99% or 100% sequence identity to that sequence (e.g., an aptamer sequence). In embodiments, nucleic acid sequence may have 80%, 85%, 90%, 91%, 92%, 93%, 94%, 95%, 96%, 97%, 98%, 99% or 100% sequence identity to the entire sequence of that sequence or to continuous portions (e.g., a 10, 20, 30, 40, 50, 60, 70, 80, 90 continuous nucleotides portion) of that aptamer sequence. In some embodiments, the nucleic acid sequence has at least 80%(80% or more) sequence identity to a nucleic acid that hybridizes to a given sequence.

In embodiments, the nucleic acid sequence of a monospecific aptamer or region of a bi-specific aptamer capable of binding one of the two target molecules is less than 100 (99 or less) nucleotides in length. For a bi-specific aptamer, two nucleic acid sequences may be present, each nucleic acid sequence having a length as described herein. The length calculation may optionally exclude nucleotides or carbon moieties of any spacer, linker or sticky bridge that forms part of the nucleic acid molecule. The length calculation may also optionally exclude any compound moiety conjugated to the nucleic acid, e.g. any nucleic acid moiety such as siRNA, saRNA, miRNA etc.

Where the nucleic sequence is less than 100 (99 or less) nucleotides in length the sequence is one of 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 nucleotides in length. In embodiments, the nucleic acid sequence is less than 90 nucleotides in length. In embodiments, the nucleic acid sequence is less than 80 nucleotides in length. In embodiments, the nucleic acid sequence is less than 70 nucleotides in length. In embodiments, the nucleic acid sequence is less than 60 nucleotides in length. In embodiments, the nucleic acid sequence is less than 50 nucleotides in length. In embodiments, the nucleic acid sequence is less than 40 nucleotides in length.

In embodiments, the nucleic acid sequence is between 20 and 99 nucleotides in length. In embodiments, the nucleic acid sequence is between 25 and 99 nucleotides in length. In embodiments, the nucleic acid sequence is between 30 and 99 nucleotides in length. In embodiments, the nucleic acid sequence is between 35 and 99 nucleotides in length. In embodiments, the nucleic acid sequence is between 40 and 99 nucleotides in length. In embodiments, the nucleic acid sequence is between 45 and 99 nucleotides in length. In embodiments, the nucleic acid sequence is between 50 and 99 nucleotides in length. In embodiments, the nucleic acid sequence is between 55 and 99 nucleotides in length. In embodiments, the nucleic acid sequence is between 60 and 99 nucleotides in length. In embodiments, the nucleic acid sequence is between 65 and 99 nucleotides in length. In embodiments, the nucleic acid sequence is between 70 and 99 nucleotides in length. In embodiments, the nucleic acid sequence is between 75 and 99 nucleotides in length. In embodiments, the nucleic acid sequence is between 80 and 99 nucleotides in length. In embodiments, the nucleic acid sequence is between 85 and 99 nucleotides in length.

Upon binding a target molecule on the surface of a cell, the nucleic acid compound provided herein (including embodiments thereof) may be internalized by the cell. The term "internalized," "internalizing," or "internalization" as provided herein refers to a composition (e.g., a compound, a nucleic acid compound, a therapeutic agent, an imaging agent) being drawn into the cytoplasm of the cell (e.g. after being engulfed by a cell membrane). In embodiments, the cell is a malignant cell. In embodiments, the cell is a breast cancer cell. In embodiments, the cell is a prostate cancer cell. In embodiments, the cell is a liver cancer cell. In embodiments, the cell is a pancreatic cancer cell. In embodiments, the cell is a lung cancer cell. In embodiments, the cell is a leukemia cell. In embodiments, the cell is a glioblastoma cell. In embodiments, the cell is a colon cancer cell. In embodiments, the cell is a non-malignant cell.

In some embodiments the aptamer is a deoxyribonucleic acid. In some preferred embodiments the aptamer may be a ribonucleic acid. The aptamer may be single stranded. Aptamers according to the present invention may contain one or more bases that are chemically modified. In some embodiments, each base of a given type (e.g. A, T, C, G) may contain the same chemical modification.

Aptamers according to the present invention may contain one or more nucleotides that are chemically modified at the 2' position of ribose. In some embodiments, each ribose contains the same chemical modification. In some other embodiments the ribose of certain nucleotides (e.g. A, T, C, G) may be independently modified. Such modifications may include O-methyl modification (2'-OMe), Fluoride modification (2'-F) or amine modification (2-$NH_2$).

The nucleic acid compound provided herein (including embodiments thereof) may include a compound moiety. Where the nucleic acid compound includes a compound moiety, the compound moiety may be covalently (e.g. directly or through a covalently bonded intermediary) attached to the nucleic acid sequence (see, e.g., useful reactive moieties or functional groups used for conjugate chemistries set forth above). Thus, in embodiments, the nucleic acid compound further includes a compound moiety covalently attached to the nucleic acid sequence. In embodiments, the compound moiety and the nucleic acid sequence form a conjugate. In embodiments, the compound moiety is non-covalently (e.g. through ionic bond(s), van der Waal's bond(s)/interactions, hydrogen bond(s), polar bond(s), or combinations or mixtures thereof) attached to the nucleic acid sequence.

In embodiments, the compound moiety is a therapeutic moiety or an imaging moiety.

In embodiments, the therapeutic moiety is covalently attached to the nucleic acid sequence. In embodiments, the imaging moiety is covalently attached to the nucleic acid sequence. The term "therapeutic moiety" as provided herein is used in accordance with its plain ordinary meaning and refers to a monovalent compound having a therapeutic benefit (prevention, eradication, amelioration of the underlying disorder being treated) when given to a subject in need thereof. Therapeutic moieties as provided herein may include, without limitation, peptides, proteins, nucleic acids, nucleic acid analogs, small molecules, antibodies, enzymes, prodrugs, cytotoxic agents (e.g. toxins) including, but not limited to ricin, doxorubicin, daunorubicin, taxol, ethidium bromide, mitomycin, etoposide, tenoposide, vincristine, vinblastine, colchicine, dihydroxy anthracin dione, actinomycin D, diphteria toxin, *Pseudomonas* exotoxin (PE) A, PE40, abrin, and glucocorticoid. In embodiments, the therapeutic moiety is an anti-cancer agent or chemotherapeutic agent as described herein. In embodiments, the therapeutic moiety is a nucleic acid moiety, a peptide moiety or a small molecule drug moiety. In embodiments, the therapeutic moiety is a nucleic acid moiety. In embodiments, the therapeutic moiety is a peptide moiety. In embodiments, the therapeutic moiety is a small molecule drug moiety. In embodiments, the therapeutic moiety is a nuclease. In embodiments, the therapeutic moiety is an immunostimulator. In embodiments, the therapeutic moiety is a toxin. In embodiments, the therapeutic moiety is a nuclease. In embodiments, the therapeutic moiety is a zinc finger nuclease. In embodiments, the therapeutic moiety is a transcription activator-like effector nuclease. In embodiments, the therapeutic moiety is Cas9. In embodiments, the therapeutic moiety is gemcitabine or a reactive fragment thereof. "Gemcitabine" as provided herein refers to the chemical compound 4-amino-1-(2-deoxy-2,2-difluoro-13-D-erythropentofuranosyl) pyrimidin-2(1H)-on. In a customary sense gemcitabine refers to CAS Registry No. 95058-81-4.

In embodiments, the therapeutic moiety is an activating nucleic acid moiety (a monovalent compound including an activating nucleic acid) or an antisense nucleic acid moiety (a monovalent compound including an antisense nucleic acid). An activating nucleic acid refers to a nucleic acid capable of detectably increasing the expression or activity of a given gene or protein. The activating nucleic acid can increase expression or activity 10%, 20%, 30%, 40%, 50%, 60%, 70%, 80%, 90% or more in comparison to a control in the absence of the activating nucleic acid. In certain instances, expression or activity is 1.5-fold, 2-fold, 3-fold, 4-fold, 5-fold, 10-fold or higher than the expression or activity in the absence of the activating nucleic acid.

In embodiments, the therapeutic moiety is an miRNA moiety (a monovalent compound including a miRNA), an mRNA moiety (a monovalent compound including an mRNA), an siRNA moiety (a monovalent compound including an siRNA) or an saRNA moiety (a monovalent compound including an saRNA). In embodiments, the therapeutic moiety is a miRNA moiety. The term "miRNA" is used in accordance with its plain ordinary meaning and refers to a small non-coding RNA molecule capable of post-transcriptionally regulating gene expression. In one embodiment, a miRNA is a nucleic acid that has substantial or complete identity to a target gene. In embodiments, the miRNA inhibits gene expression by interacting with a complementary cellular mRNA thereby interfering with the expression of the complementary mRNA. Typically, the miRNA is at least about 15-50 nucleotides in length (e.g., each complementary sequence of the miRNA is 15-50 nucleotides in length, and the miRNA is about 15-50 base pairs in length). In other embodiments, the length is 20-30 base nucleotides, preferably about 20-25 or about 24-29 nucleotides in length, e.g., 20, 21, 22, 23, 24, 25, 26, 27, 28, 29, or 30 nucleotides in length. In embodiments, the therapeutic moiety is a siRNA moiety or saRNA moiety as described herein. In embodiments, the therapeutic moiety is an anticancer agent moiety. In embodiments, the therapeutic moiety is an mRNA moiety. In embodiments, the therapeutic moiety is a siRNA moiety. In embodiments, the therapeutic moiety is a saRNA moiety. In embodiments, the therapeutic moiety is a cDNA moiety. In embodiments, the therapeutic moiety is a C/EBPalpha saRNA moiety. A "C/EBPalpha saRNA" as provided herein is a saRNA capable of activating the expression of a C/EBPalpha protein. In embodiments, the therapeutic moiety is a HSP70 siRNA moiety.

The compound moiety provided herein may be an imaging moiety. An "imaging moiety" as provided herein is a monovalent compound detectable by spectroscopic, photochemical, biochemical, immunochemical, chemical, or other physical means. In embodiments, the imaging moiety is covalently attached to the RNA sequence.

Exemplary imaging moieties are without limitation 32P, radionuclides, positron-emitting isotopes, fluorescent dyes, fluorophores, antibodies, bioluminescent molecules, chemoluminescent molecules, photoactive molecules, metals, electron-dense reagents, enzymes (e.g., as commonly used in an ELISA), magnetic contrast agents, quantum dots, nanoparticles, biotin, digoxigenin, haptens and proteins or other entities which can be made detectable, e.g., by incorporating a radiolabel into a peptide or antibody specifically reactive with a target peptide. Any method known in the art for conjugating an antibody to the moiety may be employed, e.g., using methods described in Hermanson, Bioconjugate Techniques 1996, Academic Press, Inc., San Diego. Exemplary fluorophores include fluorescein, rhodamine, GFP, coumarin, FITC, Alexa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese. In embodiments, the imaging moiety is a bioluminescent molecule.

In embodiments, the imaging moiety is a photoactive molecule. In embodiments, the imaging moiety is a metal. In embodiments, the imaging moiety is a nanoparticle.

The compound (e.g., nucleic acid compound) provided herein may include a ligand moiety. A "HSP70 ligand moiety" as used herein refers to a monovalent compound (e.g. substituent) capable of binding (interacting) to a tumor cell antigen or immune cell surface protein, as described herein. The binding may be specific relative to relative to other cell surface proteins. In embodiments, ligand moiety is a nucleic acid moiety, a peptide moiety or a small molecule moiety (e.g. a small molecule drug moiety). In embodiments, the ligand moiety forms part of the RNA sequence. In embodiments, the ligand moiety comprises or consists of the sequence of SEQ ID NO:8. In embodiments, the compound provided herein is bound to a cellular receptor. In embodiments, a cellular receptor is one of HSP70, vimentin, HSP90, TfR or PDGFR-a or one of CCR5, CCR7, CD2, CD3, CD4, CD7, CD8, PD-1, CTLA4. "Cell surface" as provided herein refers to a protein expressed (e.g. present) on the surface of a cell (i.e. on the cell membrane accessible to the extracellular space). In embodiments, the cellular receptor is expressed (e.g. present) on a cancer cell (i.e. on the cancer cell membrane accessible to the extracellular space). In embodiments, the cancer cell is a pancreatic cancer cell. In embodiments, the cancer cell is a glioblastoma cell. In embodiments, the cancer cell is a liver cancer cell. In embodiments, the cancer cell is a prostate cancer cell. In embodiments, the cancer cell is a breast cancer cell. In embodiments, the cancer cell is a leukemia cell. In embodiments, the cell is a colon cancer cell.

Pharmaceutical Formulations

Pharmaceutical compositions of the compounds (e.g., nucleic acid compounds) provided herein may include compositions having a therapeutic moiety contained in a therapeutically effective amount, i.e., in an amount effective to achieve its intended purpose.

The pharmaceutical compositions of the compounds (e.g., nucleic acid compounds) provided herein may include compositions having imaging moieties contained in an effective amount, i.e., in an amount effective to achieve its intended purpose. The actual amount effective for a particular application will depend, inter alia, on the condition being treated, tested, detected, or diagnosed. When administered in methods to treat a disease, such compositions will contain an amount of active ingredient effective to achieve the desired result, e.g., modulating the activity of a target molecule, and/or reducing, eliminating, or slowing the progression of disease symptoms. Determination of a therapeutically effective amount of a therapeutic moiety provided herein is well within the capabilities of those skilled in the art, especially in light of the detailed disclosure herein. When administered in methods to diagnose or detect a disease, such compositions will contain an amount of an imaging moiety described herein effective to achieve the desired result, e.g., detecting the absence or presence of a target molecule, cell, or tumor in a subject. Determination of a detectable amount of an imaging moiety provided herein is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compositions described herein including embodiments thereof. Adjustment and manipulation of established dosages (e.g., frequency and duration) are well within the ability of those skilled in the art.

For any composition (e.g., the nucleic acid compounds provided, combinations of an anticancer agent and the nucleic acid compound provided) described herein, the therapeutically effective amount can be initially determined from cell culture assays. Target concentrations will be those concentrations of active compound(s) that are capable of achieving the methods described herein, as measured using the methods described herein or known in the art. As is well known in the art, effective amounts for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

In another aspect, a pharmaceutical formulation including the nucleic acid compound as provided herein including embodiments thereof and a pharmaceutically acceptable excipient is provided. In embodiments, the ribonucleic acid includes a compound moiety covalently attached to the nucleic acid sequence. As described above, the compound moiety may be a therapeutic moiety or an imaging moiety covalently attached to the nucleic acid sequence.

In another aspect, the pharmaceutical formulation includes the nucleic acid compound as provided herein including embodiments thereof and a therapeutic agent. In embodiments, the nucleic acid compound and the therapeutic agent are not covalently attached. A therapeutic agent as provided herein refers to a composition (e.g. compound, drug, antagonist, inhibitor, modulator) having a therapeutic effect. In embodiments, the therapeutic agent is an anticancer agent. In embodiments, the pharmaceutical formulation includes a pharmaceutically acceptable excipient.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylase or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The pharmaceutical preparation is optionally in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The unit dosage form can be of a frozen dispersion.

Methods of Delivery

Provided herein are methods of delivering compounds (e.g., nucleic acid compounds as provided herein) to a cell through binding the compound to a cell surface target molecule (e.g. HSP70, vimentin, HSP90, TfR, PDGFR-a, CCR5, CCR7, CD2, CD3, CD4, CD7, CD8, PD-1, CTLA4) and internalizing the compound into the cell. Thus, in one aspect, a method of delivering a compound into a cell is provided. The method includes contacting a cell surface target molecule with a compound including a nucleic acid sequence capable of binding to the target molecule. The compound is allowed to pass into the cell thereby delivering the compound into the cell. The passage into the cell may be facilitated (mediated) by the cell surface target molecule.

In embodiments, the cell surface target molecule is present on a cell surface. In embodiments, the target molecule forms part of a cellular vesicle upon passage into the cell.

In embodiments, the compound includes a therapeutic agent or an imaging agent. In embodiments, the compound is a therapeutic agent or an imaging agent. In embodiments, the therapeutic agent is an antibody, a peptide, a nucleic acid or a small molecule (e.g. a drug). In embodiments, the imaging agent is a bioluminescent molecule, a photoactive molecule, a metal or a nanoparticle. In embodiments, the compound is an antibody, a peptide, a nucleic acid or a small molecule. In embodiments, the compound is an antibody. In embodiments, the compound is a nucleic acid compound as provided herein including embodiments thereof. In embodiments, the method includes detecting the nucleic acid compound in the cell thereby detecting the cell.

As described above the nucleic acid compounds provided herein including embodiments thereof may be used to deliver compound moieties or compounds (e.g., therapeutic agents or imaging agents) into a cell. Where a compound moiety (e.g., therapeutic moiety or imaging moiety) is delivered into a cell, the compound moiety may be covalently attached to the nucleic acid compound (RNA sequence) provided herein including embodiments thereof. Upon binding of the nucleic acid compound (RNA sequence) to a ligand on a cell, the compound moiety is internalized by the cell while being covalently attached to the nucleic acid compound (RNA sequence). Thus, in one aspect, a method of delivering a compound moiety into a cell is provided. The method includes, (i) contacting a cell with the nucleic acid compound as provided herein including embodiments thereof and (ii) allowing the nucleic acid compound to bind to a ligand on the cell and pass into the cell thereby delivering the compound moiety into the cell.

Alternatively, where a compound is delivered into a cell, the compound (e.g., a therapeutic agent or an imaging agent) may not be covalently attached to the nucleic acid compound (nucleic acid sequence). Upon binding of the nucleic acid compound provided herein including embodiments thereof to the target molecule on a cell, the nucleic acid compound and the compound provided are internalized by the cell without being covalently attached to each other.

Thus, in another aspect, a method of delivering a compound into a cell is provided. The method includes (i) contacting a cell with a compound and the nucleic acid compound as provided herein including embodiments thereof and (ii) allowing the nucleic acid compound to bind to a target molecule on the cell and the compound to pass into the cell thereby delivering the compound into the cell. In embodiments, the compound is a therapeutic agent or imaging agent. In embodiments, the compound is non-covalently attached to the nucleic acid compound.

Methods of Treatment

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance. For example, certain methods herein treat cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma). For example certain methods herein treat cancer by decreasing or reducing or preventing the occurrence, growth, metastasis, or progression of cancer; or treat cancer by decreasing a symptom of cancer. Symptoms of cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma) would be known or may be determined by a person of ordinary skill in the art.

Where combination treatments are contemplated, it is not intended that the agents (i.e. nucleic acid compounds) described herein be limited by the particular nature of the combination. For example, the agents described herein may be administered in combination as simple mixtures as well as chemical hybrids. An example of the latter is where the agent is covalently linked to a targeting carrier or to an active pharmaceutical. Covalent binding can be accomplished in many ways, such as, though not limited to, the use of a commercially available cross-linking agent.

An "effective amount" is an amount sufficient to accomplish a stated purpose (e.g. achieve the effect for which it is administered, treat a disease, reduce enzyme activity, reduce one or more symptoms of a disease or condition, reduce viral replication in a cell). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme or protein relative to the absence of the antagonist. A "function disrupting amount," as used herein, refers to the amount of antagonist required to disrupt the function of an enzyme or protein relative to the absence of the antagonist. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

"Patient" or "subject in need thereof" refers to a living organism suffering from or prone to a disease or condition that can be treated by using the methods provided herein. The term does not necessarily indicate that the subject has been diagnosed with a particular disease, but typically refers to an individual under medical supervision. Non-limiting examples include humans, other mammals, bovines, rats, mice, dogs, monkeys, goat, sheep, cows, deer, and other non-mammalian animals. In embodiments, a patient is human.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal).

Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

In another aspect, a method of treating cancer is provided. The method includes administering to a subject in need thereof an effective amount of the nucleic acid compound as provided herein (including embodiments thereof). In embodiments, the nucleic acid compound further includes an anticancer therapeutic moiety. In another aspect, a method of treating cancer is provided. The method includes administering to a subject in need thereof an effective amount of an anticancer agent and a nucleic acid compound as provided herein including embodiments thereof.

Methods of Detecting a Cell

The nucleic acid compositions provided herein may also be used for the delivery of compounds and compound moieties to a cell expressing a target molecule (e.g. HSP70, vimentin, HSP90, TfR, PDGFR-a, CCR5, CCR7, CD2, CD3, CD4, CD7, CD8, PD-1, CTLA4). As described above, the compounds and compound moieties delivered may be imaging agents useful for cell detections. Thus, in one aspect, a method of detecting a cell is provided. The method includes (i) contacting a cell with the nucleic acid compound as provided herein including embodiments thereof, wherein the nucleic acid compound further includes an imaging moiety, (ii) the nucleic acid compound is allowed to bind to the target molecule on the cell and pass into the cell, (iii) the imaging moiety is detected thereby detecting the cell.

In another aspect, a method of detecting a cell is provided. The method includes (i) contacting a cell with an imaging agent and the nucleic acid compound as provided herein including embodiments thereof. (ii) The nucleic acid compound is allowed to bind to the target molecule on the cell and the imaging agent is allowed to pass into the cell. (iii) The imaging agent is detected thereby detecting the cell.

In embodiments, the cell is a malignant cell. In embodiments, the cell is a breast cancer cell. In embodiments, the cell is a prostate cancer cell. In embodiments, the cell is a liver cancer cell. In embodiments, the cell is a pancreatic cancer cell. In embodiments, the cancer cell is a glioblastoma cell. In embodiments, the cell is a colon cancer cell. In embodiments, the cell is a non-malignant cell. In embodiments, the cell forms part of an organism. In embodiments, the organism is a mammal. In embodiments, the cell forms part of a cell culture.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

EMBODIMENTS

Embodiments contemplated herein include embodiments P1 to P41 following.

Embodiment P1. A bi-specific aptamer capable of binding a tumor cell antigen and an immune cell surface protein.

Embodiment P2. The bi-specific aptamer of embodiment P1, wherein the tumor cell antigen is HSP70, vimentin, HSP90, TfR or PDGFR-a.

Embodiment P3. The bi-specific aptamer of embodiment P1 or P2, wherein the immune cell surface protein is selected from the group consisting of CCR5, CCR7, CD2, CD3, CD4, CD7, CD8, PD-1, CTLA4.

Embodiment P4. A bi-specific aptamer capable of binding a cancer cell and an immune cell.

Embodiment P5. A bi-specific aptamer capable of binding a pancreatic cancer cell and an immune cell.

Embodiment P6. The bi-specific aptamer of embodiment P4 or P5, wherein the immune cell is a T-cell.

Embodiment P7. A bi-specific aptamer capable of binding HSP70 and an immune cell surface protein.

Embodiment P8. A bi-specific aptamer capable of binding vimentin and an immune cell surface protein.

Embodiment P9. A bi-specific aptamer capable of binding HSP90 and an immune cell surface protein.

Embodiment P10. The bi-specific aptamer of any one of embodiments P4 to P9, wherein the immune cell surface protein is selected from the group consisting of CCR5, CCR7, CD2, CD3, CD4, CD7, CD8, PD-1, CTLA4.

Embodiment P11. A bi-specific aptamer capable of binding HSP70 and CCR5.

Embodiment P12. A bi-specific aptamer capable of binding vimentin and CCR5.

Embodiment P13. A bi-specific aptamer capable of binding HSP90 and CCR5.

Embodiment P14. The bi-specific aptamer according to any one of the preceding embodiments, wherein the HSP70 is mHSP70.

Embodiment P15. The bi-specific aptamer of any one of embodiments P1 to P14, wherein the bi-specific aptamer comprises the nucleic acid sequence of one of SEQ ID NOs: 1 to 7.

Embodiment P16. The bi-specific aptamer of any one of embodiments P1 to P14, wherein the bi-specific aptamer comprises a nucleic acid sequence having at least 80% sequence identity to one of SEQ ID NOs: 1 to 7.

Embodiment P17. The bi-specific aptamer of any one of embodiments P1 to P16, wherein the bi-specific aptamer comprises the nucleic acid sequence of SEQ ID NO:8.

Embodiment P18. The bi-specific aptamer of any one of embodiments P1 to P14, wherein the bi-specific aptamer comprises the nucleic acid sequence of one of SEQ ID NOs:28 to 30.

Embodiment P19. The bi-specific aptamer of any one of embodiments P1 to P14, wherein the bi-specific aptamer comprises a nucleic acid sequence having at least 80% sequence identity to one of SEQ ID NOs:28 to 30.

Embodiment P20. The bi-specific aptamer of any one of embodiments P1 to P14, wherein the bi-specific aptamer comprises the nucleic acid sequence of one of SEQ ID NOs:31 or 32.

Embodiment P21. The bi-specific aptamer of any one of embodiments P1 to P14, wherein the bi-specific aptamer comprises a nucleic acid sequence having at least 80% sequence identity to one of SEQ ID NOs:31 or 32.

Embodiment P22. The bi-specific aptamer of any one of embodiments P1 to P21, wherein the bi-specific aptamer comprises the nucleic acid sequence of one of SEQ ID NOs:9 to 16.

Embodiment P23. The bi-specific aptamer of any one of embodiments P1 to P21, wherein the bi-specific aptamer comprises a nucleic acid sequence having at least 80% sequence identity to one of SEQ ID NOs:9 to 16.

Embodiment P24. A bi-specific aptamer comprising one of SEQ ID NOs: 17, or 19 to 24.

Embodiment P25. A bi-specific aptamer comprising SEQ ID NO:18.

Embodiment P26. A bi-specific aptamer comprising a complex of one of one of SEQ ID NOs: 17, or 19 to 24 and SEQ ID NO: 18.

Embodiment P27. The bi-specific aptamer of any one of embodiments P1 to P26 wherein one or more bases or nucleotides are chemically modified.

Embodiment P28. The bi-specific aptamer of any one of embodiments P1 to P27 wherein one or more nucleotides are chemically modified at the 2' position of ribose.

Embodiment P29. A complex, optionally an in vitro complex, of a bi-specific aptamer according to any one of embodiments P1 to P28 and a tumor cell expressing a tumor cell antigen to which the bi-specific aptamer is capable of binding.

Embodiment P30. A complex, optionally an in vitro complex, of a bi-specific aptamer according to any one of embodiments P1 to P28 and an immune cell expressing an immune cell surface protein to which the bi-specific aptamer is capable of binding.

Embodiment P31. A complex, optionally an in vitro complex, of a bi-specific aptamer according to any one of embodiments P1 to P28, a tumor cell expressing a tumor cell antigen to which the bi-specific aptamer is capable of binding and an immune cell expressing an immune cell surface protein to which the bi-specific aptamer is capable of binding.

Embodiment P32. The complex of embodiment P30 or P31, wherein the immune cell is a T-cell.

Embodiment P33. A pharmaceutical composition comprising a bi-specific aptamer according to any one of embodiments P1 to P28 and a pharmaceutically acceptable carrier, diluent or excipient.

Embodiment P34. A bi-specific aptamer according to any one of embodiments P1 to P28 for use in a method of medical treatment.

Embodiment P35. A bi-specific aptamer according to any one of embodiments P1 to P28 for use in a method of treatment of cancer.

Embodiment P36. The bi-specific aptamer for use in a method of treatment of cancer according to embodiment P35, wherein the cancer is a pancreatic cancer.

Embodiment P37. The bi-specific aptamer for use in a method of treatment of cancer according to embodiment P35 or P36, wherein the cancer overexpresses at least one of HSP70, vimentin, HSP90, Tfr or PDGFR-a.

Embodiment P38. A method of treatment of cancer in a subject, the method comprising administering a therapeutically effective amount of a bi-specific aptamer according to any one of embodiments P1 to P28 to a subject in need of treatment.

Embodiment P39. The method of embodiment P38, wherein the cancer is a pancreatic cancer.

Embodiment P40. The method of embodiment P38 or P39, wherein the cancer overexpresses at least one of HSP70, vimentin, HSP90, Tfr or PDGFR-a.

Embodiment P41. A method of selecting a subject for treatment of cancer with a therapeutically effective amount of a bi-specific aptamer according to any one of embodiments P1 to P28, the method comprising determining, in vitro, whether cells of a cancer in the subject overexpress at least one of HSP70, vimentin, HSP90, TfR or PDGFR-a.

EXAMPLES

Example 1: Bi-Specific RNA Aptamers for Targeting Cancer

We investigated the construction of cancer specific bi-specific RNA aptamers to recruit endogenous T cells. The bi-specific RNA aptamers formed a bridge between cancer cell targets and T cells, forming an immunological 'cytolytic synapse' (FIG. 16), leading to rapid lysis of cancer cells.

1. Sequences tP19 (truncated P19; pancreatic cancer aptamer) conjugated to sticky sequence via polycarbon linker: fCfUfCAAf-UGGfCGAAfUGfCfCfCGfCfCfCfUAAfUAGG-GooooooomAmGfUfUfUfUfUfUmAfC mAfUfUfUfUmG (SEQ ID NO: 17)

CCR5 aptamer (G3; T cell surface markers): GGGAG-GAfCGAfUGfCGGGfCfCfUfUfCGfUfUfUGfUfU-fUfCGfUfCfCAfCAGAfCGAfCfUfC GfCfCfCGAooooofCmAmAmAmAfUmGfUmAmAmA-mAmAmAfCfU (SEQ ID NO: 18)

Bold: sticky sequence. fU and fC: 2'F modified pyrimidines. mA and mG: 2'O methylated purines, o: C3 carbon linker.

tP19 (SEQ ID NO:1) is an mHSP70 binding aptamer capable of internalising upon binding of mHSP70 at the cell surface, and described in WO2013/154735. tP19 is a truncated form of aptamer P19 which also binds mHSP70, also described in WO2013/154735. WO2013/154735 is specifically incorporated herein by reference in its entirety. tP19 is also described in U.S. provisional patent application No. 62/141,156, specifically incorporated herein by reference in its entirety.

The CCR5 binding aptamer G3 (SEQ ID NO:9) is described in Zhou et al., 2015, Chemistry & Biology 22, 379-390 Mar. 19, 2015 and in co-pending U.S. patent application Ser. No. 14/801,710, specifically incorporated herein by reference in its entirety.

Figure 4:
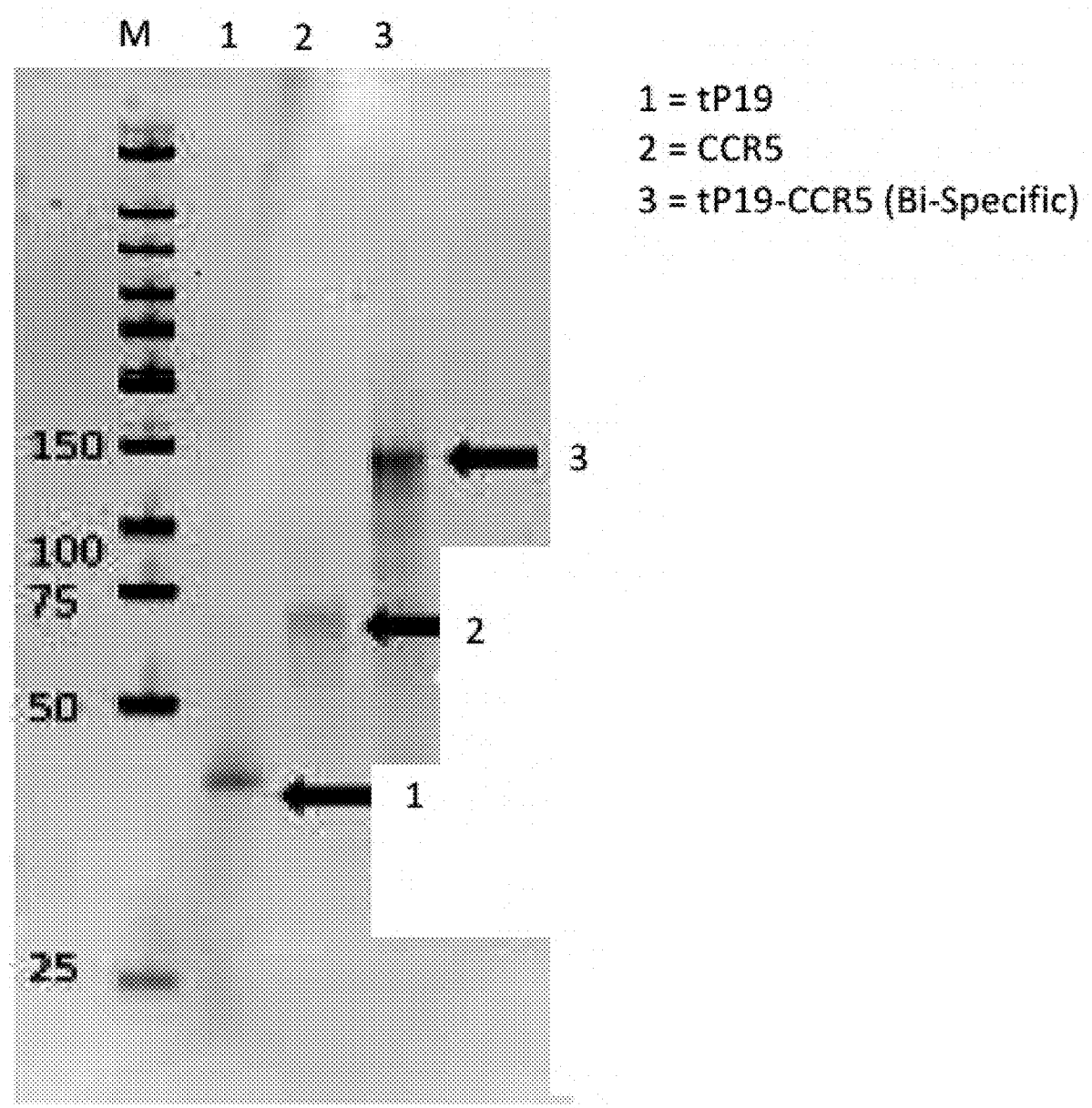
FIG. 4. Conjugates of bi-specific aptamers revealed by electrophoresis.
Figure 5:
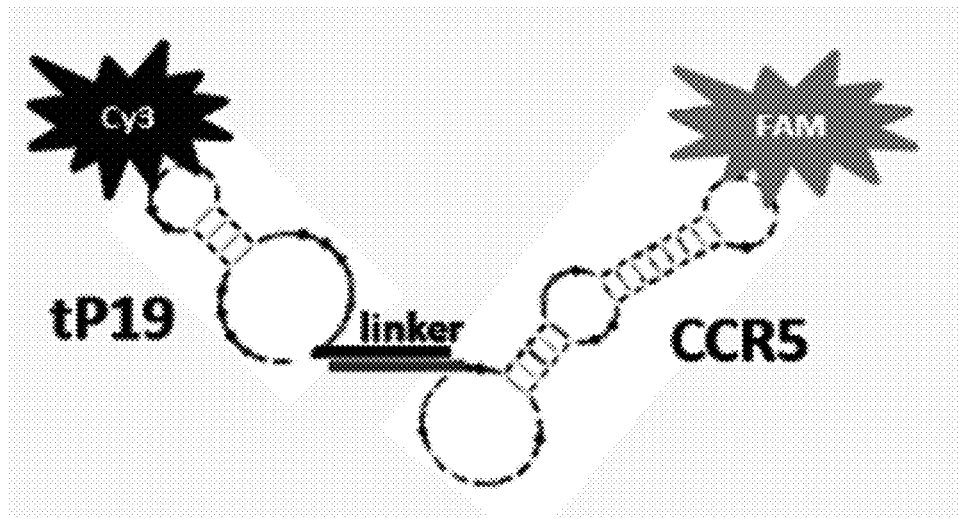
FIG. 5. Diagram illustrating use of Cy3 and FAM labelling to identify location of bi-specific aptamer during confocal microscopy.
Figure 6:
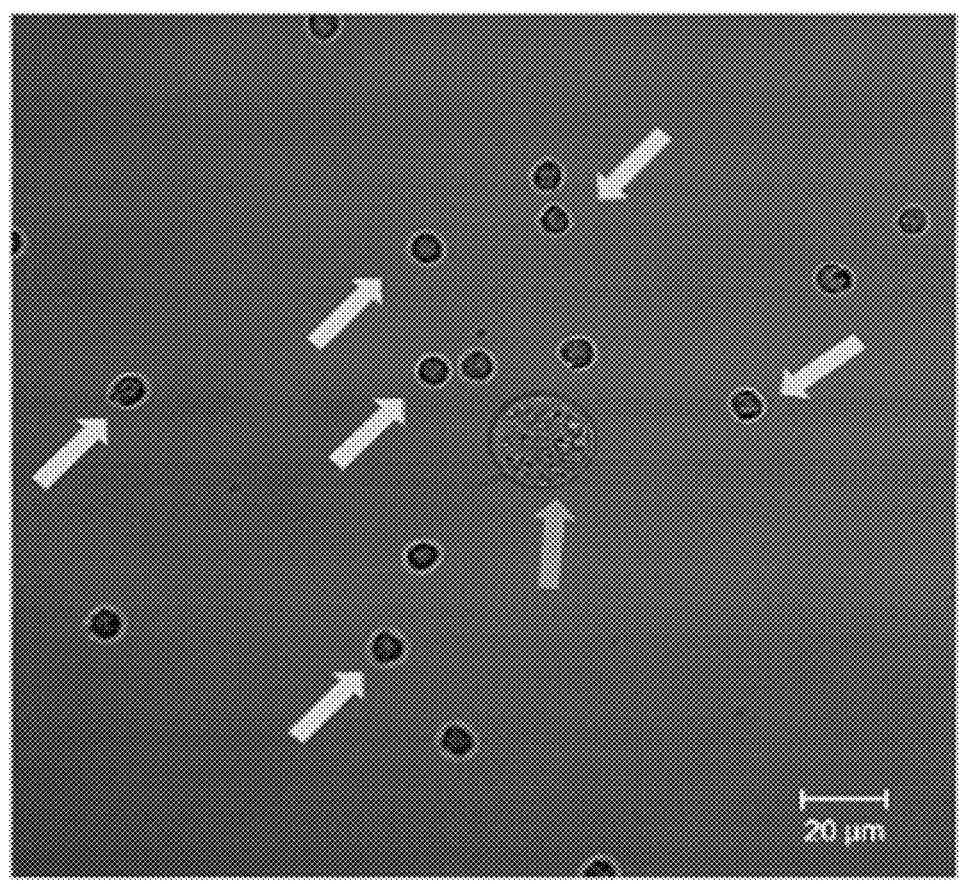
FIG. 6. Micrograph showing lack of association of T-cells (small cells) with PANC-1 cells (large cell) in absence of bi-specific aptamer.

2. Formation of Bi-Specific RNA Aptamers Capable of Binding mHSP70 and CCR5.

tP19 was folded in binding buffer (phosphate-buffered saline solution [DPBS] without $Ca^{2+}$ and $Mg^{2+}$, 5 mM $MgCl_2$) at 95° C. for 5 mins and slowly cooled down. CCR5 aptamer was folded in binding buffer (DPBS with $MgCl_2$ and $CaCl_2$)) at 65° C. for 5 mins and slowly cooled down. The same concentration of tP19 and CCR5 aptamers were mixed and incubated at 37° C. for 20 mins to make the conjugate using 'sticky sequence' technology (FIG. 4; M: Marker, 1:tP19 aptamer, 2: CCR5 aptamer, 3: tP19-CCR5 bi-specific RNA aptamers). The 'sticky sequence' technology successfully conjugated tP19 and CCR5 aptamers for bi-specific RNA aptamers.

3. Target Binding Assay

To test the binding of bi-specific RNA aptamers (tP19-CCR5 aptamer) on target cells which is PANC-1, live cell imaging was performed. tP19 was labeled with Cy3 and CCR5 aptamer was labeled with FAM. 500 nM of bi-specific RNA aptamers was incubated in PANC-1 for 4 hours and took images by confocal microscopy (Red: Cy3, Green: FAM, Blue: Hoechest for nuclear staining). The bi-specific RNA aptamers stayed on the surface of PANC-1, not internalized.

4. Cytotoxic T Lymphocyte Assay (CTL) of Bi-Specific RNA Aptamers (tP19-CCR5).

To test tumor cell lysis by bi-specific RNA aptamers, health human T cells were isolated using CD8 positive selection kits (Stem cell, #18053). After isolation, CD8 T cells enrichment was confirmed with flow cytometry.

Target cells, PANC-1 were labeled with Calcein-AM which is green fluorescence dye in living cells. Effector cells were isolated CD8 T cells and target cells were PANC-1. 500 nM of bi-specific RNA aptamers were incubated with the cells in media without Phenol Red and FBS for 8 hours at E:T ratio=20:1. Four different experimental groups were setup to test whether the isolated CD8 T cells attack foreign cells. tP19; tP19 aptamer in CD8 Tcells:PANC-1 (E: T ratio=20:1). CCR5; CCR5 aptamer in CD8 Tcells:PANC-1 (E: T ratio=20:1). tP19-CCR5; bi-specific tP19-CCR5 aptamer in CD8 Tcells:PANC-1 (E: T ratio=20:1). CC; without aptamers in CD8 T cells: PANC-1 (E: T ratio=20:1).

The released fluorescence was measured by fluorescence plate reader.

Specific lysis was calculated by the following formulation.

Specific lysis (%)=(experimental release-spontaneous release control/maximum release control-spontaneous release control)×100.

Figure 9:
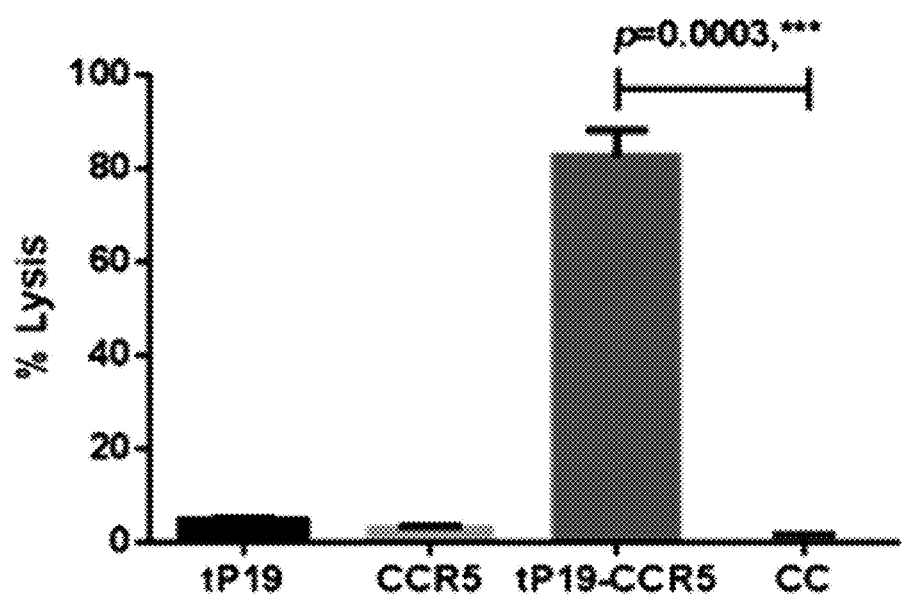
FIG. 9. Chart showing results of bi-specific aptamer cytotoxic T-cell assay.
Figure 13:
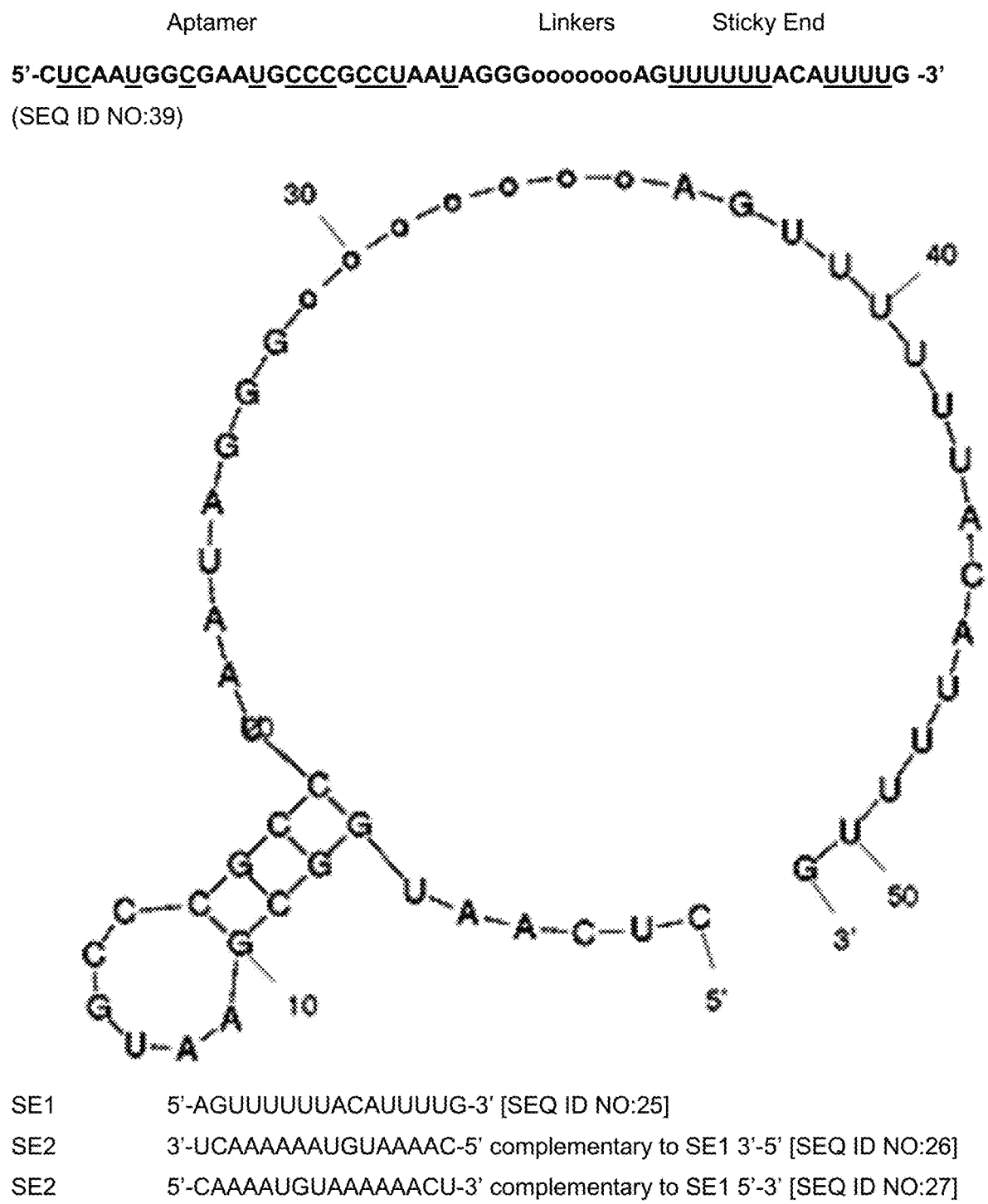
FIG. 13. Aptamer tP19 conjugated to sticky end (SE) nucleic acid sequence with intermediate seven C3 carbon spacer, and predicted structure. SE1-3-sticky end sequences and complementary sequences.

The bi-specific RNA aptamers induced PANC-1 lysis up to 80% (FIG. 9).

Figure 7:
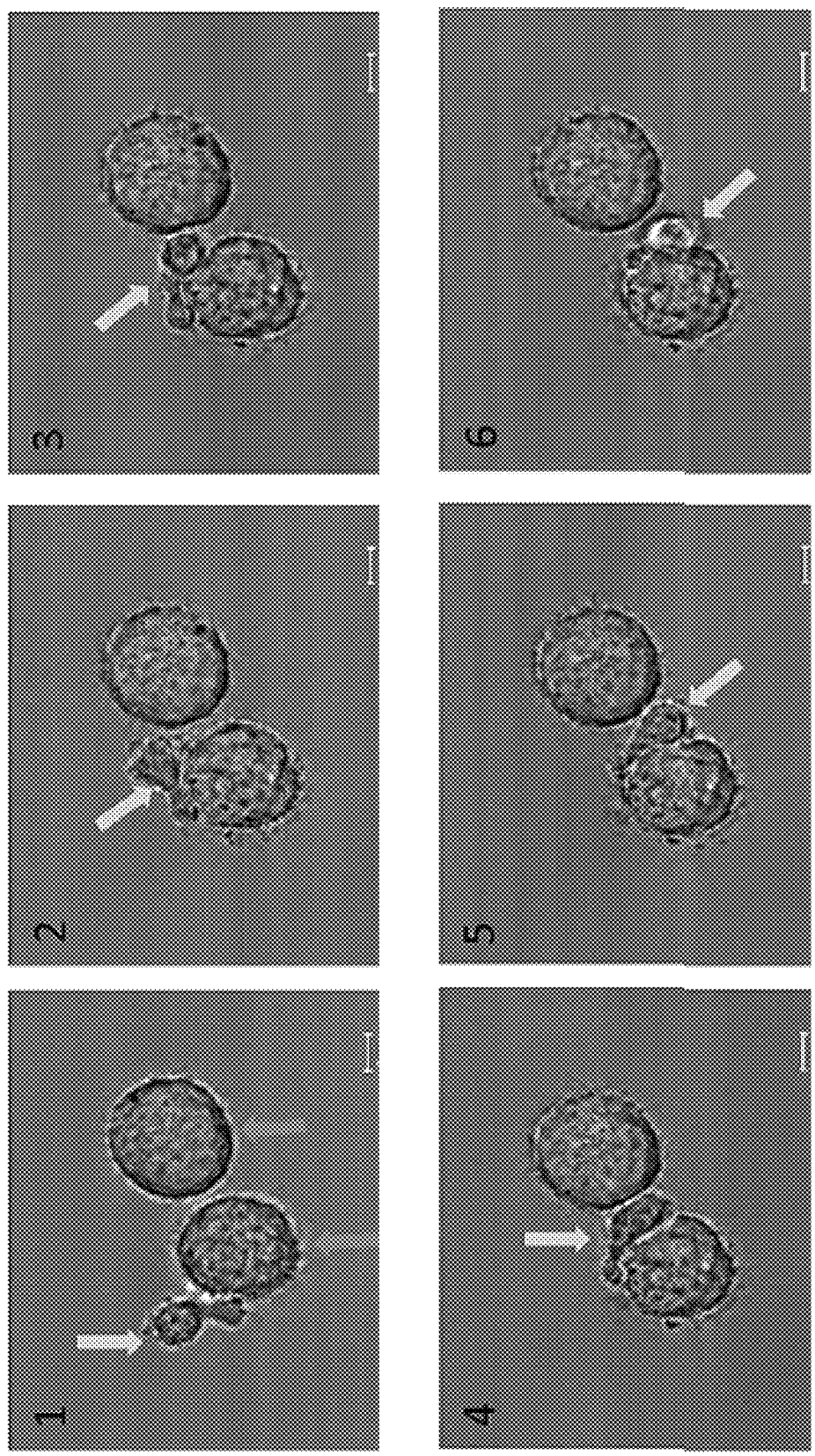
FIG. 7. Sequential images of T cells probing tumor cells. CD8 T cells were incubated with PANC-1 in the presence of P19-CCR5 bi-specific aptamer. Arrows to smaller cells indicates CD8 T cells. Arrows to larger cells indicates PANC-1 cells. The scale bar on the lower right hand corner of each image represents 5 microns.
Figure 8:
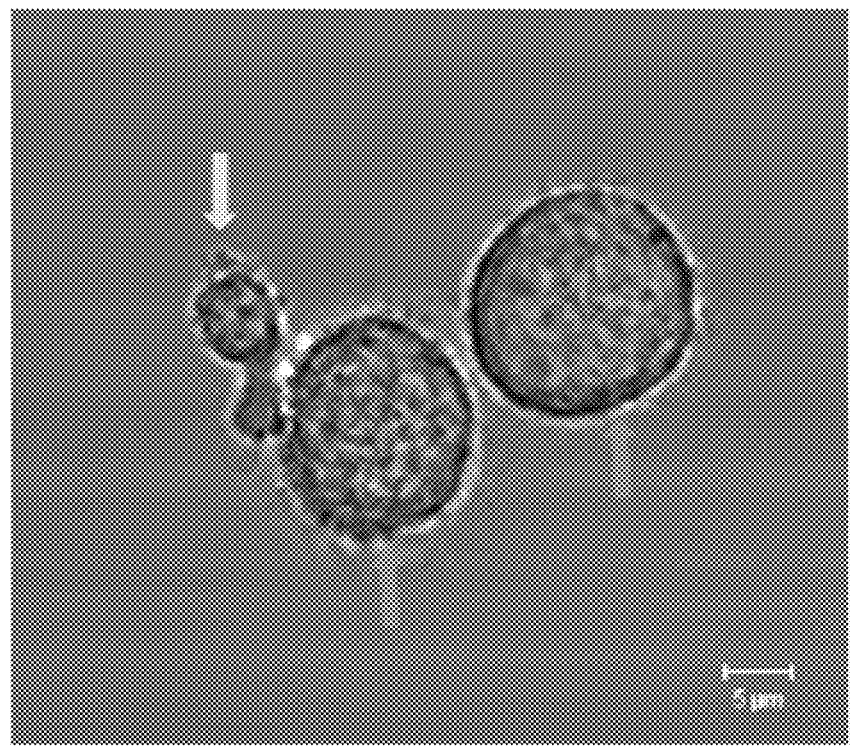
FIG. 8. Micrograph illustrating formation of immunological synapse.

Real-time video microscopy showed that the bi-specific aptamer was capable of attracting T-cells to PANC-1 cells creating a complex of T-cell, bi-specific aptamer and PANC-1 cells that led to rapid and efficient lysis of PANC-1 cells (e.g. see FIGS. 7 and 8).

Example 2: mHSP70/CCR5 Bi-Specific Aptamer

P19 (SEQ ID NO:2) conjugated to sticky sequence via polycarbon linker: GGGAGAfCAAGAAfUAAAf-CGfCfUfCAAfUGGfCGAAfUGfCfCfCGfCfCfUAAfUf-AGGGfCG fUfUAfUGAfCfUfUGfUfUGAGfU-fUfCGAfCAGGAGGfCfUfCAfCAAfCAGGfCoooooooom Am GfUfUfUfUfUfUmAfCmAfUfUfUfUmG [SEQ ID NO:19]

P1 (SEQ ID NO:4) conjugated to sticky sequence via polycarbon linker: GGGAGAfCAAGAAfUAAAf-CGfCfUfCAAfUGfCGfCfUGAAfUGfCfCfCAGfCfCfGfU-GAAAGf CGfUfCGAfUfUfUfCfCAfUfCfCfU-fUfCGAfCAGGAGGfCfUfCAfCAAfCAGGfCoooooooom Am GfUfUfUfUfUfUmAfCmAfUfUfUfUmG [SEQ ID NO:20]

CCR5 aptamer (G3): GGGAGGAfCGA-fUGfCGGGfCfCfUfUfCGfUfUfUGfUfU-fUfCGfUfCfCAfCAGAfCGAfCfUfC GfCfCfCGAooooofCmAmAmAmAfUmGfUmAmAmA-mAmAmAfCfU [SEQ ID NO: 18]

Bold: sticky sequence. fU and fC: 2'F modified pyrimidines. mA and mG: 2' O methylated purines, o: C3 carbon linker.

P19 (SEQ ID NO:2) and P1 (SEQ ID NO:4) are mHSP70 binding aptamers, each capable of internalising upon binding of mHSP70 at the cell surface. They are described in WO2013/154735.

The CCR5 binding aptamer G3 (SEQ ID NO:9) is described in Zhou et al., 2015, Chemistry & Biology 22, 379-390 Mar. 19, 2015 and in co-pending U.S. patent application Ser. No. 14/801,710.

Formation of bi-specific aptamers capable of binding mHSP70 and CCR5:

P19 or P1 conjugated to the sticky sequence via a polycarbon linker is folded in binding buffer (phosphate-buffered saline solution [DPBS] without $Ca^{2+}$ and $Mg^{2+}$, 5 mM $MgCl_2$) at 95° C. for 5 mins and slowly cooled down. CCR5 aptamer conjugated to the sticky sequence via a polycarbon linker is folded in binding buffer (DPBS with $MgCl_2$ and $CaCl_2$)) at 65° C. for 5 mins and slowly cooled down. The same concentration of P19 or P1 and CCR5 aptamers is mixed and incubated at 37° C. for 20 mins to make the bi-specific aptamer using 'sticky sequence' technology.

Example 3: Mass-Spectrometry Based Identification of Aptamer Binding Cell-Surface Proteins One key challenge in cancer biomarker discovery is the identification of targets that are intracellular in normal cells but are exposed on the surface of tumor cells. Targets with these characteristics can increase the therapeutic specificity and affinity of candidate biomarkers for cancer cells, leading to the development of anti-cancer therapeutics, diagnosis and theragnostics. Herein, we describe methods for identifying tumor-associated proteins on living cells as cancer biomarkers, using blind Systematic Evolution of Ligands by EXponential enrichment (SELEX) and tandem mass spectrometry. As proof of principle, a proteomic platform to select mislocated targets specifically expressed on pancreatic cancer plasma membrane have been developed using RNA aptamers. Vimentin was identified as binding targets. This technique could be applied to a variety of cancer types.

1. Introduction

Aptamers, which are small structured single-stranded RNAs, are powerful and emerging molecular tools for identifying biomarkers in cancer, as they can be selected to recognize a wide variety of targets including proteins, cultured cells, and whole organisms [1-6]. Aptamers are generated by Systematic Evolution of Ligands by EXponential enrichment (SELEX) and hold their three-dimensional structures by well-defined complementary nucleic acid sequences [7, 8]. As aptamers adopt complex structures to bind targets with high affinity and specificity, they offer significant advantages over antibodies: better structural stability, low toxicity, low immunogenicity and greater safety [7, 8]. Moreover, the affinity and specificity of aptamers is comparable to, or even more greater than, the affinity and specificity of antibodies [9]. Another advantage over antibodies is that aptamers can be fine-tuned and reduced in size after selection through chemical synthesis.

Mass spectrometry based proteomics allows profiling of protein identification, providing an important source for the development of novel therapeutics and diagnostic targets [10]. The strength of tandem mass spectrometry (MS/MS) is that it provides extensive sequence information over the whole length of a protein chain in a single series of experiments that involves minimal effort directed toward the separation and purification of oligopeptide fragments [10].

The proteins which are selectively expressed on the plasma membrane of cancer cells can be used to further our understanding of tumor development. Several plasma membrane-associated proteins expressed specifically on tumor cells have been described, including the following: Heat-shock protein 70 (HSP70) [11, 12], heat-shock protein 90 (HSP90) [13, 14], glucose-regulated protein 78 (GRP78) [15, 16], vimentin [17], nucleolin [18, 19], and feto-acinar pancreatic protein (FAPP) [20]. Since Berezovski et al. initiated aptamer-facilitated biomarker discovery (AptaBiD) [21], the identification and validation of biomarkers for therapeutics and the diagnosis of cancer become substantially increased. This development has opened the door for drug discovery. For the cancer-biomarker discovery by aptamers, cell-SELEX procedure was employed to identify new cancer surface proteins. Several plasma membrane-associated proteins expressed specifically on tumor cells have been identified by aptamers, including the following: Alkaline phosphatase placental-like 2 (ALPPL-2) [22], siglec-5 [23], stress-induced phosphoprotein 1 (STIP1), protein tyrosine kinase 7 (PTK7) [25]. In pancreatic cancer, alkaline phosphatase placental-like 2 (ALPPL-2) and cyclophilin B have also been reported to be novel candidate biomarkers that are retrieved by RNA aptamers [22, 26].

Herein, we present a detailed methodology to identify putative biomarkers on the tumor cell plasma membrane using RNA aptamers in a blind SELEX approach that involves tandem MS/MS.

2. Methods and Results 2.1. Chemicals and Materials

Ultra-purified (Milli-Q) water, Acetonitrile ($CH_3CN$, Burdick and Jackson HPLC grade), Ammonium bicarbonate ($NH_4HCO_3$. Sigma), Dithiothreitol (DTT, Sigma), Iodoacetamide (IAA, Sigma), Trypsin (Promega modified trypsin, sequencing grade), Trifluroacetic acid (TFA, Sigma).

2.2. Naïve Whole-Cell SELEX (Blind SELEX)

The following cell lines were purchased from the American Type Culture Collection (ATCC) for use as targets for SELEX and internalization assay; PANC-1 (CRL-1469), CFPAC-1 (CRL-1918), MIA PaCa-2 (CRL-1420), BxPC-3 (CRL-1687) and AsPC-1 (CRL-1682). Huh-7 cells were purchased from Japanese Collection of Research Biore-sources (JCRB). The cells were cultured according to the cell bank's instructions.

The SELEX cycle was performed basically as described by Tuerk and Gold [8]. In vitro selection was carried out essentially as described [27], with a few modifications for this study. The human pancreatic adenocarcinoma, PANC-1, cells were used as target cells for the aptamer selection. To remove background/irrelevant binding, the hepatocellular carcinoma cell line Huh7 was used for the counter-selection step. A library of 2'F RNAs was used to increase nuclease resistance and enhance aptamer folding. To isolate 2'F RNA aptamers binding to intact cells, a library of approximately 440 different 2'F RNA molecules, containing a 40-nt-long random sequence flanked by defined sequences, was screened by SELEX. For the first round, 6 nmols of the RNA library was incubated for 30 minutes at 37° C. with negative (Huh7) cells in 1 ml binding buffer (phosphate-buffered saline solution [PBS] without $Ca^{2+}$ and $Mg^{2+}$, 5 mM $MgCl_2$, 0.01% BSA, yeast tRNA (100 μg/ml). The supernatant was recovered and incubated on the target cells for 1 hour at 37° C. RNAs that bound to target cells were recovered, amplified by RT-PCR and in vitro transcription, and used in the following selection rounds. In subsequent rounds, the RNA concentration was reduced by 10 fold and the incubation time was reduced to create more stringent conditions. The enriched pools were cloned after 14 cycles of selection.

Figure 17A:
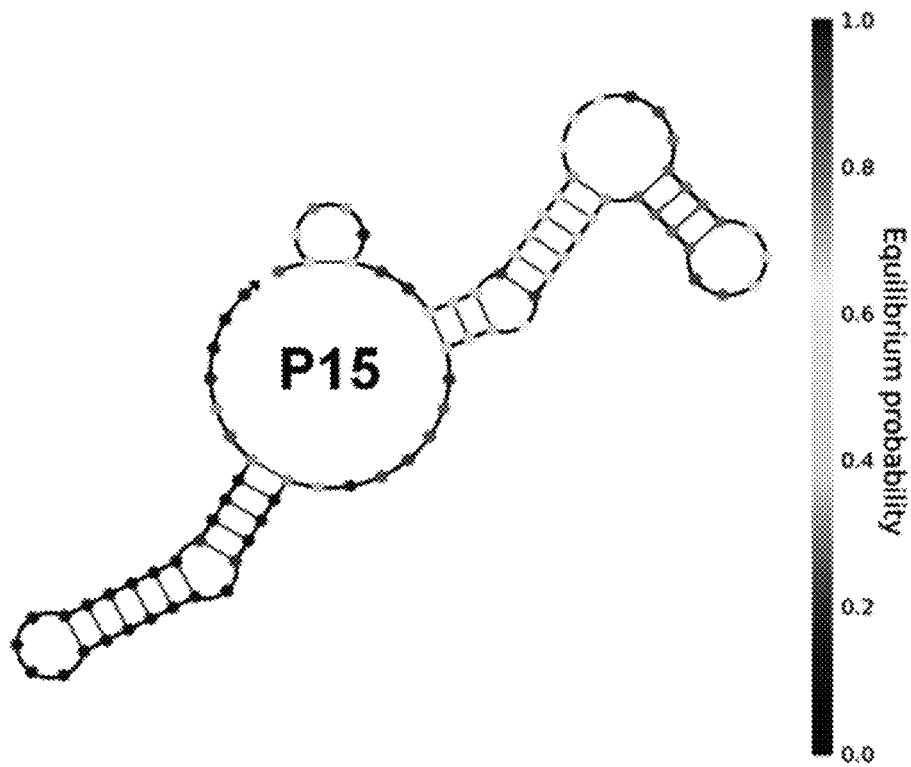
FIGS. 17A-17D. Secondary structures and flow cytometry binding assay.

A highly enriched aptamer, P15, was selected: GGGA-GACAAGAATAAACGCTCA AAGTTGCGGCC-CAACCGTTTAATTCAGAATAGTGT-GATGCCTTCGACAGGAGGCTCAC AACAGGC (SEQ ID NO:36). Minimum energy structural analyses of the selected aptamers were carried out using the NUPACK software (at website www.nupack.org) (FIG. 17A). As depicted, the calculated secondary structures of the RNA aptamers contained several stem-loop regions.

2.3. Flow Cytometry-Based Binding Assays

Figure 17B:
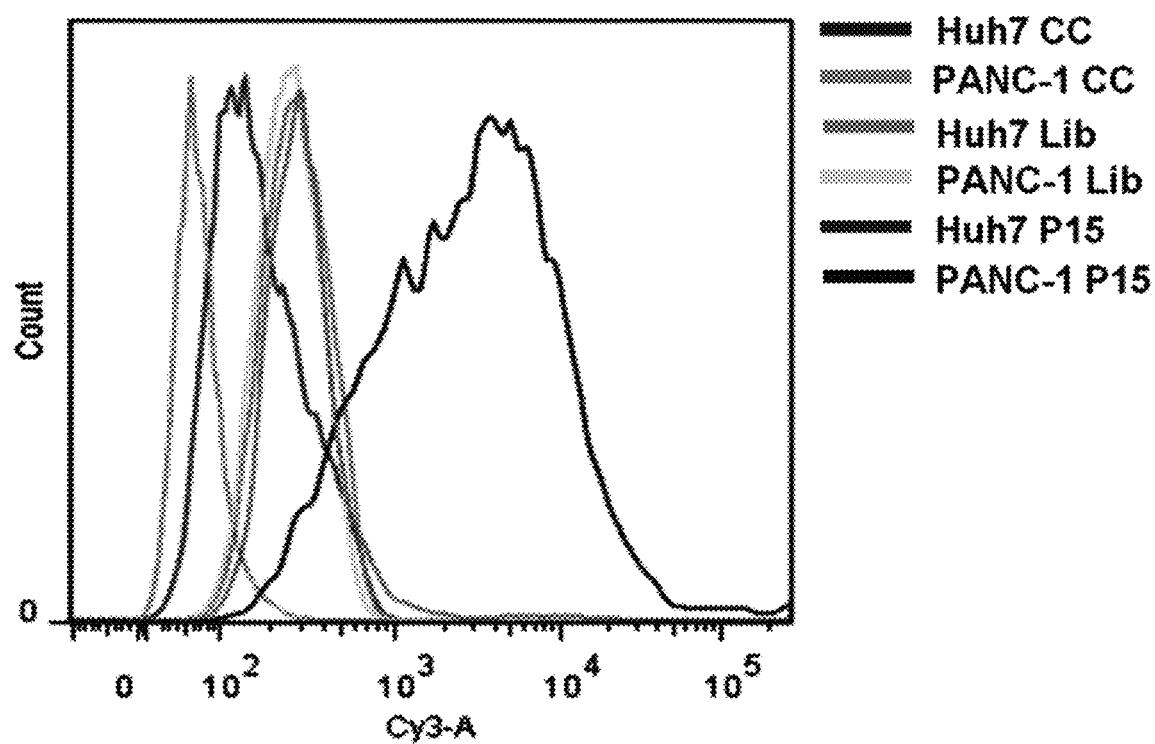
Figure 17C:
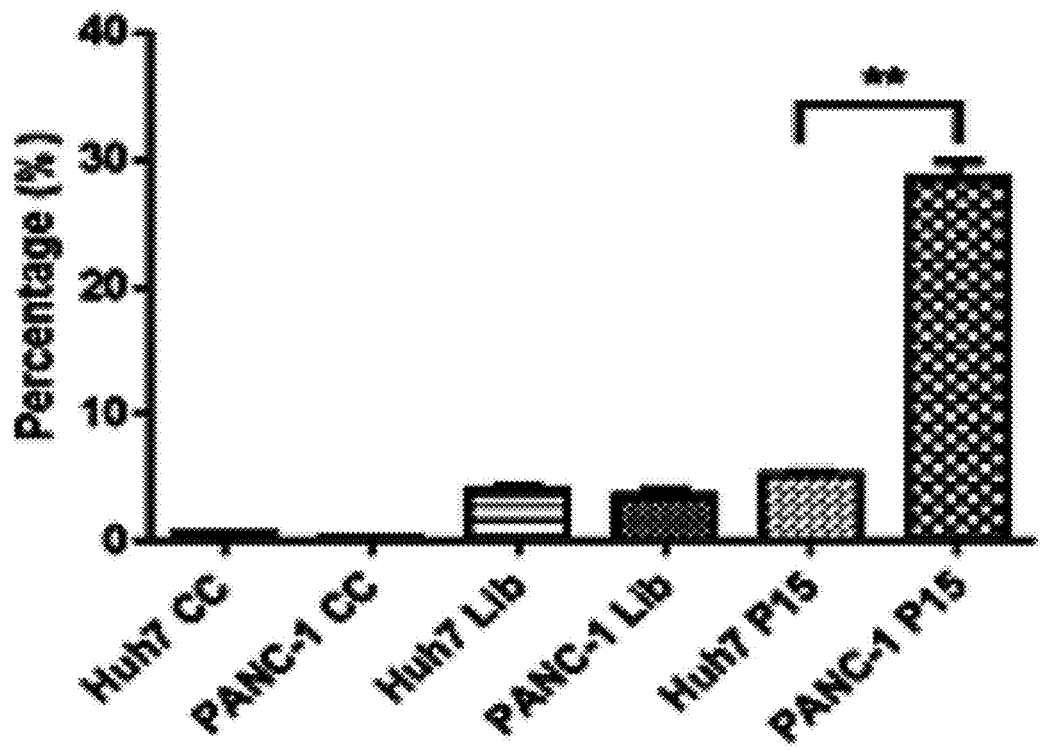
Figure 18:
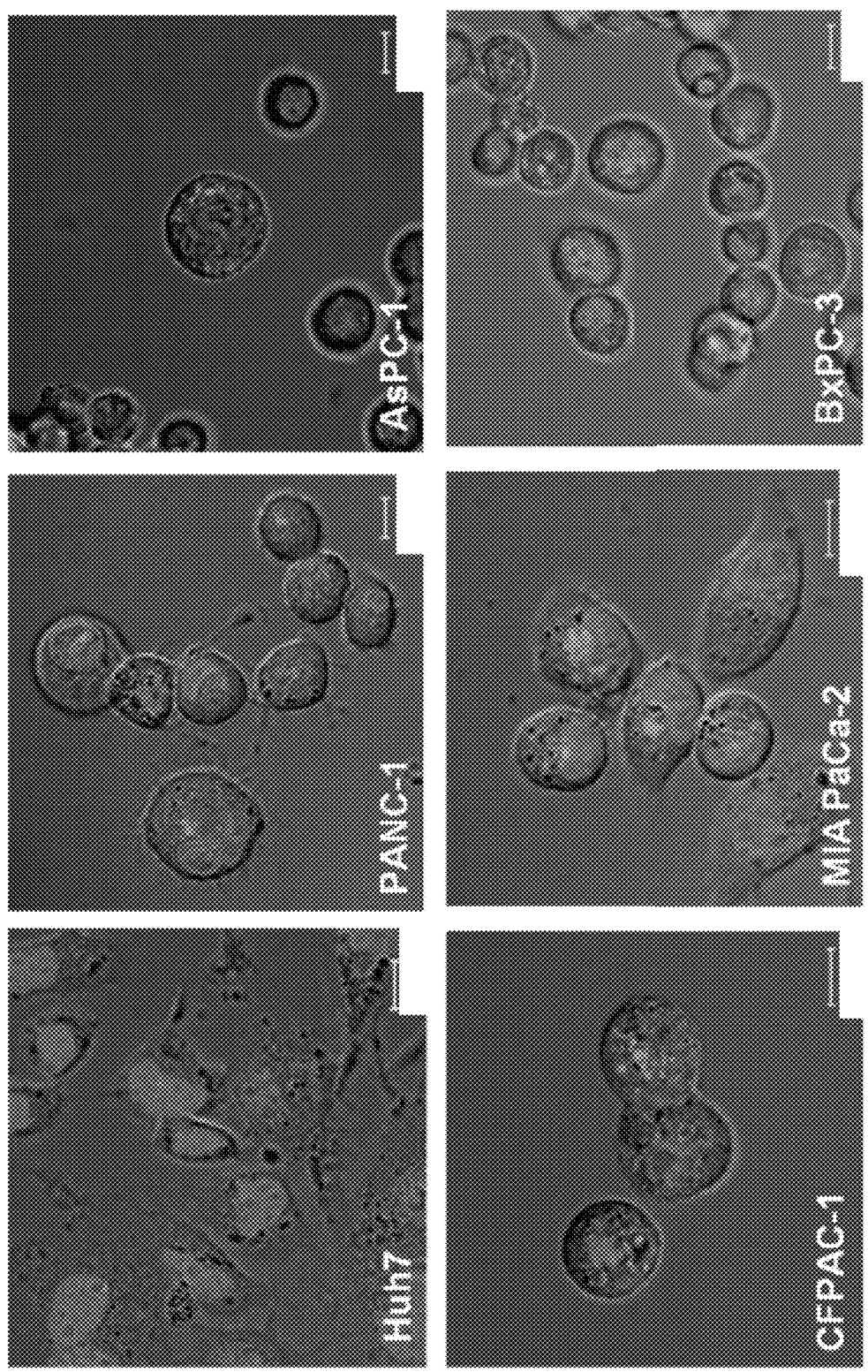
FIG. 18. Fluorescence micrographs showing cell internalization. The pancreatic cell lines PANC-1, AsPC-1, CFPAC-1, MIA PaCa-2 and BxPC-3 were treated with 100 nM of the Cy3-labeled P15 aptamer and analyzed by confocal microscopy. All of the pancreatic lines showed punctate regions of Cy3 labeling. The Huh7 negative cells were also treated with 100 nM of Cy3-labeled P15 aptamers to show negative staining. Red: Cy3-labeled RNA. Blue: Hoechst 33342. The scale bar on the lower right hand corner of each image represents 10 microns.

Aptamer binding was also assessed by flow cytometry. For the assay, the PANC-1 cells and Huh7 cells were detached using a non-enzymatic cell dissociation solution, washed with PBS and suspended in binding buffer. Next, Cy3-labeled aptamers at 200 nM were added and incubated with $2\times10^5$ cells for 30 minutes at 37° C. Cells were washed with binding buffer and immediately analyzed by Fortessa flow cytometry (BD). Each flow-cytometry assay was performed in triplicate. The data were analyzed with FlowJo software. The flow cytometry analyses of P15 confirmed enriched cell surface binding to PANC-1 cells, compared to the initial non-selected RNA library. PANC-1 cells treated with Cy3-labelled P15 aptamers demonstrated significantly higher levels of positively stained cells (P<0.01) (FIGS. 17B-17C). The binding affinity of P15 to PANC-1 cells was determined to be 16.05 nM. To verify the specificity of P15 to pancreatic cancer cells, a panel of four different pancreatic cancer cell lines (AsPC-1, CFPAC, MIA PaCa-2 and BxPC-3) was treated with Cy3-labelled P15 aptamer. Interestingly, punctate cytoplasmic staining was observed in pancreatic cancer cell lines, but no staining was observed in negative control cells (Huh7) (FIG. 18).

Figure 17D:
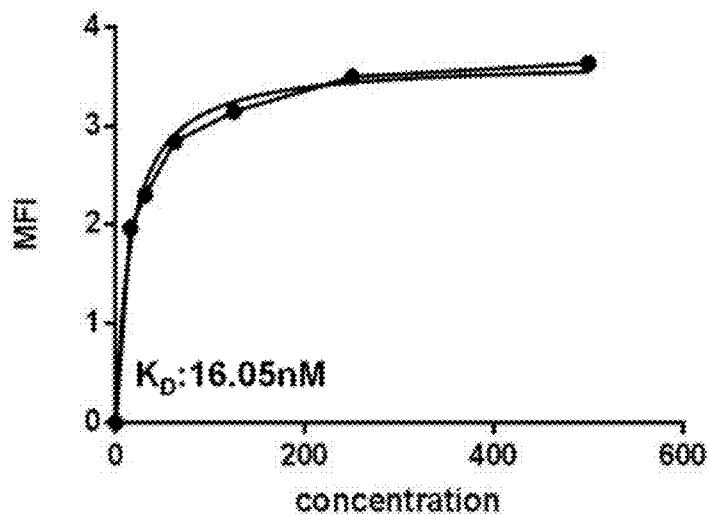

To determine the apparent dissociation constant ($K_D$) of aptamers to PANC-1 cells, the mean fluorescence intensity (MFI) was calculated for each concentration and for the unselected library controls. The values for the controls were considered to be background fluorescence and were subtracted from the values for the aptamers, as previously described by Sefah et al. The dissociation constants were calculated using a one-site binding model. The non-linear curve regression was performed using Graph Pad Prism (GraphPad Software, La Jolla, California, USA). The binding affinities of P15 aptamers were measured to 16.05 nM (FIG. 17D).

2.4. Live-Cell Confocal Imaging.

For the aptamer internalization studies, $1\times10^5$ cells were seeded in 35 mm glass-bottom dishes (MatTek, Ashland, MA, USA) and grown in medium for 24 hrs. The RNAs were labeled with Cy3 using the Cy3 Silencer siRNA labeling kit (Ambion, TX, USA.). Cy3-labeled RNAs were added to the cells at 100 nM and incubated for 1 hour. The images were taken using a Zeiss LSM 510 Meta Inverted 2 photon confocal microscope system using a C-Apo 40×/1.2 NA water immersion objective.

Cy3-labelled P15 aptamers got internalized to the target cells (PANC-1), but no staining was observed in negative cells (Huh7). To verify the specificity of the aptamers to pancreatic cancer cells, a panel of four different pancreatic cancer cell lines AsPC-1, CFPAC, MIA PaCa-2 and BxPC-3 were treated with Cy3-labelled P15 aptamers. Punctate cytoplasmic staining of Cy3-labeled aptamers was observed. The pattern of cytoplasmic staining is suggestive of endocytic internalization of the aptamers.

2.5. Affinity Purification of Target Membrane Proteins Using RNA Aptamer.

As the aptamer were internalized in cells, the cell membrane proteins were isolated from the cells to identify the target epitope of the aptamer. Biotinylated aptamers, together with the associated protein complexes, were immobilized using a pull-down process. The selected RNA aptamers and irrelevant RNAs were labeled with biotin at their 3' ends. The target membrane proteins were isolated using procedures described by Daniels et al. [4]. Briefly, A monolayer of cells (plated at $1\times10^6$ cells per 100 mm dish) was washed three times at 4° C. with PBS containing 1 mM $CaCl_2$) (pH 7.4). Three ml of hypotonic buffer (10 mM Tris HCl [pH 7.5] containing 5 mM KCl and 0.5 mM $MgCl_2$ with protease inhibitors) was added to the cell monolayer for 30 minutes 4° C. before the cells were harvested by scraping. The stripped cells were homogenized on ice in a sucrose solution (0.25 M). Whole cells and nuclei were removed by centrifugation (1,000×g for 10 minutes at 4° C.). The supernatant was recentrifuged to pellet the membrane component (105,000×g for 10 minutes at 4° C.). The pellet was solubilized at 4° C. with rotation in extraction buffer (10 mM Tris HCl [pH 7.5] containing 200 mM NaCl, 0.1%[v/v] Triton X-100, 1 mM $MgCl_2$, 1 mM $CaCl_2$) and protease inhibitors). The extracted cell-surface membrane was incubated at 4° C. for 2 hours with biotinylated aptamers (1 nmol), irrelevant RNAs (1 nmol) and streptavidin beads in affinity purification buffer (extraction buffer containing 0.5 μg/μl BSA and 4%[v/v] glycerol). The beads were washed in extraction buffer for 30 minutes at 4° C. before the bound protein was eluted using elution buffer (10 mM Tris·HCl [pH 7.5] containing 1 M NaCl, 5 mM EDTA and 0.1%[v/v] Triton X-100).

The retrieved proteins were separated by SDS-PAGE followed by Coomassie staining to visualize the resolved protein bands (FIG. 19A). The highest matching peak retrieved from P15-treated cells matched a known peak for vimentin by tandem mass spectrometry (MASS-SPEC) spectrum (FIG. 19B). To confirm the MASS-SPEC results, a competition assay with vimentin antibodies was performed by live cell confocal and flow cytometry. Fluorescence intensity was measured by confocal microscopy. The antibodies to vimentin significantly reduced the binding of P15 to target cells, P<0.05 (FIG. 19C). These results strongly suggest the P15 bound to plasma membrane expressing vimentin on cancer cells.

2.6. Protein Digestion.

In-gel or in-solution digestion was used for protein purification and analyzed by mass spectrometry for peptide fingerprinting. After polyacrylamide gel electrophoresis (SDS-PAGE), the aptamer-retrieved protein bands were excised and in-gel digested with optimization [29]. Briefly, the gel band was cut into small pieces and destained with destaining solution (200 mM NH$_4$HCO$_3$ in 50% acetonitrile) for 20 minutes at 37° C. To complete the destaining, the destaining step was repeated after discarding the supernatant. The gel samples were dried in a vacuum concentrator (SpeedVac). The reducing buffer (10 mM DTT in 100 mM NH$_4$HCO$_3$. prepared immediately before use) was added to the dried gel samples and incubated for one hour at 56° C. After removal of the excess reducing buffer, the same volume of alkylating solution (100 mM IAA, prepared immediately before use) was added for 30 minutes at room temperature in the dark. After removal of the supernatant, the gel pieces were washed twice with 200 mM NH$_4$HCO$_3$. To dehydrate the sample, acetonitrile was added for 10 minutes at room temperature. When the gel pieces turned white, the acetonitrile was removed and the gel pieces were re-swelled with 200 mM NH$_4$HCO$_3$ for 10 minutes at room temperature. After removal of the supernatant, the dehydration with acetonitrile was repeated. The gel pieces were then dried in the vacuum concentrator. The digestion buffer (50 ng/μl trypsin in 1 mM HCl/100 mM NH$_4$HCO$_3$. prepared immediately before use) was added to the dried gel pieces for 10 minutes to re-swell the gel pieces. After removing the excess trypsin solution from the samples, 200 mM NH$_4$HCO$_3$ was added to cover the gel pieces and the samples were incubated overnight at 37° C. The samples were then quenched with 1/10 volume of quenching buffer (1:9 TFA: Milli-Q water). The supernatant was saved for the next step. The extraction buffer (0.1% TFA in 60% acetonitrile) was added to cover the gel pieces and incubated for 40 minutes at 37° C. The supernatant containing the extraction buffer was then extracted and combined with the quenched solution supernatant from the previous step. The volume of the combined supernatant was reduced to 20 μl by evaporation.

2.7. Liquid Chromatography Tandem MS/MS (LC-MS/MS) Q-TOF.

An Agilent 6520 Q-TOF mass spectrometer equipped with a Chip Cube source was used for LC/MS/MS analyses. A C18 chip with a 43 mm analytical column and a 40 nl trapping column (ProtID-Chip-43, Agilent G4240-62005) was used. Digested samples (10-15 μl) were loaded onto the column at 6 μl/minute in 99% Buffer A (0.1% Formic Acid in water)/1% Buffer B (0.1% Formic Acid in Acetonitrile) with an extra 8 μl wash volume. The gradient was from 3% to 35% Buffer B over 8 minutes and then 35% to 90% Buffer B over 1 minute. The total run time, including injection, was 15 minutes. The voltage was adjusted to the 1850V to 2000V range. The X! Tandem search engine (http://www.thegpm.org/TANDEM/index.html) was used to search the peptide MS/MS spectrum. The dataset was then processed using the Scaffold program (http://www.proteomesoftware.com) to visualize the results. SWISS Prot or NCBI were used to obtain the detailed protein annotation. The highest matching peak detected from P15-treated cells matched a known peak for vimentin (FIG. 19B).

2.8. Competition Assays for Validation of Target.

For the aptamer-antibody competition assay, Cy3-labeled P15 aptamer was used to compete with vimentin antibodies (Sigma, V6630). The cells (1×10$^5$) were seeded in 35 mm glass-bottom dishes (MatTek, Ashland, MA, USA) and grown in medium for 24 hours. Cells were preincubated with vimentin antibodies, at 1 uM, for 20 minutes before Cy3-labeled P15, at 200 nM, was added. The cells were incubated for 2 hours at 37° C. The images were taken using a Zeiss LSM 510 Meta Inverted 2-photon confocal microscope system using a C-Apo 40×/1.2 NA water immersion objective. The arbitrary fluorescence intensity was quantified in the presence of competitors using confocal microscopy and analyzed statistically. Student's t test was used for statistical significance analysis (P<0.05) (FIG. 19C).

For competition assay by flow cytometry, PANC-1 cells were detached using Accutase (Sigma-Aldrich), washed with DPBS, and suspended in binding buffer (phosphate-buffered saline solution [DPBS without Ca$^{2+}$ and Mg$^{2+}$, Corning, Tewksbury MA], 5 mM MgCl$_2$). Next, PANC-1 cells were pre-incubated with vimentin antibodies, at 1 μM, for 20 minutes on ice. After pre-incubation with vimentin antibodies, Cy3-labeled aptamers at 200 nM of final concentration were added and incubated with 2×10$^5$ cells for 30 minutes ice. Cells were washed with DPBS three times and immediately analyzed by Fortessa flow cytometry (BD Biosciences, San Jose, CA). 4'6'-diamidino-2-phenylindole (DAPI) (1 μg/ml) was used to identify and exclude dead cells. Data were analyzed with FlowJo software (FlowJo, Ashland, OR).

3. Discussion.

We have presented protein biomarker discovery platforms that use RNA aptamers. The current approach, which included aptamer selection against cells, cell membrane protein extraction, and tandem MS/MS, has allowed for the identification of novel proteins translocated to the plasma membrane. Untargeted SELEX, called "blind SELEX", allows for the generation of highly enriched RNA aptamers against target cells such as primary cells, normal cells, cancer cells, and tissue-specific cells. This strategy also allows us to distinguish different cancer cell types. The enriched RNA aptamers specifically bind to the cell membrane proteins with high affinity. The cell membrane is retrieved with affinity purification using the RNA aptamer. The proteins are then identified by tandem MS/MS. Because tandem MS/MS does not require the samples be purified to a high degree of homogeneity and works well as long as the target protein is a major component of the mixture [30], it the best choice in protein biomarker discovery. When the candidates of target proteins are identified, the interactions of RNA aptamers with proteins can be validated by surface plasmon resonance (SPR), gel shift assays or enzyme-linked immunoassays (ELISA).

The list of currently identified cancer cell membrane-associated proteins includes the following: HSP70, HSP90, GRP78, vimentin, nucleolin, and FAPP. HSP70 is a chaperone with ATPase activity that is found in the intracellular compartment in normal cells [31], but is translocated to the plasma membrane of tumor cells [11, 12]. HSP90 is a molecular chaperone protein that assists proteins in proper folding; however, it is not only localized intracellularly but also expressed on the plasma membrane of tumor cells [13, 14]. GRP78 is an endoplasmic reticulum (ER) protein involved in protein folding that is up-regulated and localized on the tumor cell surface [15, 16]. Nucleolin is a nucleolar protein involved in the regulation of proliferation, cytokinesis, and replication [18, 19]. Nucleolin is also expressed on the surface of tumor-related blood vessels, but not on mature vessels or capillaries [18]. FAPP has been identified as another membrane-associated protein in pancreatic cancers [20, 32]. Vimentin belongs to the group of intermediate filament proteins, which form the cytoskeleton and are associated with the nucleus, mitochondria, and ER [33]. However, vimentin expression is also correlated with the epithelial mesenchymal transition (EMT) during tumor progression [34]. Vimentin was also identified in pancreatic cancer. Even though the molecular mechanisms of the presentation of these proteins on the cancer surface still need to be resolved, it might be of interest to find novel membrane-associated proteins for targeting molecules using RNA aptamers. The approach described herein allows for the identification of novel protein biomarkers using RNA aptamers. A key advantage of employing RNA aptamers for biomarker discovery over antibodies is their specificity towards the target proteins, which minimizes off-target binding.

REFERENCES (EXAMPLE 3)

[1] H. Ulrich, M. H. Magdesian, M. J. Alves, W. Colli, J Biol Chem, 277 (2002) 20756-20762; [2] J. Wang, H. Jiang, F. Liu, RNA, 6 (2000) 571-583; [3] M. Blank, T. Weinschenk, M. Priemer, H. Schluesener, J Biol Chem, 276 (2001) 16464-16468; [4] D. A. Daniels, H. Chen, B. J. Hicke, K. M. Swiderek, L. Gold, Proceedings of the National Academy of Sciences of the United States of America, 100 (2003) 15416-15421; [5] B. J. Hicke, C. Marion, Y. F. Chang, T. Gould, C. K. Lynott, D. Parma, P. G. Schmidt, S. Warren, J Biol Chem, 276 (2001) 48644-48654; [6] D. S. Wilson, J. W. Szostak, Annu Rev Biochem, 68 (1999) 611-647; [7] A. D. Ellington, J. W. Szostak, Nature, 346 (1990) 818-822; [8] C. Tuerk, Methods Mol Biol, 67 (1997) 219-230; [9] N. S. Que-Gewirth, B. A. Sullenger, Gene therapy, 14 (2007) 283-291; D. F. Hunt, J. R. Yates, 3rd, J. Shabanowitz, S. Winston, C. R. Hauer, Proceedings of the National Academy of Sciences of the United States of America, 83 (1986) 6233-6237; G. Multhoff, C. Botzler, M. Wiesnet, E. Muller, T. Meier, W. Wilmanns, R. D. Issels, International journal of cancer. Journal international du cancer, 61 (1995) 272-279; M. Ferrarini, S. Heltai, M. R. Zocchi, C. Rugarli, International journal of cancer. Journal international du cancer, 51 (1992) 613-619; S. J. Ullrich, E. A. Robinson, L. W. Law, M. Willingham, E. Appella, Proceedings of the National Academy of Sciences of the United States of America, 83 (1986) 3121-3125; J. Trepel, M. Mollapour, G. Giaccone, L. Neckers, Nature reviews. Cancer, 10 (2010) 537-549; J. Li, A. S. Lee, Current molecular medicine, 6 (2006) 45-54; A. S. Lee, L. M. Hendershot, Cancer biology & therapy, 5 (2006) 721-722; R. Bhattacharya, A. M. Gonzalez, P. J. Debiase, H. E. Trejo, R. D. Goldman, F. W. Flitney, J. C. Jones, Journal of cell science, 122 (2009) 1390-1400; S. Christian, J. Pilch, M. E. Akerman, K. Porkka, P. Laakkonen, E. Ruoslahti, The Journal of cell biology, 163 (2003) 871-878; V. Fogal, K. N. Sugahara, E. Ruoslahti, S. Christian, Angiogenesis, 12 (2009) 91-100; L. Panicot-Dubois, M. Aubert, C. Franceschi, E. Mas, F. Silvy, C. Crotte, J. P. Bernard, D. Lombardo, M. O. Sadoulet, Neoplasia, 6 (2004) 713-724; M. V. Berezovski, M. Lechmann, M. U. Musheev, T. W. Mak, S. N. Krylov, Journal of the American Chemical Society, 130 (2008) 9137-9143; P. Dua, H. S. Kang, S. M. Hong, M. S. Tsao, S. Kim, D. K. Lee, Cancer research, 73 (2013) 1934-1945; M. Yang, G. Jiang, W. Li, K. Qiu, M. Zhang, C. M. Carter, S. Z. Al-Quran, Y. Li, J Hematol Oncol, 7 (2014) 5; D. Van Simaeys, D. Turek, C. Champanhac, J. Vaizer, K. Sefah, J. Zhen, R. Sutphen, W. Tan, Analytical chemistry, 86 (2014) 4521-4527; D. Shangguan, Z. Cao, L. Meng, P. Mallikaratchy, K. Sefah, H. Wang, Y. Li, W. Tan, Journal of proteome research, 7 (2008) 2133-2139; Y. Tanaka, K. Akagi, Y. Nakamura, T. Kozu, Oligonucleotides, 17 (2007) 12-21; S. Yoon, G. Lee, D. Han, J. Y. Song, K. S. Kang, Y. S. Lee, Antiviral research, 88 (2010) 19-24; K. Sefah, D. Shangguan, X. Xiong, M. B. O'Donoghue, W. Tan, Nature protocols, 5 (2010) 1169-1185; A. Shevchenko, H. Tomas, J. Havlis, J. V. Olsen, M. Mann, Nature protocols, 1 (2006) 2856-2860; J. E. Fitton, A. Dell, W. V. Shaw, FEBS letters, 115 (1980) 209-212; I. Horvath, G. Multhoff, A. Sonnleitner, L. Vigh, Biochimica et biophysica acta, 1778 (2008) 1653-1664; L. Benkoel, J. P. Bernard, M. J. Payan-Defais, L. Crescence, C. Franceschi, M. Delmas, M. Ouaissi, B. Sastre, J. Sahel, A. M. Benoliel, P. Bongrand, F. Silvy, L. Gauthier, F. Romagne, D. Lombardo, E. Mas, Molecular cancer therapeutics, 8 (2009) 282-291; E. Fuchs, K. Weber, Annual review of biochemistry, 63 (1994) 345-382; M. I. Kokkinos, R. Wafai, M. K. Wong, D. F. Newgreen, E. W. Thompson, M. Waltham, Cells, tissues, organs, 185 (2007) 191-203.

Example 4: Vimentin/CCR5 Bi-Specific Aptamer

P15 (SEQ ID NO:3) conjugated to sticky sequence via polycarbon linker: GGGAGAfCAAGAAfUAAAf-CGfCfUfCAAAGfUfUGfCGGfCfCfCAAfCfCGfUfU-fUAAfUfUfC AGAAfUAGfUGfUGAfUGfCfCfU-fUfCGAfCAGGAGGfCfUfCAfCAAfCAGGfCooooooom Am GfUfUfUfUfUfUmAfCmAfUfUfUfUmG (SEQ ID NO:21)

CCR5 aptamer (G3): GGGAGGAfCGA-fUGfCGGGfCfCfUfUfCGfUfUfUGfUfU-fUfCGfUfCfCAfCAGAfCGAfCfUfC GfCfCfCGAooooofCmAmAmAmAfUmGfUmAmAmA-mAmAmAfCfU (SEQ ID NO:18)

Bold: sticky sequence. fU and fC: 2'F modified pyrimidines. mA and mG: 2' O methylated purines, o: C3 carbon linker.

P15 is a vimentin binding aptamer capable of internalising upon binding of vimentin at the cell surface, see Example 3.

The CCR5 binding aptamer G3 (SEQ ID NO:9) is described in Zhou et al., 2015, Chemistry & Biology 22, 379-390 Mar. 19, 2015 and in co-pending U.S. patent application Ser. No. 14/801,710.

Formation of bi-specific aptamers capable of binding vimentin and CCR5: P15 conjugated to the sticky sequence via a polycarbon linker is folded in binding buffer (phosphate-buffered saline solution [DPBS] without $Ca^{2+}$ and $Mg^{2+}$, 5 mM $MgCl_2$) at 95° C. for 5 mins and slowly cooled down. CCR5 aptamer conjugated to the sticky sequence via a polycarbon linker is folded in binding buffer (DPBS with $MgCl_2$ and $CaCl_2$)) at 65° C. for 5 mins and slowly cooled down. The same concentration of P15 and CCR5 aptamers is mixed and incubated at 37° C. for 20 mins to make the bi-specific aptamer using 'sticky sequence' technology.

Example 5: HSP90/CCR5 Bi-Specific Aptame

P11 (SEQ ID NO:5) conjugated to sticky sequence via polycarbon linker: GGGAGAfCAAGAAfUAAAf-CGfCfUfCAAAfUGAfUfUGfCfCfCAfUfUfCGGfUfUA-fUGfCfUf UGfCGfCfUfUfCfCfUAAAGAGfCfUfUfCfGAfCAGGAGGfCfUfCAfCAAfCAGGfCooooooom AmGfUfUfUfUfUfUmAfCmAfUfUfUfUmG (SEQ ID NO:22)

P7 (SEQ ID NO:6) conjugated to sticky sequence via polycarbon linker: GGGAGAfCAAGAAfUAAAf-CGfCfUfCAAGGfCfCAfUGfUfUGAAfUGfCfCfCAAf-CfUAAGfC fUfUfUGAGfCfUfUfUGGAGfCfU-fUfCGAfCAGGAGGfCfUfCAfCAAfCAGGfCooooooom Am GfUfUfUfUfUfUmAfCmAfUfUfUfUmG (SEQ ID NO:23)

P6 (SEQ ID NO:7) conjugated to sticky sequence via polycarbon linker: GGGAGAfCAAGAAfUAAAf-CGfCfUfCAAfCAAfUGGfAGfCGfUfUAAAfCGfU-GAGfCfCAfUf UfCGAfCAGGAGGfCfUfCAfCAAf-CAGGfCooooooomAmGfUfUfUfUfUfUmAfCmAfUfUfUf UmG (SEQ ID NO:24)

CCR5 aptamer (G3): GGGAGGAfCGA-fUGfCGGGfCfCfUfUfCGfUfUfUGfUfU-fUfCGfUfCfCAfCAGAfCGAfCfUfC GfCfCfCGAooooofCmAmAmAmAfUmGfUmAmAmA-mAmAmAfCfU (SEQ ID NO: 18).

Bold: sticky sequence. fU and fC: 2'F modified pyrimidines. mA and mG: 2' O methylated purines, o: C3 carbon linker.

P11, P7 and P6 are HSP90 binding aptamers capable of internalising upon binding HSP90 at the cell surface.

The CCR5 binding aptamer G3 (SEQ ID NO:9) is described in Zhou et al., 2015, Chemistry & Biology 22, 379-390 Mar. 19, 2015 and in co-pending U.S. patent application Ser. No. 14/801,710.

Formation of bi-specific aptamers capable of binding HSP90 and CCR5: P11, P7 or P6 conjugated to the sticky sequence via a polycarbon linker is folded in binding buffer (phosphate-buffered saline solution [DPBS] without Ca$^{2+}$ and Mg$^{2+}$, 5 mM MgCl$_2$) at 95° C. for 5 mins and slowly cooled down. CCR5 aptamer conjugated to the sticky sequence via a polycarbon linker is folded in binding buffer (DPBS with MgCl$_2$ and CaCl$_2$)) at 65° C. for 5 mins and slowly cooled down. The same concentration of P11, P7 or P6 and CCR5 aptamers is mixed and incubated at 37° C. for 20 mins to make the bi-specific aptamer using 'sticky sequence' technology.

Example 6: Bi-Specific Aptamers in Cancer Immunotherapeutics

Figure 22:
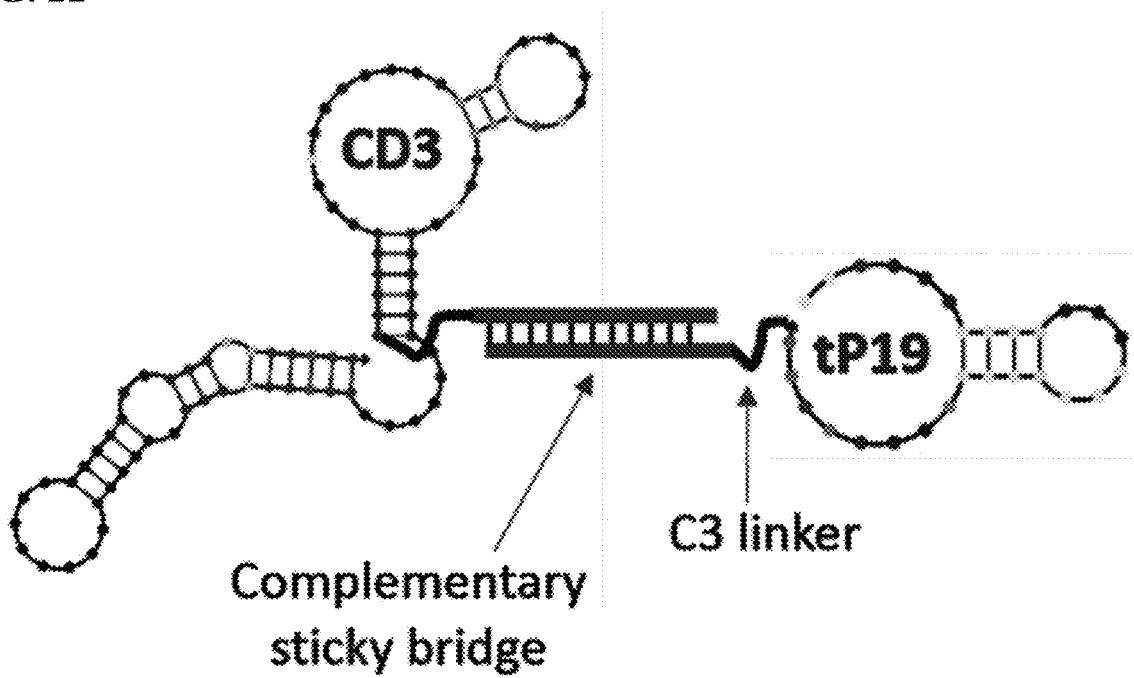
FIG. 22. Schematic structure of bispecific aptamers for T cell engagement. Chemically synthesized CD3ε aptamer (CD3e2) and tP19 aptamer are non-covalently linked via complementary "sticky bridge" sequences to create a bispecific conjugate.

To construct mortalin bi-specific RNA aptamers, truncated mortalin aptamer (tP19) was conjugated to CD3ε aptamer via complementary sticky sequences (FIG. 22).

Figure 23A:
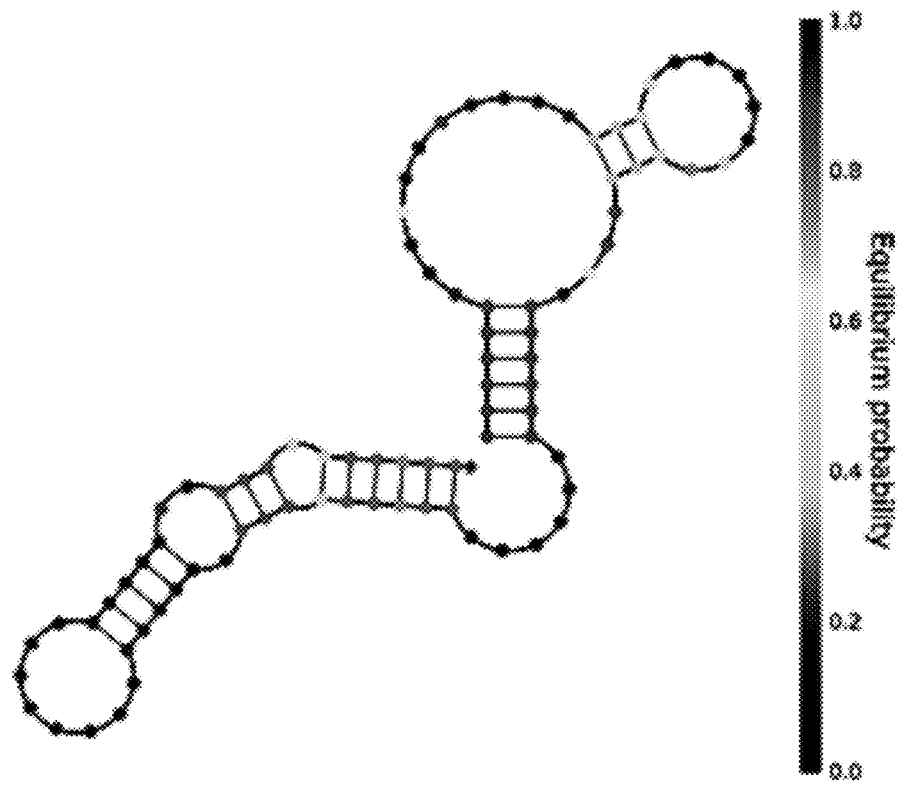
FIGS. 23A-23B. C3e2 (FIG. 23A) and C3e3 (FIG. 23B) both show multiple stem-loop structures.
Figure 23B:
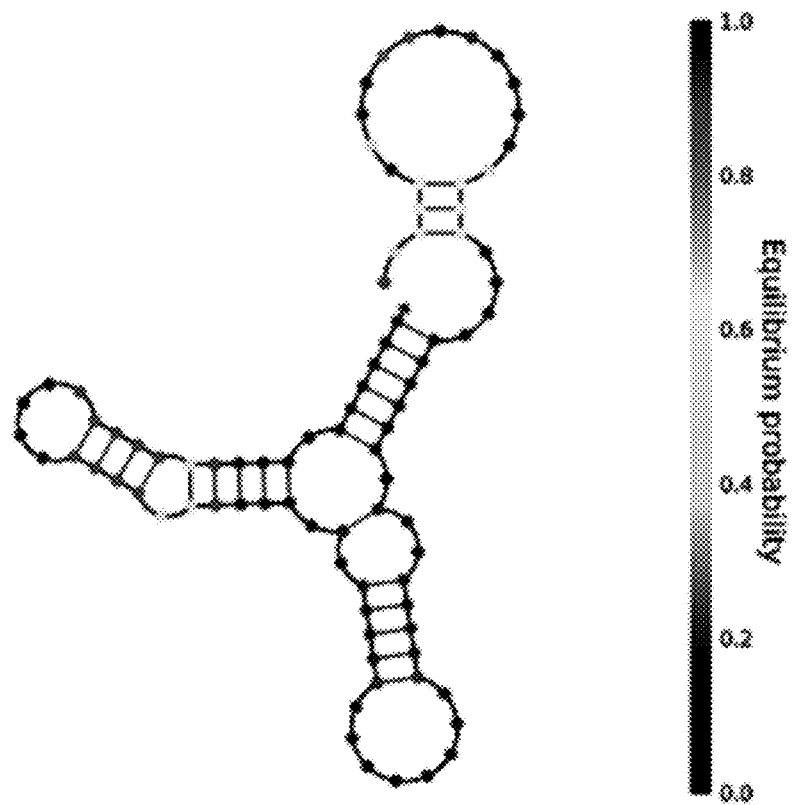

To construct mortalin-CD3ε bispecific aptamers, RNA aptamer against CD3ε recombinant protein was used for protein-SELEX. After 5 rounds of SELEX, deep-sequencing was performed to identify the CD3ε aptamers. Two CD3ε aptamers were identified and named C3e2 and C3e3. The expected structure was depicted by NUPACK (FIGS. 23A-23B). The identified sequences follow.

C3e2: GGAGACAAGAAUAAACGCUCAAAUA-GAAGCAGCAUCUUCCAAAUCAGUUUGUGUGU CCUCUAUUCGACAGGAGGCUCACAACAGGC (SEQ ID NO:37)

C3e3: GGGAGACAAGAAUAAACGCUCAAAUGC-CUGUAGUUCGUAGCGAUUUAACUGCGUCA GUGAGGCUUCGACAGGAGGCUCACAACAGGC (SEQ ID NO:38)

For the functional assay, the binding of CD3ε aptamers to their targets was determined by flow cytometry and confocal microscopy. The binding assay of CD3ε aptamers to human and mice CD3ε was determined on human CD3ε and mice CD3ε expressed HEK293 cells. C3e2 and C3e3 showed the cross-activity on both human CD3ε and mice CD3ε (FIGS. 24A-24B and 25A-25B).

Figure 26A:
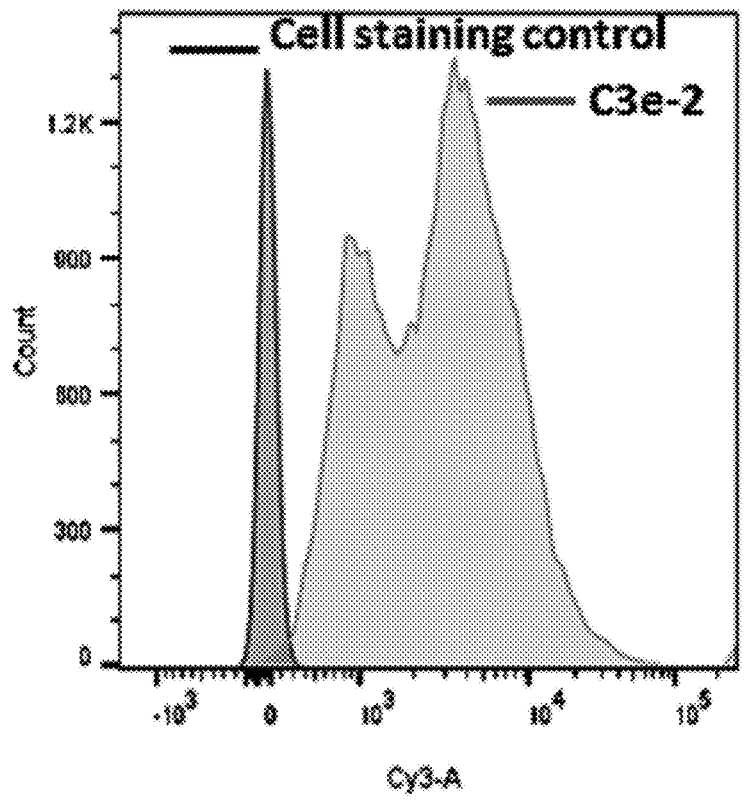
FIGS. 26A-26B. Binding of CD3ε aptamers to human T cells.
Figure 26B:
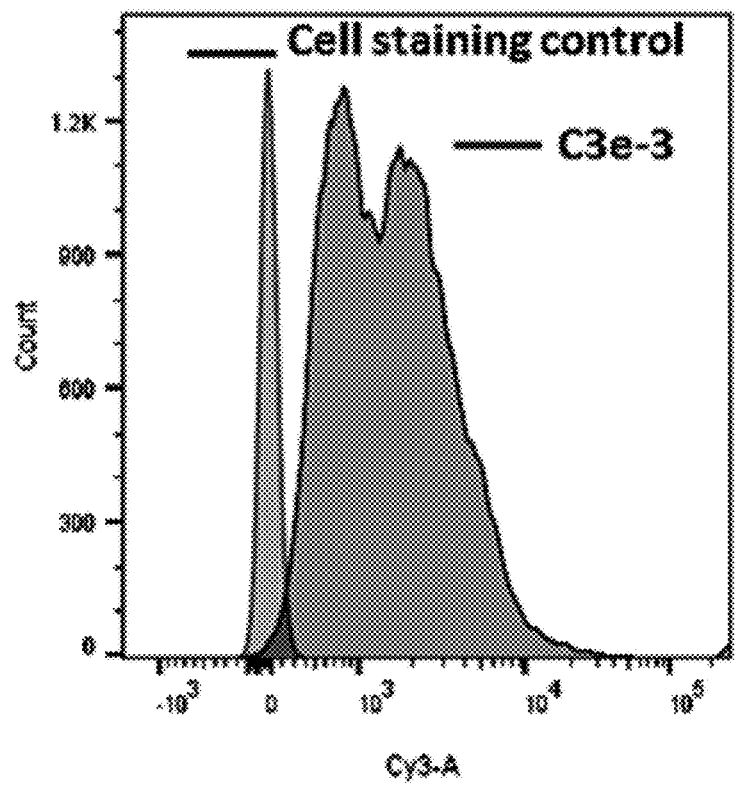

To determine the binding of CD3ε aptamers to their target again, Cy3 labeled CD3ε aptamers were incubated on freshly isolated human T cells and analyzed by flow cytometry. Both aptamers bound to human T cells, showing a shifted histogram (FIGS. 26A-26B). The sequences to construct mortalin bi-specific aptamers follow.

tP19: 5'-GUGUAAUGUAGUAGUCoooooCU-CAAUGGCGAAUGCCCGCCUAAUAGGG-3' (SEQ ID NO:33)

CD3e2; 5'GACUACUACAUUACACoooooGGGA-GACAAGAAUAAACGCUCAAAUAGAAGCAGCA UCUUCCAAAUCAGUUUGUGUGUCCUC-UAUUCGACAGGAGGCUCACAACAGGC-3' (SEQ ID NO:34) Bold: sticky sequence; o: C3 carbon linker CD3e3: 5'GACUACUACAUUACACoooooGGGA-GACAAGAAUAAACGCUCAAAUGCCUGUAGUU CGUAGCGAUUUAACUGCGUCAGUGAGGC-UUCGACAGGAGGCUCACAACAGGC-3' (SEQ ID NO:35). Bold: sticky sequence; o: C3 carbon linker Materials and Methods CD3ε aptamer SELEX To isolated CD3ε aptamer, target proteins were purchased from Creative biomart. The 2'F-RNA aptamers were selected from 40 nucleotide (nt) randomized sequences constructed by in vitro transcription of synthetic DNA templates with NTPs (2'F UTP, 2'F CTP, GTP, ATP, Epicentre Biotechnologies, Madision, WI) and T7 RNA polymerase. To remove RNAs that bind nonspecifically to agarose beads, 1.44 µM of the RNA library was preincubated with 20 µl of Ni-NTA agarose beads in 100 µl binding buffer (30 mM Tris-HCl, pH 7.5, 150 mM NaCl, 5 mM MgCl$_2$, 2 mM dithiothreitol, and 1% BSA, 100 µg/mL yeast tRNA) for 30 min at room temperature with shaking, precipitated by centrifugation, and discarded. The precleared supernatant was transferred to a new tube and incubated with 300 nM of his-tagged human CD3ε (hCD3ε) for 30 min at room temperature. RNAs which bound to hCD3ε were recovered, amplified by RT-PCR and in vitro transcription, and used in the following selection rounds. In subsequent rounds, hCD3ε concentration was reduced by 2-fold at every 2 round for more stringent condition. After 5 rounds of SELEX, the resulting cDNA was amplified. After 5 round of SELEX, deep sequencing was performed to identify the sequences. Two clone of CD3ε aptamer were selected below. Structures of aptamers were predicted using NUPACK using a salt correction algorithm and temperature correction for 25° C.

Internalization Assay of CD3ε Aptamer

Stable cell lines expressing human or mouse CD3 were generated as follows. Lentiviral vectors were constructed encoding fusions proteins consisting of EGFP and either full-length human CD3ε or full-length mouse CD3ε. Lentiviruses were amplified in HEK293T cells, harvested, and used to transfect and generate stable HEK293 cells. For binding studies, 1×10$^5$ cells of human or mouse CD3ε expressing HEK293 cells were seeded in 35-mm glass-bottom dishes (MatTek, Ashland, MA) and grown in appropriate media for 24 hours. Aptamer RNAs were labeled with Cy3 fluorescent dye using the Cy3 Silencer siRNA labeling kit (Thermo Fisher Scientific, Waltham, MA). Cy3-labeled aptamers folded in binding buffer (30 mM Tris-HCl, pH 7.5, 150 mM NaCl, 5 mM MgCl$_2$, 100 µg/mL yeast tRNA) were added to the cells at 200 nM and incubated for 2 hours. Before imaging, cells were washed with DPBS twice. Live-cell confocal imaging was performed with a Zeiss LSM 510 Meta inverted two-photon confocal microscope system using a C-Apo 40×/1.2 NA water immersion objective, and AIM 4.2 software (Carl Zeiss, Jena, Germany). Hoechst 33342 was used for counter-staining the cell nuclei.

Binding Assay of CD3ε Aptamer by Flow Cytometry

Human T cells (1×10⁵ cells/ml), freshly isolated using EasySep Human T cell isolation kit (STEM CELL technologies), were incubated with 500 nM of Cy3-labeled CD3ε aptamer folded in binding buffer for 30 mins on ice. After washing with DPBS, DAPI (1 μg/mL) was added to exclude the dead cells and cells were immediately analyzed by flow cytometry.

What is claimed is:

1. A bi-specific aptamer capable of binding a tumor cell antigen and an immune cell surface protein comprising a first aptamer capable of binding a tumor cell antigen complexed with a second aptamer capable of binding an immune cell surface protein; wherein:
    (i) the first aptamer capable of binding a tumor cell antigen has at least 80% sequence identity to any one of SEQ ID NOS: 1-8 and 28-32; and
    (ii) the immune cell surface protein is CD8.

2. The bi-specific aptamer of claim 1, wherein the immune cell is a T-cell.

3. The bi-specific aptamer of claim 2, wherein the T cell is a T-helper cell, a cytotoxic T cell, a CD8+ T-cell, or CD4+ T-cell.

4. A bi-specific aptamer capable of binding a tumor cell antigen and an immune cell surface protein comprising a first aptamer capable of binding a tumor cell antigen complexed with a second aptamer capable of binding an immune cell surface protein; wherein the immune cell surface protein is CCR5, CCR7, CD2, CD3, CD4, CD7, PD-1, or CTLA4.

5. The bi-specific aptamer of claim 4, wherein the tumor cell antigen is HSP70, vimentin, HSP90, Tfr, or PDGFR-a.

6. The bi-specific aptamer of claim 4, wherein the first aptamer capable of binding a tumor cell antigen comprises a nucleic acid sequence having at least 90% sequence identity to any one of SEQ ID NOS: 1-8 and 28-32.

7. The bi-specific aptamer of claim 4, wherein the second aptamer comprises a nucleic acid sequence having at least 90% sequence identity to any one of SEQ ID NOS:9-16.

8. The bi-specific aptamer of claim 4, wherein the immune cell is a lymphocyte, a T-cell, a B cell, a leukocyte, a macrophage, a neutrophil, or a dendritic cell.

9. The bi-specific aptamer of claim 4, wherein the immune cell is a T-cell.

10. The bi-specific aptamer of claim 9, wherein the T cell is a T-helper cell, a cytotoxic T cell, a CD8+ T-cell, or CD4+ T-cell.

11. The bi-specific aptamer of claim 4, wherein the first aptamer comprises one or more chemically-modified bases or nucleotides.

12. The bi-specific aptamer of claim 4, wherein the first aptamer comprises one or more modifications at the 2' position of ribose.

13. A pharmaceutical composition comprising the bi-specific aptamer according to claim 4 and a pharmaceutically acceptable carrier excipient.

14. A complex comprising the bi-specific aptamer according to claim 4 and (i) a tumor cell expressing a tumor cell antigen to which the bi-specific aptamer is capable of binding or (ii) an immune cell expressing an immune cell surface protein to which the bi-specific aptamer is capable of binding.

15. A complex comprising the bi-specific aptamer according to claim 4, a tumor cell expressing a tumor cell antigen to which the bi-specific aptamer is capable of binding, and an immune cell expressing an immune cell surface protein to which the bi-specific aptamer is capable of binding.

16. A complex comprising the bi-specific aptamer according to claim 1 and (i) a tumor cell expressing a tumor cell antigen to which the bi-specific aptamer is capable of binding or (ii) an immune cell expressing an immune cell surface protein to which the bi-specific aptamer is capable of binding.

17. A complex comprising the bi-specific aptamer according to claim 1, a tumor cell expressing a tumor cell antigen to which the bi-specific aptamer is capable of binding, and an immune cell expressing an immune cell surface protein to which the bi-specific aptamer is capable of binding.

18. The bi-specific aptamer of claim 6, wherein the 3' end or the 5' end of the nucleic acid sequence is conjugated to SEQ ID NO:25, SEQ ID NO:26, or SEQ ID NO:27.

19. The bi-specific aptamer of claim 7, wherein the 3' end or the 5' end of the nucleic acid sequence is conjugated to SEQ ID NO:25, SEQ ID NO:26, or SEQ ID NO:27.

20. The bi-specific aptamer of claim 1, wherein the first aptamer capable of binding the tumor cell antigen has at least 80% sequence identity to SEQ ID NO:1 or SEQ ID NO:8.

21. The bi-specific aptamer of claim 1, wherein the first aptamer capable of binding the tumor cell antigen has at least 80% sequence identity to any one of SEQ ID NOS:2-7.

22. The bi-specific aptamer of claim 1, wherein the first aptamer capable of binding the tumor cell antigen has at least 80% sequence identity to SEQ ID NO:31 or SEQ ID NO:32.

23. The bispecific aptamer of claim 4, wherein the bi-specific aptamer is a bi-specific RNA aptamer, the first aptamer is a first RNA aptamer, and the second aptamer is a second RNA aptamer.

* * * * *

```
                          SEQUENCE LISTING

<160> NUMBER OF SEQ ID NOS: 40

<210> SEQ ID NO 1
<211> LENGTH: 28
<212> TYPE: RNA
<213> ORGANISM: Artificial Sequence
<220> FEATURE:
<223> OTHER INFORMATION: Synthetic polynucleotide

<400> SEQUENCE: 1
cucaauggcg aaugcccgcc uaauaggg                                            28

<210> SEQ ID NO 2
<211> LENGTH: 87
<212> TYPE: RNA
<213> ORGANISM: Artificial Sequence
<220> FEATURE:
<223> OTHER INFORMATION: Synthetic polynucleotide

<400> SEQUENCE: 2
gggagacaag aauaaacgcu caauggcgaa ugcccgccua auagggcguu augacuuguu         60
gaguucgaca ggaggcucac aacaggc                                             87

<210> SEQ ID NO 3
<211> LENGTH: 87
<212> TYPE: RNA
<213> ORGANISM: Artificial Sequence
<220> FEATURE:
<223> OTHER INFORMATION: Synthetic polynucleotide

<400> SEQUENCE: 3
gggagacaag aauaaacgcu caaaguugcg gcccaaccgu uuaauucaga auagugugau         60
gccuucgaca ggaggcucac aacaggc                                             87

<210> SEQ ID NO 4
<211> LENGTH: 87
<212> TYPE: RNA
<213> ORGANISM: Artificial Sequence
<220> FEATURE:
<223> OTHER INFORMATION: Synthetic polynucleotide

<400> SEQUENCE: 4
gggagacaag aauaaacgcu caaugcgcug aaugcccagc cgugaaagcg ucgauuucca         60
uccuucgaca ggaggcucac aacaggc                                             87

<210> SEQ ID NO 5
<211> LENGTH: 87
<212> TYPE: RNA
<213> ORGANISM: Artificial Sequence
<220> FEATURE:
<223> OTHER INFORMATION: Synthetic polynucleotide

<400> SEQUENCE: 5
gggagacaag aauaaacgcu caaaugauug cccauucggu uaugcuugcg cuuccuaaag         60
agcuucgaca ggaggcucac aacaggc                                             87

<210> SEQ ID NO 6
<211> LENGTH: 87
```

```
<212> TYPE: RNA
<213> ORGANISM: Artificial Sequence
<220> FEATURE:
<223> OTHER INFORMATION: Synthetic polynucleotide

<400> SEQUENCE: 6
gggagacaag aauaaacgcu caaggccaug uugaaugccc aacuaagcuu ugagcuugg      60 agcuucgaca ggaggcucac aacaggc                                        87

<210> SEQ ID NO 7
<211> LENGTH: 71
<212> TYPE: RNA
<213> ORGANISM: Artificial Sequence
<220> FEATURE:
<223> OTHER INFORMATION: Synthetic polynucleotide

<400> SEQUENCE: 7
gggagacaag aauaaacgcu caacaaugga gcguuaaacg ugagccauuc gacaggaggc     60
ucacaacagg c                                                         71

<210> SEQ ID NO 8
<211> LENGTH: 8
<212> TYPE: RNA
<213> ORGANISM: Artificial Sequence
<220> FEATURE:
<223> OTHER INFORMATION: Synthetic polynucleotide

<400> SEQUENCE: 8 gaaugccc                                                              8

<210> SEQ ID NO 9
<211> LENGTH: 51
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (8)..(8)
<223> OTHER INFORMATION: Residue modified with 2'-fluoro
<220> FEATURE:
<221> NAME/KEY: misc_feature
<222> LOCATION: (11)..(11)
<223> OTHER INFORMATION: Residue modified with 2'-fluoro
<220> FEATURE:
<221> NAME/KEY: misc_feature
<222> LOCATION: (13)..(13)
<223> OTHER INFORMATION: Residue modified with 2'-fluoro
<220> FEATURE:
<221> NAME/KEY: misc_feature
<222> LOCATION: (18)..(21)
<223> OTHER INFORMATION: Residue modified with 2'-fluoro
<220> FEATURE:
<221> NAME/KEY: misc_feature
<222> LOCATION: (23)..(25)
<223> OTHER INFORMATION: Residue modified with 2'-fluoro
<220> FEATURE:
<221> NAME/KEY: misc_feature
<222> LOCATION: (27)..(30)
<223> OTHER INFORMATION: Residue modified with 2'-fluoro
<220> FEATURE:
<221> NAME/KEY: misc_feature
<222> LOCATION: (32)..(34)
<223> OTHER INFORMATION: Residue modified with 2'-fluoro
<220> FEATURE:
<221> NAME/KEY: misc_feature
<222> LOCATION: (36)..(36)
<223> OTHER INFORMATION: Residue modified with 2'-fluoro
<220> FEATURE:
<221> NAME/KEY: misc_feature
<222> LOCATION: (40)..(40)
```

```
<223> OTHER INFORMATION: Residue modified with 2'-fluoro
<220> FEATURE:
<221> NAME/KEY: misc_feature
<222> LOCATION: (43)..(45)
<223> OTHER INFORMATION: Residue modified with 2'-fluoro
<220> FEATURE:
<221> NAME/KEY: misc_feature
<222> LOCATION: (47)..(49)
<223> OTHER INFORMATION: Residue modified with 2'-fluoro

<400> SEQUENCE: 9
gggaggacga ugcgggccuu cguuuguuuc guccacagac gacucgcccg a            51

<210> SEQ ID NO 10
<211> LENGTH: 20
<212> TYPE: RNA
<213> ORGANISM: Artificial Sequence
<220> FEATURE:
<223> OTHER INFORMATION: Synthetic polynucleotide

<400> SEQUENCE: 10
aucgucuauu agucgcuggc                                               20

<210> SEQ ID NO 11
<211> LENGTH: 20
<212> TYPE: RNA
<213> ORGANISM: Artificial Sequence
<220> FEATURE:
<223> OTHER INFORMATION: Synthetic polynucleotide

<400> SEQUENCE: 11
uccuuggcuu uucgucugug                                               20

<210> SEQ ID NO 12
<211> LENGTH: 20
<212> TYPE: RNA
<213> ORGANISM: Artificial Sequence
<220> FEATURE:
<223> OTHER INFORMATION: Synthetic polynucleotide

<400> SEQUENCE: 12
gccuucguuu guuucgucca                                               20

<210> SEQ ID NO 13
<211> LENGTH: 51
<212> TYPE: RNA
<213> ORGANISM: Artificial Sequence
<220> FEATURE:
<223> OTHER INFORMATION: Synthetic polynucleotide

<400> SEQUENCE: 13
gggaggacga ugcgggccuu cguuuguuuc guccacagac gacucgcccg a            51

<210> SEQ ID NO 14
<211> LENGTH: 20
<212> TYPE: RNA
<213> ORGANISM: Artificial Sequence
<220> FEATURE:
<223> OTHER INFORMATION: Synthetic polynucleotide

<400> SEQUENCE: 14
ucccggcucg uucgucugug                                               20

<210> SEQ ID NO 15
<211> LENGTH: 20
<212> TYPE: RNA
<213> ORGANISM: Artificial Sequence
```

```
-continued

<220> FEATURE:
<223> OTHER INFORMATION: Synthetic polynucleotide

<400> SEQUENCE: 15
uucgucauuu uucgucuggg                                                 20

<210> SEQ ID NO 16
<211> LENGTH: 20
<212> TYPE: RNA
<213> ORGANISM: Artificial Sequence
<220> FEATURE:
<223> OTHER INFORMATION: Synthetic polynucleotide

<400> SEQUENCE: 16
ccuuucgucu guuucugcgc                                                 20

<210> SEQ ID NO 17
<211> LENGTH: 44
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(3)
<223> OTHER INFORMATION: Residue modified with 2'-fluoro
<220> FEATURE:
<221> NAME/KEY: misc_feature
<222> LOCATION: (6)..(6)
<223> OTHER INFORMATION: Residue modified with 2'-fluoro
<220> FEATURE:
<221> NAME/KEY: misc_feature
<222> LOCATION: (9)..(9)
<223> OTHER INFORMATION: Residue modified with 2'-fluoro
<220> FEATURE:
<221> NAME/KEY: misc_feature
<222> LOCATION: (13)..(13)
<223> OTHER INFORMATION: Residue modified with 2'-fluoro
<220> FEATURE:
<221> NAME/KEY: misc_feature
<222> LOCATION: (15)..(17)
<223> OTHER INFORMATION: Residue modified with 2'-fluoro
<220> FEATURE:
<221> NAME/KEY: misc_feature
<222> LOCATION: (19)..(21)
<223> OTHER INFORMATION: Residue modified with 2'-fluoro
<220> FEATURE:
<221> NAME/KEY: misc_feature
<222> LOCATION: (24)..(24)
<223> OTHER INFORMATION: Residue modified with 2'-fluoro
<220> FEATURE:
<221> NAME/KEY: misc_feature
<222> LOCATION: (28)..(28)
<223> OTHER INFORMATION: Residue modified at 3'-position with C3 carbon
      spacers linked to residue at 3'-position
<220> FEATURE:
<221> NAME/KEY: misc_feature
<222> LOCATION: (29)..(29)
<223> OTHER INFORMATION: Residue modified at 5'-position with C3 carbon
      spacers linked to residue at 5'-position
<220> FEATURE:
<221> NAME/KEY: misc_feature
<222> LOCATION: (29)..(29)
<223> OTHER INFORMATION: Residue modified with 2'-O-methyl
<220> FEATURE:
<221> NAME/KEY: misc_feature
<222> LOCATION: (30)..(30)
<223> OTHER INFORMATION: Residue modified with 2'-O-methyl
<220> FEATURE:
<221> NAME/KEY: misc_feature
<222> LOCATION: (31)..(36)
<223> OTHER INFORMATION: Residue modified with 2'-fluoro
<220> FEATURE:
<221> NAME/KEY: misc_feature
<222> LOCATION: (37)..(37)
```

<223> OTHER INFORMATION: Residue modified with 2'-O-methyl
<220> FEATURE:
<221> NAME/KEY: misc_feature
<222> LOCATION: (38)..(38)
<223> OTHER INFORMATION: Residue modified with 2'-fluoro
<220> FEATURE:
<221> NAME/KEY: misc_feature
<222> LOCATION: (39)..(39)
<223> OTHER INFORMATION: Residue modified with 2'-O-methyl
<220> FEATURE:
<221> NAME/KEY: misc_feature
<222> LOCATION: (40)..(43)
<223> OTHER INFORMATION: Residue modified with 2'-fluoro
<220> FEATURE:
<221> NAME/KEY: misc_feature
<222> LOCATION: (44)..(44)
<223> OTHER INFORMATION: Residue modified with 2'-O-methyl

<400> SEQUENCE: 17
cucaauggcg aaugcccgcc uaauagggag uuuuuuacau uuug                44

<210> SEQ ID NO 18
<211> LENGTH: 67
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (8)..(8)
<223> OTHER INFORMATION: Residue modified with 2'-fluoro
<220> FEATURE:
<221> NAME/KEY: misc_feature
<222> LOCATION: (11)..(11)
<223> OTHER INFORMATION: Residue modified with 2'-fluoro
<220> FEATURE:
<221> NAME/KEY: misc_feature
<222> LOCATION: (13)..(13)
<223> OTHER INFORMATION: Residue modified with 2'-fluoro
<220> FEATURE:
<221> NAME/KEY: misc_feature
<222> LOCATION: (17)..(21)
<223> OTHER INFORMATION: Residue modified with 2'-fluoro
<220> FEATURE:
<221> NAME/KEY: misc_feature
<222> LOCATION: (23)..(25)
<223> OTHER INFORMATION: Residue modified with 2'-fluoro
<220> FEATURE:
<221> NAME/KEY: misc_feature
<222> LOCATION: (27)..(30)
<223> OTHER INFORMATION: Residue modified with 2'-fluoro
<220> FEATURE:
<221> NAME/KEY: misc_feature
<222> LOCATION: (32)..(34)
<223> OTHER INFORMATION: Residue modified with 2'-fluoro
<220> FEATURE:
<221> NAME/KEY: misc_feature
<222> LOCATION: (36)..(36)
<223> OTHER INFORMATION: Residue modified with 2'-fluoro
<220> FEATURE:
<221> NAME/KEY: misc_feature
<222> LOCATION: (40)..(40)
<223> OTHER INFORMATION: Residue modified with 2'-fluoro
<220> FEATURE:
<221> NAME/KEY: misc_feature
<222> LOCATION: (43)..(45)
<223> OTHER INFORMATION: Residue modified with 2'-fluoro
<220> FEATURE:
<221> NAME/KEY: misc_feature
<222> LOCATION: (47)..(49)
<223> OTHER INFORMATION: Residue modified with 2'-fluoro
<220> FEATURE:
<221> NAME/KEY: misc_feature
<222> LOCATION: (51)..(51)
<223> OTHER INFORMATION: Residue modified at 3'-position with C3 carbon
      spacers linked to residue at 3'-position
<220> FEATURE:

```
<221> NAME/KEY: misc_feature
<222> LOCATION: (52)..(52)
<223> OTHER INFORMATION: Residue modified at 5'-position with C3 carbon
      spacers linked to residue at 5'-position
<220> FEATURE:
<221> NAME/KEY: misc_feature
<222> LOCATION: (52)..(52)
<223> OTHER INFORMATION: Residue modified with 2'-fluoro
<220> FEATURE:
<221> NAME/KEY: misc_feature
<222> LOCATION: (53)..(56)
<223> OTHER INFORMATION: Residue modified with 2'-O-methyl
<220> FEATURE:
<221> NAME/KEY: misc_feature
<222> LOCATION: (57)..(57)
<223> OTHER INFORMATION: Residue modified with 2'-fluoro
<220> FEATURE:
<221> NAME/KEY: misc_feature
<222> LOCATION: (58)..(58)
<223> OTHER INFORMATION: Residue modified with 2'-O-methyl
<220> FEATURE:
<221> NAME/KEY: misc_feature
<222> LOCATION: (59)..(59)
<223> OTHER INFORMATION: Residue modified with 2'-fluoro
<220> FEATURE:
<221> NAME/KEY: misc_feature
<222> LOCATION: (60)..(65)
<223> OTHER INFORMATION: Residue modified with 2'-O-methyl
<220> FEATURE:
<221> NAME/KEY: misc_feature
<222> LOCATION: (66)..(67)
<223> OTHER INFORMATION: Residue modified with 2'-fluoro

<400> SEQUENCE: 18
gggaggacga ugcgggccuu cguuuguuuc guccacagac gacucgcccg acaaaaugua    60
aaaaacu                                                             67

<210> SEQ ID NO 19
<211> LENGTH: 103
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(7)
<223> OTHER INFORMATION: Residue modified with 2'-fluoro
<220> FEATURE:
<221> NAME/KEY: misc_feature
<222> LOCATION: (13)..(13)
<223> OTHER INFORMATION: Residue modified with 2'-fluoro
<220> FEATURE:
<221> NAME/KEY: misc_feature
<222> LOCATION: (17)..(17)
<223> OTHER INFORMATION: Residue modified with 2'-fluoro
<220> FEATURE:
<221> NAME/KEY: misc_feature
<222> LOCATION: (19)..(21)
<223> OTHER INFORMATION: Residue modified with 2'-fluoro
<220> FEATURE:
<221> NAME/KEY: misc_feature
<222> LOCATION: (24)..(24)
<223> OTHER INFORMATION: Residue modified with 2'-fluoro
<220> FEATURE:
<221> NAME/KEY: misc_feature
<222> LOCATION: (27)..(27)
<223> OTHER INFORMATION: Residue modified with 2'-fluoro
<220> FEATURE:
<221> NAME/KEY: misc_feature
<222> LOCATION: (31)..(31)
<223> OTHER INFORMATION: Residue modified with 2'-fluoro
<220> FEATURE:
<221> NAME/KEY: misc_feature
<222> LOCATION: (33)..(35)
<223> OTHER INFORMATION: Residue modified with 2'-fluoro
<220> FEATURE:
```

```
<221> NAME/KEY: misc_feature
<222> LOCATION: (37)..(39)
<223> OTHER INFORMATION: Residue modified with 2'-fluoro
<220> FEATURE:
<221> NAME/KEY: misc_feature
<222> LOCATION: (42)..(43)
<223> OTHER INFORMATION: Residue modified with 2'-fluoro
<220> FEATURE:
<221> NAME/KEY: misc_feature
<222> LOCATION: (47)..(47)
<223> OTHER INFORMATION: Residue modified with 2'-fluoro
<220> FEATURE:
<221> NAME/KEY: misc_feature
<222> LOCATION: (49)..(50)
<223> OTHER INFORMATION: Residue modified with 2'-fluoro
<220> FEATURE:
<221> NAME/KEY: misc_feature
<222> LOCATION: (52)..(52)
<223> OTHER INFORMATION: Residue modified with 2'-fluoro
<220> FEATURE:
<221> NAME/KEY: misc_feature
<222> LOCATION: (55)..(57)
<223> OTHER INFORMATION: Residue modified with 2'-fluoro
<220> FEATURE:
<221> NAME/KEY: misc_feature
<222> LOCATION: (59)..(60)
<223> OTHER INFORMATION: Residue modified with 2'-fluoro
<220> FEATURE:
<221> NAME/KEY: misc_feature
<222> LOCATION: (64)..(66)
<223> OTHER INFORMATION: Residue modified with 2'-fluoro
<220> FEATURE:
<221> NAME/KEY: misc_feature
<222> LOCATION: (69)..(69)
<223> OTHER INFORMATION: Residue modified with 2'-fluoro
<220> FEATURE:
<221> NAME/KEY: misc_feature
<222> LOCATION: (76)..(78)
<223> OTHER INFORMATION: Residue modified with 2'-fluoro
<220> FEATURE:
<221> NAME/KEY: misc_feature
<222> LOCATION: (80)..(80)
<223> OTHER INFORMATION: Residue modified with 2'-fluoro
<220> FEATURE:
<221> NAME/KEY: misc_feature
<222> LOCATION: (83)..(83)
<223> OTHER INFORMATION: Residue modified with 2'-fluoro
<220> FEATURE:
<221> NAME/KEY: misc_feature
<222> LOCATION: (87)..(87)
<223> OTHER INFORMATION: Residue modified with 2'-fluoro
<220> FEATURE:
<221> NAME/KEY: misc_feature
<222> LOCATION: (87)..(87)
<223> OTHER INFORMATION: Residue modified at 3'-position with C3 carbon
      spacers linked to residue at 3'-position
<220> FEATURE:
<221> NAME/KEY: misc_feature
<222> LOCATION: (88)..(88)
<223> OTHER INFORMATION: Residue modified at 5'-position with C3 carbon
      spacers linked to residue at 5'-position
<220> FEATURE:
<221> NAME/KEY: misc_feature
<222> LOCATION: (88)..(88)
<223> OTHER INFORMATION: Residue modified with 2'-O-methyl
<220> FEATURE:
<221> NAME/KEY: misc_feature
<222> LOCATION: (89)..(89)
<223> OTHER INFORMATION: Residue modified with 2'-O-methyl
<220> FEATURE:
<221> NAME/KEY: misc_feature
<222> LOCATION: (90)..(95)
<223> OTHER INFORMATION: Residue modified with 2'-fluoro
<220> FEATURE:
<221> NAME/KEY: misc_feature
<222> LOCATION: (96)..(96)
<223> OTHER INFORMATION: Residue modified with 2'-O-methyl
<220> FEATURE:
<221> NAME/KEY: misc_feature
```

-continued

```
<222> LOCATION: (97)..(97)
<223> OTHER INFORMATION: Residue modified with 2'-fluoro
<220> FEATURE:
<221> NAME/KEY: misc_feature
<222> LOCATION: (98)..(98)
<223> OTHER INFORMATION: Residue modified with 2'-O-methyl
<220> FEATURE:
<221> NAME/KEY: misc_feature
<222> LOCATION: (99)..(102)
<223> OTHER INFORMATION: Residue modified with 2'-fluoro
<220> FEATURE:
<221> NAME/KEY: misc_feature
<222> LOCATION: (103)..(103)
<223> OTHER INFORMATION: Residue modified with 2'-O-methyl

<400> SEQUENCE: 19
gggagacaag aauaaacgcu caauggcgaa ugcccgccua auagggcguu augacuuguu    60
gaguucgaca ggaggcucac aacaggcagu uuuuuacauu uug                    103

<210> SEQ ID NO 20
<211> LENGTH: 103
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(7)
<223> OTHER INFORMATION: Residue modified with 2'-fluoro
<220> FEATURE:
<221> NAME/KEY: misc_feature
<222> LOCATION: (13)..(13)
<223> OTHER INFORMATION: Residue modified with 2'-fluoro
<220> FEATURE:
<221> NAME/KEY: misc_feature
<222> LOCATION: (17)..(17)
<223> OTHER INFORMATION: Residue modified with 2'-fluoro
<220> FEATURE:
<221> NAME/KEY: misc_feature
<222> LOCATION: (19)..(21)
<223> OTHER INFORMATION: Residue modified with 2'-fluoro
<220> FEATURE:
<221> NAME/KEY: misc_feature
<222> LOCATION: (24)..(24)
<223> OTHER INFORMATION: Residue modified with 2'-fluoro
<220> FEATURE:
<221> NAME/KEY: misc_feature
<222> LOCATION: (26)..(26)
<223> OTHER INFORMATION: Residue modified with 2'-fluoro
<220> FEATURE:
<221> NAME/KEY: misc_feature
<222> LOCATION: (28)..(29)
<223> OTHER INFORMATION: Residue modified with 2'-fluoro
<220> FEATURE:
<221> NAME/KEY: misc_feature
<222> LOCATION: (33)..(33)
<223> OTHER INFORMATION: Residue modified with 2'-fluoro
<220> FEATURE:
<221> NAME/KEY: misc_feature
<222> LOCATION: (35)..(37)
<223> OTHER INFORMATION: Residue modified with 2'-fluoro
<220> FEATURE:
<221> NAME/KEY: misc_feature
<222> LOCATION: (40)..(41)
<223> OTHER INFORMATION: Residue modified with 2'-fluoro
<220> FEATURE:
<221> NAME/KEY: misc_feature
<222> LOCATION: (43)..(43)
<223> OTHER INFORMATION: Residue modified with 2'-fluoro
<220> FEATURE:
<221> NAME/KEY: misc_feature
<222> LOCATION: (49)..(49)
<223> OTHER INFORMATION: Residue modified with 2'-fluoro
<220> FEATURE:
<221> NAME/KEY: misc_feature
<222> LOCATION: (51)..(52)
```

```
<223> OTHER INFORMATION: Residue modified with 2'-fluoro
<220> FEATURE:
<221> NAME/KEY: misc_feature
<222> LOCATION: (55)..(59)
<223> OTHER INFORMATION: Residue modified with 2'-fluoro
<220> FEATURE:
<221> NAME/KEY: misc_feature
<222> LOCATION: (61)..(66)
<223> OTHER INFORMATION: Residue modified with 2'-fluoro
<220> FEATURE:
<221> NAME/KEY: misc_feature
<222> LOCATION: (69)..(69)
<223> OTHER INFORMATION: Residue modified with 2'-fluoro
<220> FEATURE:
<221> NAME/KEY: misc_feature
<222> LOCATION: (76)..(78)
<223> OTHER INFORMATION: Residue modified with 2'-fluoro
<220> FEATURE:
<221> NAME/KEY: misc_feature
<222> LOCATION: (80)..(80)
<223> OTHER INFORMATION: Residue modified with 2'-fluoro
<220> FEATURE:
<221> NAME/KEY: misc_feature
<222> LOCATION: (83)..(83)
<223> OTHER INFORMATION: Residue modified with 2'-fluoro
<220> FEATURE:
<221> NAME/KEY: misc_feature
<222> LOCATION: (87)..(87)
<223> OTHER INFORMATION: Residue modified with 2'-fluoro
<220> FEATURE:
<221> NAME/KEY: misc_feature
<222> LOCATION: (87)..(87)
<223> OTHER INFORMATION: Residue modified at 3'-position with C3 carbon
      spacers linked to residue at 3'-position
<220> FEATURE:
<221> NAME/KEY: misc_feature
<222> LOCATION: (88)..(88)
<223> OTHER INFORMATION: Residue modified at 5'-position with C3 carbon
      spacers linked to residue at 5'-position
<220> FEATURE:
<221> NAME/KEY: misc_feature
<222> LOCATION: (88)..(88)
<223> OTHER INFORMATION: Residue modified with 2'-O-methyl
<220> FEATURE:
<221> NAME/KEY: misc_feature
<222> LOCATION: (89)..(89)
<223> OTHER INFORMATION: Residue modified with 2'-O-methyl
<220> FEATURE:
<221> NAME/KEY: misc_feature
<222> LOCATION: (90)..(95)
<223> OTHER INFORMATION: Residue modified with 2'-fluoro
<220> FEATURE:
<221> NAME/KEY: misc_feature
<222> LOCATION: (96)..(96)
<223> OTHER INFORMATION: Residue modified with 2'-O-methyl
<220> FEATURE:
<221> NAME/KEY: misc_feature
<222> LOCATION: (97)..(97)
<223> OTHER INFORMATION: Residue modified with 2'-fluoro
<220> FEATURE:
<221> NAME/KEY: misc_feature
<222> LOCATION: (98)..(98)
<223> OTHER INFORMATION: Residue modified with 2'-O-methyl
<220> FEATURE:
<221> NAME/KEY: misc_feature
<222> LOCATION: (99)..(102)
<223> OTHER INFORMATION: Residue modified with 2'-fluoro
<220> FEATURE:
<221> NAME/KEY: misc_feature
<222> LOCATION: (103)..(103)
<223> OTHER INFORMATION: Residue modified with 2'-O-methyl

<400> SEQUENCE: 20
gggagacaag aauaaacgcu caaugcgcug aaugcccagc cgugaaagcg ucgauuucca    60
uccuucgaca ggaggcucac aacaggcagu uuuuuacauu uug                     103
```

```
<210> SEQ ID NO 21
<211> LENGTH: 103
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(7)
<223> OTHER INFORMATION: Residue modified with 2'-fluoro
<220> FEATURE:
<221> NAME/KEY: misc_feature
<222> LOCATION: (13)..(13)
<223> OTHER INFORMATION: Residue modified with 2'-fluoro
<220> FEATURE:
<221> NAME/KEY: misc_feature
<222> LOCATION: (17)..(17)
<223> OTHER INFORMATION: Residue modified with 2'-fluoro
<220> FEATURE:
<221> NAME/KEY: misc_feature
<222> LOCATION: (19)..(21)
<223> OTHER INFORMATION: Residue modified with 2'-fluoro
<220> FEATURE:
<221> NAME/KEY: misc_feature
<222> LOCATION: (26)..(27)
<223> OTHER INFORMATION: Residue modified with 2'-fluoro
<220> FEATURE:
<221> NAME/KEY: misc_feature
<222> LOCATION: (29)..(29)
<223> OTHER INFORMATION: Residue modified with 2'-fluoro
<220> FEATURE:
<221> NAME/KEY: misc_feature
<222> LOCATION: (32)..(34)
<223> OTHER INFORMATION: Residue modified with 2'-fluoro
<220> FEATURE:
<221> NAME/KEY: misc_feature
<222> LOCATION: (37)..(38)
<223> OTHER INFORMATION: Residue modified with 2'-fluoro
<220> FEATURE:
<221> NAME/KEY: misc_feature
<222> LOCATION: (40)..(42)
<223> OTHER INFORMATION: Residue modified with 2'-fluoro
<220> FEATURE:
<221> NAME/KEY: misc_feature
<222> LOCATION: (45)..(47)
<223> OTHER INFORMATION: Residue modified with 2'-fluoro
<220> FEATURE:
<221> NAME/KEY: misc_feature
<222> LOCATION: (52)..(52)
<223> OTHER INFORMATION: Residue modified with 2'-fluoro
<220> FEATURE:
<221> NAME/KEY: misc_feature
<222> LOCATION: (55)..(55)
<223> OTHER INFORMATION: Residue modified with 2'-fluoro
<220> FEATURE:
<221> NAME/KEY: misc_feature
<222> LOCATION: (57)..(57)
<223> OTHER INFORMATION: Residue modified with 2'-fluoro
<220> FEATURE:
<221> NAME/KEY: misc_feature
<222> LOCATION: (60)..(60)
<223> OTHER INFORMATION: Residue modified with 2'-fluoro
<220> FEATURE:
<221> NAME/KEY: misc_feature
<222> LOCATION: (62)..(66)
<223> OTHER INFORMATION: Residue modified with 2'-fluoro
<220> FEATURE:
<221> NAME/KEY: misc_feature
<222> LOCATION: (69)..(69)
<223> OTHER INFORMATION: Residue modified with 2'-fluoro
<220> FEATURE:
<221> NAME/KEY: misc_feature
<222> LOCATION: (76)..(78)
<223> OTHER INFORMATION: Residue modified with 2'-fluoro
<220> FEATURE:
<221> NAME/KEY: misc_feature
<222> LOCATION: (80)..(80)
<223> OTHER INFORMATION: Residue modified with 2'-fluoro
<220> FEATURE:
```

```
<221> NAME/KEY: misc_feature
<222> LOCATION: (83)..(83)
<223> OTHER INFORMATION: Residue modified with 2'-fluoro
<220> FEATURE:
<221> NAME/KEY: misc_feature
<222> LOCATION: (87)..(87)
<223> OTHER INFORMATION: Residue modified with 2'-fluoro
<220> FEATURE:
<221> NAME/KEY: misc_feature
<222> LOCATION: (87)..(87)
<223> OTHER INFORMATION: Residue modified at 3'-position with C3 carbon
      spacers linked to residue at 3'-position
<220> FEATURE:
<221> NAME/KEY: misc_feature
<222> LOCATION: (88)..(88)
<223> OTHER INFORMATION: Residue modified at 5'-position with C3 carbon
      spacers linked to residue at 5'-position
<220> FEATURE:
<221> NAME/KEY: misc_feature
<222> LOCATION: (88)..(88)
<223> OTHER INFORMATION: Residue modified with 2'-O-methyl
<220> FEATURE:
<221> NAME/KEY: misc_feature
<222> LOCATION: (89)..(89)
<223> OTHER INFORMATION: Residue modified with 2'-O-methyl
<220> FEATURE:
<221> NAME/KEY: misc_feature
<222> LOCATION: (90)..(95)
<223> OTHER INFORMATION: Residue modified with 2'-fluoro
<220> FEATURE:
<221> NAME/KEY: misc_feature
<222> LOCATION: (96)..(96)
<223> OTHER INFORMATION: Residue modified with 2'-O-methyl
<220> FEATURE:
<221> NAME/KEY: misc_feature
<222> LOCATION: (97)..(97)
<223> OTHER INFORMATION: Residue modified with 2'-fluoro
<220> FEATURE:
<221> NAME/KEY: misc_feature
<222> LOCATION: (98)..(98)
<223> OTHER INFORMATION: Residue modified with 2'-O-methyl
<220> FEATURE:
<221> NAME/KEY: misc_feature
<222> LOCATION: (99)..(102)
<223> OTHER INFORMATION: Residue modified with 2'-fluoro
<220> FEATURE:
<221> NAME/KEY: misc_feature
<222> LOCATION: (103)..(103)
<223> OTHER INFORMATION: Residue modified with 2'-O-methyl

<400> SEQUENCE: 21
gggagacaag aauaaacgcu caaaguugcg gcccaaccgu uuaauucaga auagugugau      60
gccuucgaca ggaggcucac aacaggcagu uuuuuacauu uug                      103

<210> SEQ ID NO 22
<211> LENGTH: 103
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(7)
<223> OTHER INFORMATION: Residue modified with 2'-fluoro
<220> FEATURE:
<221> NAME/KEY: misc_feature
<222> LOCATION: (13)..(13)
<223> OTHER INFORMATION: Residue modified with 2'-fluoro
<220> FEATURE:
<221> NAME/KEY: misc_feature
<222> LOCATION: (17)..(17)
<223> OTHER INFORMATION: Residue modified with 2'-fluoro
<220> FEATURE:
<221> NAME/KEY: misc_feature
<222> LOCATION: (19)..(21)
<223> OTHER INFORMATION: Residue modified with 2'-fluoro
```

```
<220> FEATURE:
<221> NAME/KEY: misc_feature
<222> LOCATION: (25)..(25)
<223> OTHER INFORMATION: Residue modified with 2'-fluoro
<220> FEATURE:
<221> NAME/KEY: misc_feature
<222> LOCATION: (28)..(29)
<223> OTHER INFORMATION: Residue modified with 2'-fluoro
<220> FEATURE:
<221> NAME/KEY: misc_feature
<222> LOCATION: (31)..(33)
<223> OTHER INFORMATION: Residue modified with 2'-fluoro
<220> FEATURE:
<221> NAME/KEY: misc_feature
<222> LOCATION: (35)..(37)
<223> OTHER INFORMATION: Residue modified with 2'-fluoro
<220> FEATURE:
<221> NAME/KEY: misc_feature
<222> LOCATION: (40)..(41)
<223> OTHER INFORMATION: Residue modified with 2'-fluoro
<220> FEATURE:
<221> NAME/KEY: misc_feature
<222> LOCATION: (43)..(43)
<223> OTHER INFORMATION: Residue modified with 2'-fluoro
<220> FEATURE:
<221> NAME/KEY: misc_feature
<222> LOCATION: (45)..(47)
<223> OTHER INFORMATION: Residue modified with 2'-fluoro
<220> FEATURE:
<221> NAME/KEY: misc_feature
<222> LOCATION: (49)..(49)
<223> OTHER INFORMATION: Residue modified with 2'-fluoro
<220> FEATURE:
<221> NAME/KEY: misc_feature
<222> LOCATION: (51)..(56)
<223> OTHER INFORMATION: Residue modified with 2'-fluoro
<220> FEATURE:
<221> NAME/KEY: misc_feature
<222> LOCATION: (63)..(67)
<223> OTHER INFORMATION: Residue modified with 2'-fluoro
<220> FEATURE:
<221> NAME/KEY: misc_feature
<222> LOCATION: (69)..(69)
<223> OTHER INFORMATION: Residue modified with 2'-fluoro
<220> FEATURE:
<221> NAME/KEY: misc_feature
<222> LOCATION: (76)..(78)
<223> OTHER INFORMATION: Residue modified with 2'-fluoro
<220> FEATURE:
<221> NAME/KEY: misc_feature
<222> LOCATION: (80)..(80)
<223> OTHER INFORMATION: Residue modified with 2'-fluoro
<220> FEATURE:
<221> NAME/KEY: misc_feature
<222> LOCATION: (83)..(83)
<223> OTHER INFORMATION: Residue modified with 2'-fluoro
<220> FEATURE:
<221> NAME/KEY: misc_feature
<222> LOCATION: (87)..(87)
<223> OTHER INFORMATION: Residue modified with 2'-fluoro
<220> FEATURE:
<221> NAME/KEY: misc_feature
<222> LOCATION: (87)..(87)
<223> OTHER INFORMATION: Residue modified at 3'-position with C3 carbon
      spacers linked to residue at 3'-position
<220> FEATURE:
<221> NAME/KEY: misc_feature
<222> LOCATION: (88)..(88)
<223> OTHER INFORMATION: Residue modified at 5'-position with C3 carbon
      spacers linked to residue at 5'-position
<220> FEATURE:
<221> NAME/KEY: misc_feature
<222> LOCATION: (88)..(88)
<223> OTHER INFORMATION: Residue modified with 2'-O-methyl
<220> FEATURE:
<221> NAME/KEY: misc_feature
<222> LOCATION: (89)..(89)
<223> OTHER INFORMATION: Residue modified with 2'-O-methyl
<220> FEATURE:
```

```
<221> NAME/KEY: misc_feature
<222> LOCATION: (90)..(95)
<223> OTHER INFORMATION: Residue modified with 2'-fluoro
<220> FEATURE:
<221> NAME/KEY: misc_feature
<222> LOCATION: (96)..(96)
<223> OTHER INFORMATION: Residue modified with 2'-O-methyl
<220> FEATURE:
<221> NAME/KEY: misc_feature
<222> LOCATION: (97)..(97)
<223> OTHER INFORMATION: Residue modified with 2'-fluoro
<220> FEATURE:
<221> NAME/KEY: misc_feature
<222> LOCATION: (98)..(98)
<223> OTHER INFORMATION: Residue modified with 2'-O-methyl
<220> FEATURE:
<221> NAME/KEY: misc_feature
<222> LOCATION: (99)..(102)
<223> OTHER INFORMATION: Residue modified with 2'-fluoro
<220> FEATURE:
<221> NAME/KEY: misc_feature
<222> LOCATION: (103)..(103)
<223> OTHER INFORMATION: Residue modified with 2'-O-methyl

<400> SEQUENCE: 22
gggagacaag aauaaacgcu caaaugauug cccauucggu uaugcuugcg cuuccuaaag     60
agcuucgaca ggaggcucac aacaggcagu uuuuuacauu uug                     103

<210> SEQ ID NO 23
<211> LENGTH: 103
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(7)
<223> OTHER INFORMATION: Residue modified with 2'-fluoro
<220> FEATURE:
<221> NAME/KEY: misc_feature
<222> LOCATION: (13)..(13)
<223> OTHER INFORMATION: Residue modified with 2'-fluoro
<220> FEATURE:
<221> NAME/KEY: misc_feature
<222> LOCATION: (17)..(17)
<223> OTHER INFORMATION: Residue modified with 2'-fluoro
<220> FEATURE:
<221> NAME/KEY: misc_feature
<222> LOCATION: (19)..(21)
<223> OTHER INFORMATION: Residue modified with 2'-fluoro
<220> FEATURE:
<221> NAME/KEY: misc_feature
<222> LOCATION: (26)..(27)
<223> OTHER INFORMATION: Residue modified with 2'-fluoro
<220> FEATURE:
<221> NAME/KEY: misc_feature
<222> LOCATION: (29)..(29)
<223> OTHER INFORMATION: Residue modified with 2'-fluoro
<220> FEATURE:
<221> NAME/KEY: misc_feature
<222> LOCATION: (31)..(32)
<223> OTHER INFORMATION: Residue modified with 2'-fluoro
<220> FEATURE:
<221> NAME/KEY: misc_feature
<222> LOCATION: (36)..(36)
<223> OTHER INFORMATION: Residue modified with 2'-fluoro
<220> FEATURE:
<221> NAME/KEY: misc_feature
<222> LOCATION: (38)..(40)
<223> OTHER INFORMATION: Residue modified with 2'-fluoro
<220> FEATURE:
<221> NAME/KEY: misc_feature
<222> LOCATION: (43)..(44)
<223> OTHER INFORMATION: Residue modified with 2'-fluoro
<220> FEATURE:
<221> NAME/KEY: misc_feature
```

```
<222> LOCATION: (48)..(51)
<223> OTHER INFORMATION: Residue modified with 2'-fluoro
<220> FEATURE:
<221> NAME/KEY: misc_feature
<222> LOCATION: (55)..(58)
<223> OTHER INFORMATION: Residue modified with 2'-fluoro
<220> FEATURE:
<221> NAME/KEY: misc_feature
<222> LOCATION: (63)..(66)
<223> OTHER INFORMATION: Residue modified with 2'-fluoro
<220> FEATURE:
<221> NAME/KEY: misc_feature
<222> LOCATION: (69)..(69)
<223> OTHER INFORMATION: Residue modified with 2'-fluoro
<220> FEATURE:
<221> NAME/KEY: misc_feature
<222> LOCATION: (76)..(78)
<223> OTHER INFORMATION: Residue modified with 2'-fluoro
<220> FEATURE:
<221> NAME/KEY: misc_feature
<222> LOCATION: (80)..(80)
<223> OTHER INFORMATION: Residue modified with 2'-fluoro
<220> FEATURE:
<221> NAME/KEY: misc_feature
<222> LOCATION: (83)..(83)
<223> OTHER INFORMATION: Residue modified with 2'-fluoro
<220> FEATURE:
<221> NAME/KEY: misc_feature
<222> LOCATION: (87)..(87)
<223> OTHER INFORMATION: Residue modified with 2'-fluoro
<220> FEATURE:
<221> NAME/KEY: misc_feature
<222> LOCATION: (87)..(87)
<223> OTHER INFORMATION: Residue modified at 3'-position with C3 carbon
      spacers linked to residue at 3'-position
<220> FEATURE:
<221> NAME/KEY: misc_feature
<222> LOCATION: (88)..(88)
<223> OTHER INFORMATION: Residue modified at 5'-position with C3 carbon
      spacers linked to residue at 5'-position
<220> FEATURE:
<221> NAME/KEY: misc_feature
<222> LOCATION: (88)..(88)
<223> OTHER INFORMATION: Residue modified with 2'-O-methyl
<220> FEATURE:
<221> NAME/KEY: misc_feature
<222> LOCATION: (89)..(89)
<223> OTHER INFORMATION: Residue modified with 2'-O-methyl
<220> FEATURE:
<221> NAME/KEY: misc_feature
<222> LOCATION: (90)..(95)
<223> OTHER INFORMATION: Residue modified with 2'-fluoro
<220> FEATURE:
<221> NAME/KEY: misc_feature
<222> LOCATION: (96)..(96)
<223> OTHER INFORMATION: Residue modified with 2'-O-methyl
<220> FEATURE:
<221> NAME/KEY: misc_feature
<222> LOCATION: (97)..(97)
<223> OTHER INFORMATION: Residue modified with 2'-fluoro
<220> FEATURE:
<221> NAME/KEY: misc_feature
<222> LOCATION: (98)..(98)
<223> OTHER INFORMATION: Residue modified with 2'-O-methyl
<220> FEATURE:
<221> NAME/KEY: misc_feature
<222> LOCATION: (99)..(102)
<223> OTHER INFORMATION: Residue modified with 2'-fluoro
<220> FEATURE:
<221> NAME/KEY: misc_feature
<222> LOCATION: (103)..(103)
<223> OTHER INFORMATION: Residue modified with 2'-O-methyl

<400> SEQUENCE: 23
gggagacaag aauaaacgcu caaggccaug uugaaugccc aacuaagcuu ugagcuuugg      60
agcuucgaca ggaggcucac aacaggcagu uuuuuacauu uug                      103
```

```
<210> SEQ ID NO 24
<211> LENGTH: 87
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(7)
<223> OTHER INFORMATION: Residue modified with 2'-fluoro
<220> FEATURE:
<221> NAME/KEY: misc_feature
<222> LOCATION: (13)..(13)
<223> OTHER INFORMATION: Residue modified with 2'-fluoro
<220> FEATURE:
<221> NAME/KEY: misc_feature
<222> LOCATION: (17)..(17)
<223> OTHER INFORMATION: Residue modified with 2'-fluoro
<220> FEATURE:
<221> NAME/KEY: misc_feature
<222> LOCATION: (19)..(21)
<223> OTHER INFORMATION: Residue modified with 2'-fluoro
<220> FEATURE:
<221> NAME/KEY: misc_feature
<222> LOCATION: (24)..(24)
<223> OTHER INFORMATION: Residue modified with 2'-fluoro
<220> FEATURE:
<221> NAME/KEY: misc_feature
<222> LOCATION: (27)..(27)
<223> OTHER INFORMATION: Residue modified with 2'-fluoro
<220> FEATURE:
<221> NAME/KEY: misc_feature
<222> LOCATION: (30)..(30)
<223> OTHER INFORMATION: Residue modified with 2'-fluoro
<220> FEATURE:
<221> NAME/KEY: misc_feature
<222> LOCATION: (32)..(32)
<223> OTHER INFORMATION: Residue modified with 2'-fluoro
<220> FEATURE:
<221> NAME/KEY: misc_feature
<222> LOCATION: (34)..(35)
<223> OTHER INFORMATION: Residue modified with 2'-fluoro
<220> FEATURE:
<221> NAME/KEY: misc_feature
<222> LOCATION: (39)..(39)
<223> OTHER INFORMATION: Residue modified with 2'-fluoro
<220> FEATURE:
<221> NAME/KEY: misc_feature
<222> LOCATION: (41)..(41)
<223> OTHER INFORMATION: Residue modified with 2'-fluoro
<220> FEATURE:
<221> NAME/KEY: misc_feature
<222> LOCATION: (45)..(46)
<223> OTHER INFORMATION: Residue modified with 2'-fluoro
<220> FEATURE:
<221> NAME/KEY: misc_feature
<222> LOCATION: (48)..(50)
<223> OTHER INFORMATION: Residue modified with 2'-fluoro
<220> FEATURE:
<221> NAME/KEY: misc_feature
<222> LOCATION: (53)..(53)
<223> OTHER INFORMATION: Residue modified with 2'-fluoro
<220> FEATURE:
<221> NAME/KEY: misc_feature
<222> LOCATION: (60)..(62)
<223> OTHER INFORMATION: Residue modified with 2'-fluoro
<220> FEATURE:
<221> NAME/KEY: misc_feature
<222> LOCATION: (64)..(64)
<223> OTHER INFORMATION: Residue modified with 2'-fluoro
<220> FEATURE:
<221> NAME/KEY: misc_feature
<222> LOCATION: (67)..(67)
<223> OTHER INFORMATION: Residue modified with 2'-fluoro
<220> FEATURE:
<221> NAME/KEY: misc_feature
<222> LOCATION: (71)..(71)
<223> OTHER INFORMATION: Residue modified with 2'-fluoro
```

```
<220> FEATURE:
<221> NAME/KEY: misc_feature
<222> LOCATION: (71)..(71)
<223> OTHER INFORMATION: Residue modified at 3'-position with C3 carbon
      spacers linked to residue at 3'-position
<220> FEATURE:
<221> NAME/KEY: misc_feature
<222> LOCATION: (72)..(72)
<223> OTHER INFORMATION: Residue modified at 5'-position with C3 carbon
      spacers linked to residue at 5'-position
<220> FEATURE:
<221> NAME/KEY: misc_feature
<222> LOCATION: (72)..(72)
<223> OTHER INFORMATION: Residue modified with 2'-O-methyl
<220> FEATURE:
<221> NAME/KEY: misc_feature
<222> LOCATION: (73)..(73)
<223> OTHER INFORMATION: Residue modified with 2'-O-methyl
<220> FEATURE:
<221> NAME/KEY: misc_feature
<222> LOCATION: (74)..(79)
<223> OTHER INFORMATION: Residue modified with 2'-fluoro
<220> FEATURE:
<221> NAME/KEY: misc_feature
<222> LOCATION: (80)..(80)
<223> OTHER INFORMATION: Residue modified with 2'-O-methyl
<220> FEATURE:
<221> NAME/KEY: misc_feature
<222> LOCATION: (81)..(81)
<223> OTHER INFORMATION: Residue modified with 2'-fluoro
<220> FEATURE:
<221> NAME/KEY: misc_feature
<222> LOCATION: (82)..(82)
<223> OTHER INFORMATION: Residue modified with 2'-O-methyl
<220> FEATURE:
<221> NAME/KEY: misc_feature
<222> LOCATION: (83)..(86)
<223> OTHER INFORMATION: Residue modified with 2'-fluoro
<220> FEATURE:
<221> NAME/KEY: misc_feature
<222> LOCATION: (87)..(87)
<223> OTHER INFORMATION: Residue modified with 2'-O-methyl

<400> SEQUENCE: 24
gggagacaag aauaaacgcu caacaaugga gcguuaaacg ugagccauuc gacaggaggc    60
ucacaacagg caguuuuuua cauuuug                                        87

<210> SEQ ID NO 25
<211> LENGTH: 16
<212> TYPE: RNA
<213> ORGANISM: Artificial Sequence
<220> FEATURE:
<223> OTHER INFORMATION: Synthetic polynucleotide

<400> SEQUENCE: 25
aguuuuuuac auuuug                                                    16

<210> SEQ ID NO 26
<211> LENGTH: 16
<212> TYPE: RNA
<213> ORGANISM: Artificial Sequence
<220> FEATURE:
<223> OTHER INFORMATION: Synthetic polynucleotide

<400> SEQUENCE: 26
caaaauguaa aaaacu                                                    16

<210> SEQ ID NO 27
<211> LENGTH: 16
<212> TYPE: RNA
<213> ORGANISM: Artificial Sequence
<220> FEATURE:
```

<223> OTHER INFORMATION: Synthetic polynucleotide

<400> SEQUENCE: 27
caaaauguaa aaaacu                                              16

<210> SEQ ID NO 28
<211> LENGTH: 87
<212> TYPE: RNA
<213> ORGANISM: Artificial Sequence
<220> FEATURE:
<223> OTHER INFORMATION: Synthetic polynucleotide

<400> SEQUENCE: 28
gggagacaag aauaaacgcu caaugcguuc acguuuauuc acauuuuga auugagcaug   60 agcuucgaca ggaggcucac aacaggc                                    87

<210> SEQ ID NO 29
<211> LENGTH: 87
<212> TYPE: RNA
<213> ORGANISM: Artificial Sequence
<220> FEATURE:
<223> OTHER INFORMATION: Synthetic polynucleotide

<400> SEQUENCE: 29
gggagacaag aauaaacgcu caaugcguuu acguuuauuc acauuuuga auugagcaug   60 agcuucgaca ggaggcucac aacaggc                                    87

<210> SEQ ID NO 30
<211> LENGTH: 43
<212> TYPE: RNA
<213> ORGANISM: Artificial Sequence
<220> FEATURE:
<223> OTHER INFORMATION: Synthetic polynucleotide

<400> SEQUENCE: 30
ggggcucaau gcguucacgu uuauucacau uuugaauug agc                   43

<210> SEQ ID NO 31
<211> LENGTH: 90
<212> TYPE: RNA
<213> ORGANISM: Artificial Sequence
<220> FEATURE:
<223> OTHER INFORMATION: Synthetic polynucleotide

<400> SEQUENCE: 31
gggagagcgg aagcgugcug ggccugcucu uuaauaaacc cacuuucgaa caucagcgua   60
uguccauaac ccagagguga uggaucccccc                                90

<210> SEQ ID NO 32
<211> LENGTH: 90
<212> TYPE: RNA
<213> ORGANISM: Artificial Sequence
<220> FEATURE:
<223> OTHER INFORMATION: Synthetic polynucleotide

<400> SEQUENCE: 32
gggagagcgg aagcgugcug ggccuauugc aucuuucugu uauuuccgaa uccgucccga   60
cugucauaac ccagagguga uggaucccccc                                90

<210> SEQ ID NO 33
<211> LENGTH: 44
<212> TYPE: RNA
<213> ORGANISM: Artificial Sequence

```
<220> FEATURE:
<223> OTHER INFORMATION: Synthetic polynucleotide
<220> FEATURE:
<221> NAME/KEY: misc_feature
<222> LOCATION: (16)..(16)
<223> OTHER INFORMATION: Residue modified at 3'-position with C3 carbon
      spacers linked to residue at 3'-position
<220> FEATURE:
<221> NAME/KEY: misc_feature
<222> LOCATION: (17)..(17)
<223> OTHER INFORMATION: Residue modified at 5'-position with C3 carbon
      spacers linked to residue at 5'-position

<400> SEQUENCE: 33
guguaaugua guaguccuca auggcgaaug cccgccuaau aggg                   44

<210> SEQ ID NO 34
<211> LENGTH: 103
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (16)..(16)
<223> OTHER INFORMATION: Residue modified at 3'-position with C3 carbon
      spacers linked to residue at 3'-position
<220> FEATURE:
<221> NAME/KEY: misc_feature
<222> LOCATION: (17)..(17)
<223> OTHER INFORMATION: Residue modified at 5'-position with C3 carbon
      spacers linked to residue at 5'-position

<400> SEQUENCE: 34
gacuacuaca uuacacggga gacaagaaua aacgcucaaa uagaagcagc aucuuccaaa    60
ucaguuugug uguccucuau ucgacaggag gcucacaaca ggc                    103

<210> SEQ ID NO 35
<211> LENGTH: 103
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (16)..(16)
<223> OTHER INFORMATION: Residue modified at 3'-position with C3 carbon
      spacers linked to residue at 3'-position
<220> FEATURE:
<221> NAME/KEY: misc_feature
<222> LOCATION: (17)..(17)
<223> OTHER INFORMATION: Residue modified at 5'-position with C3 carbon
      spacers linked to residue at 5'-position

<400> SEQUENCE: 35
gacuacuaca uuacacggga gacaagaaua aacgcucaaa ugccuguagu ucguagcgau    60
uuaacugcgu cagugaggcu ucgacaggag gcucacaaca ggc                    103

<210> SEQ ID NO 36
<211> LENGTH: 87
<212> TYPE: DNA
<213> ORGANISM: Artificial Sequence
<220> FEATURE:
<223> OTHER INFORMATION: Synthetic polynucleotide

<400> SEQUENCE: 36
gggagacaag aataaacgct caaagttgcg gcccaaccgt ttaattcaga atagtgtgat    60
gccttcgaca ggaggctcac aacaggc                                      87
```

```
<210> SEQ ID NO 37
<211> LENGTH: 86
<212> TYPE: RNA
<213> ORGANISM: Artificial Sequence
<220> FEATURE:
<223> OTHER INFORMATION: Synthetic polynucleotide

<400> SEQUENCE: 37
ggagacaaga auaaacgcuc aaauagaagc agcaucuucc aaaucaguuu gugguccuc      60 uauucgacag gaggcucaca acaggc                                          86

<210> SEQ ID NO 38
<211> LENGTH: 87
<212> TYPE: RNA
<213> ORGANISM: Artificial Sequence
<220> FEATURE:
<223> OTHER INFORMATION: Synthetic polynucleotide

<400> SEQUENCE: 38
gggagacaag aauaaacgcu caaaugccug uaguucguag cgauuuaacu gcgucaguga     60
ggcuucgaca ggaggcucac aacaggc                                         87

<210> SEQ ID NO 39
<211> LENGTH: 44
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: Residue modified at 3'-position with C3 carbon
      spacers linked to residue at 3'-position
<220> FEATURE:
<221> NAME/KEY: misc_feature
<222> LOCATION: (29)..(29)
<223> OTHER INFORMATION: Residue modified at 5'-position with C3 carbon
      spacers linked to residue at 5'-position

<400> SEQUENCE: 39
cucaauggcg aaugcccgcc uaauagggag uuuuuuacau uuug                      44

<210> SEQ ID NO 40
<211> LENGTH: 466
<212> TYPE: PRT
<213> ORGANISM: Homo sapiens

<400> SEQUENCE: 40

Met Ser Thr Arg Ser Val Ser Ser Ser Tyr Arg Arg Met Phe Gly
1               5                   10                  15

Gly Pro Gly Thr Ala Ser Arg Pro Ser Ser Ser Arg Ser Tyr Val Thr
            20                  25                  30

Thr Ser Thr Arg Thr Tyr Ser Leu Gly Ser Ala Leu Arg Pro Ser Thr
        35                  40                  45

Ser Arg Ser Leu Tyr Ala Ser Ser Pro Gly Gly Val Tyr Ala Thr Arg
    50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
            100                 105                 110
```

```
Arg Phe Ala Asn Tyr Ile Asp Lys Val Arg Phe Leu Glu Gln Gln Asn
            115                 120                 125

Lys Ile Leu Leu Ala Glu Leu Glu Gln Leu Lys Gly Gln Gly Lys Ser
            130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
                180                 185                 190

Met Leu Gln Arg Glu Glu Ala Glu Asn Thr Leu Gln Ser Phe Arg Gln
            195                 200                 205

Asp Val Asp Asn Ala Ser Leu Ala Arg Leu Asp Leu Glu Arg Lys Val
            210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
                260                 265                 270

Arg Gln Gln Tyr Glu Ser Val Ala Ala Lys Asn Leu Gln Glu Ala Glu
            275                 280                 285

Glu Trp Tyr Lys Ser Lys Phe Ala Asp Leu Ser Glu Ala Ala Asn Arg
            290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
                340                 345                 350

Val Glu Ala Ala Asn Tyr Gln Asp Thr Ile Gly Arg Leu Gln Asp Glu
            355                 360                 365

Ile Gln Asn Met Lys Glu Glu Met Ala Arg His Leu Arg Glu Tyr Gln
            370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                405                 410                 415

Asn Phe Ser Ser Leu Asn Leu Arg Glu Thr Asn Leu Asp Ser Leu Pro
                420                 425                 430

Leu Val Asp Thr His Ser Lys Arg Thr Leu Leu Ile Lys Thr Val Glu
            435                 440                 445

Thr Arg Asp Gly Gln Val Ile Asn Glu Thr Ser Gln His His Asp Asp
            450                 455                 460

Leu Glu
465
```